United States Patent
Mohan et al.

(10) Patent No.: US 10,905,687 B2
(45) Date of Patent: Feb. 2, 2021

(54) SUBSTITUTED PIPERAZINES AS ROR-GAMMA MODULATORS

(71) Applicant: ESCALIER BIOSCIENCES B.V., Encinitas, CA (US)

(72) Inventors: Raju Mohan, Encinitas, CA (US); John Nuss, Carlsbad, CA (US); Jason Harris, Carlsbad, CA (US)

(73) Assignee: ESCALIER BIOSCIENCES B.V., Encinitas, CA (US)

( * ) Notice: Subject to any disclaimer, the term of this patent is extended or adjusted under 35 U.S.C. 154(b) by 0 days.

(21) Appl. No.: 16/344,919

(22) PCT Filed: Oct. 27, 2017

(86) PCT No.: PCT/US2017/058755
§ 371 (c)(1),
(2) Date: Apr. 25, 2019

(87) PCT Pub. No.: WO2018/081558
PCT Pub. Date: May 3, 2018

(65) Prior Publication Data
US 2019/0269674 A1    Sep. 5, 2019

Related U.S. Application Data

(60) Provisional application No. 62/413,907, filed on Oct. 27, 2016.

(51) Int. Cl.
| | |
|---|---|
| *A61K 31/495* | (2006.01) |
| *C07D 295/04* | (2006.01) |
| *A61P 17/10* | (2006.01) |
| *A61P 17/06* | (2006.01) |
| *A61P 17/08* | (2006.01) |
| *A61P 17/02* | (2006.01) |
| *A61K 9/00* | (2006.01) |
| *A61Q 19/08* | (2006.01) |
| *C07D 401/06* | (2006.01) |
| *A61P 17/00* | (2006.01) |

(52) U.S. Cl.
CPC .......... *A61K 31/495* (2013.01); *A61K 9/0014* (2013.01); *A61P 17/00* (2018.01); *A61P 17/02* (2018.01); *A61P 17/06* (2018.01); *A61P 17/08* (2018.01); *A61P 17/10* (2018.01); *A61Q 19/08* (2013.01); *C07D 401/06* (2013.01)

(58) Field of Classification Search
CPC .................. A61K 31/495; C07D 295/04
USPC ..................... 514/252.12; 544/358
See application file for complete search history.

(56) References Cited

U.S. PATENT DOCUMENTS

| | | |
|---|---|---|
| 6,432,957 B1 | 8/2002 | Kodoma et al. |
| 2010/0029621 A1 | 2/2010 | Cooke et al. |
| 2014/0031330 A1 | 1/2014 | Bodil et al. |
| 2014/0187554 A1 | 7/2014 | Kamenecka et al. |

FOREIGN PATENT DOCUMENTS

| | | |
|---|---|---|
| WO | WO-2004032933 A1 | 4/2004 |
| WO | WO-2018081558 A1 | 5/2018 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*
Amselem et al.: In vitro tests to predict in vivo performance of liposomal dosage forms. Chem Phys Lipids 64: 219-237 (1993).

(Continued)

*Primary Examiner* — Douglas M Willis
(74) *Attorney, Agent, or Firm* — Wilson Sonsini Goodrich & Rosati

(57) ABSTRACT

Described herein are retinoic acid related-related orphan nuclear receptor (ROR) modulators of Formula (I) and pharmaceutical compositions thereof, and methods of utilizing these RORγ modulators in the treatment of dermal diseases, disorders or conditions:

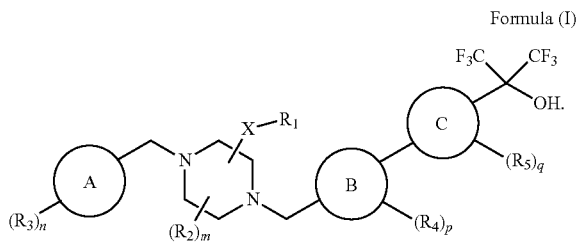

Formula (I)

Amendment to the abstract of disclosure showing mark-up:
Described herein are retinoic acid related-related orphan nuclear receptor (ROR) modulators of Formula (I) and pharmaceutical compositions thereof, and methods of utilizing these RORγ modulators in the treatment of dermal diseases, disorders or conditions:

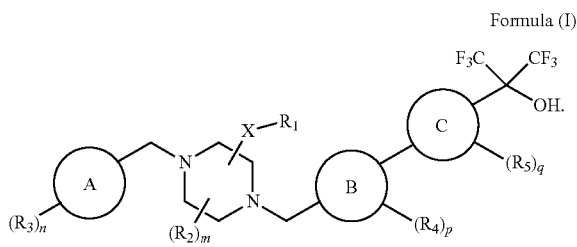

Formula (I)

21 Claims, 3 Drawing Sheets

(56) References Cited

OTHER PUBLICATIONS

Burnham et al.: Polymers for delivering peptides and proteins. Am J Hosp Pharm 51: 210-218 (1994).
Davis et al.: Enzyme polyethylene glycol adducts: modified enzymes with unique properties. Enzyme Eng 4:169-173 (1978).
International Application No. PCT/US2017/058755 International Preliminary Report on Patentability dated Apr. 30, 2019.
International Application No. PCT/US2017/058755 International Search Report and Written Opinion dated Feb. 23, 2018.
Science IP Search Results (2016) 93 pages.

* cited by examiner

SUBSTITUTED PIPERAZINES AS ROR-GAMMA MODULATORS

CROSS-REFERENCE

This application is a U.S. national stage application of International Application No. PCT/US2017/058755, filed Oct. 27, 2017, which claims the benefit of U.S. Provisional Application No. 62/413,907, filed on Oct. 27, 2016, both of which are herein incorporated by reference in their entirety.

BACKGROUND OF THE INVENTION

The retinoic acid related orphan nuclear receptors (RORs) have three members: RORα, RORβ and RORγ. RORβ expression is mostly restricted to the brain and retina, while RORα and RORγ expressions are wide spread. RORγ also has a shorter isoform, RORγt, which is mostly expressed in the immune system.

RORγt is essential for the development of secondary lymphoid tissues, in particular lymph nodes and Peyer's patches. Recent studies identified a critical role for RORγt in lineage specification of uncommitted CD4+ T helper cells into Th17 cells as well as the development of Tc17 (cytotoxic) T cells. Th17 response has been implicated in a myriad of autoimmune diseases such as psoriasis, inflammatory bowel disease, arthritis and multiple scoliosis. Inhibition of Th17 and Tc17 response has also been shown to a mechanism for cancer cells to evade anti-tumor immunity in several experimental tumor models. These findings implicate both RORγ agonists and inverse agonists as potential therapeutics for a variety of diseases.

SUMMARY OF THE INVENTION

Described herein are compounds of Formula (I), (Ia), or (Ib), pharmaceutical compositions that include such compounds, and methods of use thereof, for modulating RORγ. In one aspect is the topical administration of at least one RORγ modulator described herein to the skin of a mammal in the treatment of dermal diseases, disorders or conditions.

Provided herein are methods and compositions comprising topical administration of an RORγ modulator for treatment of dermal diseases, disorders or conditions. Dermal diseases, disorders or conditions include, but are not limited to, skin aging, scarring, psoriasis, dermatitis, eczema, urticaria, rosacea, burns, acne, or any other condition described herein. Dermal diseases or disorders also refer to pigmentary disorders including but not limited to vitiligo. Dermal diseases also refer to skin malignancies and cancer, including melanoma and metastatic forms of these diseases.

Accordingly, provided herein are methods and compositions for maintenance of the dermal barrier and/or normalization of the dermal barrier and/or reducing injury to the dermal barrier and/or regeneration of the dermal barrier.

In one aspect provided herein is a method for treating the epidermis of a mammalian subject suffering from a perturbed epidermal barrier function, said method comprising topically administering to said epidermis a topical composition comprising an active ingredient that is a modulator of RORγ, said active ingredient being present in a concentration that is effective in enhancing barrier development.

In another aspect, provided herein is a method for treating the epidermis or mucous membrane of a terrestrial mammalian subject suffering from a condition of disturbed differentiation or excess proliferation, said method comprising topically administering to said epidermis or mucous membrane a topical composition comprising an active ingredient that is a modulator of RORγ, said active ingredient being present in a concentration that is effective in enhancing barrier development.

In some embodiments of the methods or compositions described above, the modulator of RORγ is a compound of Formula (I), (Ia), or (Ib) as described herein. In some embodiments of the methods or compositions described above, the modulator of RORγ is a compound of Formula (I), (Ia), or (Ib) as described herein. In some embodiments of the methods or compositions described above, the concentration of said active ingredient in the topical composition is from about 0.1 μM to 100 μM.

In one aspect is the use of a RORγ modulator in the manufacture of a topical formulation for use in the treatment of a dermal disease, disorder or condition in a mammal. In one aspect is the use of an RORγ modulator and a second therapeutic agent in the manufacture of a topical formulation for use in the treatment of a dermal disease, disorder or condition in a mammal.

In one aspect is a compound of Formula (I):

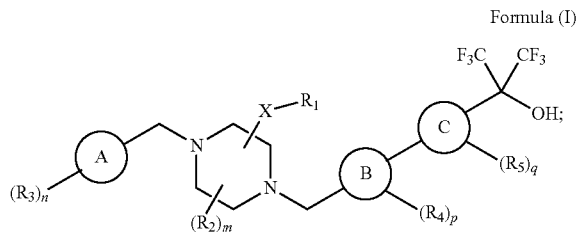

Formula (I)

wherein:

is phenyl, or a 5-membered or 6-membered heteroaryl ring;

is phenyl, or a 5-membered or 6-membered heteroaryl ring;

is phenyl, or a 5-membered or 6-membered heteroaryl ring;
X is a bond, $C_1$-$C_6$alkyl, or $C_1$-$C_6$heteroalkyl;
$R_1$ is —C(=O)O$R_6$ or —C(=O)N($R_6$)$_2$;
each $R_2$ is independently halogen, $C_1$-$C_6$alkyl, or $C_1$-$C_6$alkoxy;
each $R_3$, each $R_4$, and each $R_5$ are each independently halogen, $C_1$-$C_6$alkyl, $C_1$-$C_6$haloalkyl, $C_1$-$C_6$alkoxy, $C_1$-$C_6$heteroalkyl, —O$R_7$, —N($R_7$)$_2$, —CN, —C(=O)R, —C(=O)O$R_7$, —C(=O)N($R_7$)$_2$, —N$R_7$C(=O)$R_8$, —N$R_7$SO$_2R_8$, —SO$_2R_8$, or —SO$_2$N($R_7$)$_2$;
each $R_6$ is independently hydrogen, $C_1$-$C_6$alkyl, or —$C_1$-$C_6$alkyl-Y—$R_9$;
each Y is independently —O—, —S—, or —N($R_{10}$)—;

each $R_7$ is independently hydrogen, $C_1$-$C_6$alkyl, $C_1$-$C_6$haloalkyl, or $C_1$-$C_6$heteroalkyl;

each $R_8$ is independently $C_1$-$C_6$alkyl or $C_1$-$C_6$heteroalkyl;

each $R_9$ is independently hydrogen or $C_1$-$C_6$alkyl;

each $R_{10}$ is independently hydrogen or $C_1$-$C_6$alkyl;

m is 0, 1, 2, 3, or 4;

n is 0, 1, 2, 3, or 4;

p is 0, 1, 2, 3, or 4; and q is 0, 1, 2, or 3;

or a pharmaceutically acceptable salt or solvate thereof.

In one embodiment is a compound of Formula (I) wherein

Ⓐ is phenyl or a 6-membered heteroaryl ring. In a further embodiment is a compound of Formula (I) wherein

Ⓐ is phenyl. In a further embodiment is a compound of Formula (I) wherein

Ⓐ is a 6-membered heteroaryl ring. In a further embodiment is a compound of Formula (I) wherein

Ⓐ is pyridyl. In another embodiment is a compound of Formula (I) wherein

Ⓑ is phenyl or a 6-membered heteroaryl ring. In a further embodiment is a compound of Formula (I) wherein

Ⓑ is phenyl. In a further embodiment is a compound of Formula (I) wherein

Ⓑ is a 6-membered heteroaryl ring. In a further embodiment is a compound of Formula (I) wherein

Ⓑ is pyridyl. In another embodiment is a compound of Formula (I) wherein

Ⓒ is phenyl or a 6-membered heteroaryl ring. In a further embodiment is a compound of Formula (I) wherein

Ⓒ is phenyl. In a further embodiment is a compound of Formula (I) wherein

Ⓒ is a 6-membered heteroaryl ring. In a further embodiment is a compound of Formula (I) wherein

Ⓒ is pyridyl. In a further embodiment is a compound of Formula (Ia) having the structure:

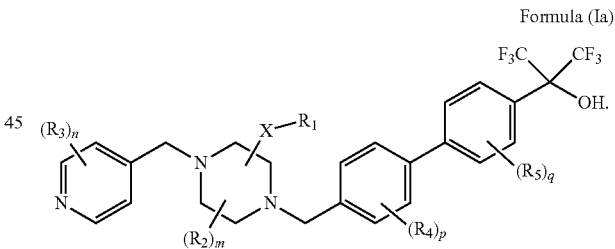

Formula (Ia)

In another embodiment is a compound of Formula (I) or (Ia) wherein $R_1$ is —C(═O)OR$_6$. In a further embodiment is a compound of Formula (I) or (Ia) wherein $R_6$ is $C_1$-$C_6$alkyl. In a further embodiment is a compound of Formula (I) or (Ia) wherein $R_1$ is —C(═O)OCH$_3$, —C(═O)OCH$_2$CH$_3$, or —C(═O)OCH(CH$_3$)$_2$. In a further embodiment is a compound of Formula (I) or (Ia) wherein $R_1$ is —C(═O)OCH$_3$ or —C(═O)OCH$_2$CH$_3$. In another embodiment is a compound of Formula (I) or (Ia) wherein $R_1$ is —C(═O)OR$_6$ and $R_6$ is —C$_1$-C$_6$alkyl-Y—R$_9$. In a further embodiment is a compound of Formula (I) or (Ia) wherein $R_1$ is —C(═O)OR$_6$, $R_6$ is —C$_1$-C$_6$alkyl-Y—R$_9$, and Y is —O—. In a further embodiment is a compound of Formula (I) or (Ia) wherein $R_1$ is —C(═O)OR$_6$, $R_6$ is —C$_1$-C$_6$alkyl-Y—R$_9$, Y is —O—, and $R_9$ is hydrogen. In a further embodiment is a compound of Formula (I) or (Ia)

wherein $R_1$ is —C(=O)OCH$_2$CH$_2$OH. In another embodiment is a compound of Formula (I) or (Ia) wherein $R_1$ is —C(=O)OR$_6$, $R_6$ is —C$_1$-C$_6$alkyl-Y—R$_9$, Y is —O—, and $R_9$ is C$_1$-C$_6$alkyl. In a further embodiment is a compound of Formula (I) or (Ia) wherein $R_1$ is —C(=O)OCH$_2$CH$_2$OCH$_2$CH$_3$. In another embodiment is a compound of Formula (I) or (Ia) wherein $R_1$ is —C(=O)OR$_6$, $R_6$ is —C$_1$-C$_6$alkyl-Y—R$_9$, and Y is —N(R$_{10}$)—. In a further embodiment is a compound of Formula (I) or (Ia) wherein $R_1$ is —C(=O)OR$_6$, $R_6$ is —C$_1$-C$_6$alkyl-Y—R$_9$, Y is —N(R$_{10}$)—, and $R_9$ is hydrogen. In a further embodiment is a compound of Formula (I) or (Ia) wherein $R_1$ is —C(=O)OCH$_2$CH$_2$NH$_2$. In a further embodiment is a compound of Formula (I) or (Ia) wherein $R_1$ is —C(=O)N(R$_6$)$_2$. In another embodiment is a compound of Formula (I) or (Ia) wherein $R_1$ is —C(=O)N(R$_6$)$_2$ and $R_6$ is —C$_1$-C$_6$alkyl. In another embodiment is a compound of Formula (I) or (Ia) wherein X is a bond. In another embodiment is a compound of Formula (I) or (Ia) wherein X is —C$_1$-C$_6$alkyl. In a further embodiment is a compound of Formula (I) or (Ia) wherein X is —CH$_2$—. In another embodiment is a compound of Formula (I) or (Ia) wherein each $R_3$, each $R_4$, and each $R_5$ are each independently halogen, C$_1$-C$_6$alkyl, C$_1$-C$_6$haloalkyl, or C$_1$-C$_6$alkoxy. In another embodiment is a compound of Formula (I) or (Ia) wherein m is 0 or 1, and n is 0 or 1. In another embodiment is a compound of Formula (I) or (Ia) wherein m is 0 and n is 0. In another embodiment is a compound of Formula (I) or (Ia) wherein m is 0, n is 0, and q is 0. In another embodiment is a compound of Formula (I) or (Ia) wherein p is 0 or 1, and q is 0. In another embodiment is a compound of Formula (I) or (Ia) wherein p is 1, $R_4$ is C$_1$-C$_6$alkyl, and q is 0 or 1. In another embodiment is a compound of Formula (I) or (Ia) wherein m is 0 or 1, n is 0 or 1, p is 0 or 1, and q is 0 or 1. In another embodiment is a compound of Formula (I) or (Ia) wherein m is 0, n is 0, p is 0, and q is 0.

In another aspect is a compound of Formula (Ib):

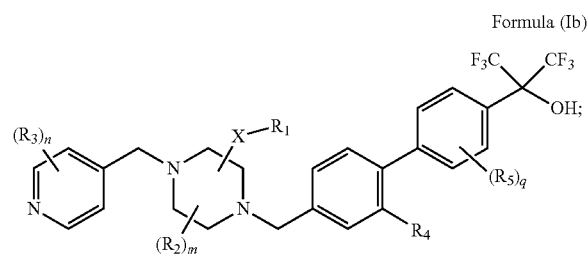

Formula (Ib)

wherein:
X is a bond, C$_1$-C$_6$alkyl, or C$_1$-C$_6$heteroalkyl;
$R_1$ is —C(=O)OR$_6$ or —C(=O)N(R$_6$)$_2$;
each $R_2$ is independently halogen, C$_1$-C$_6$alkyl, or C$_1$-C$_6$alkoxy;
each $R_3$ is independently halogen, C$_1$-C$_6$alkyl, C$_1$-C$_6$haloalkyl, C$_1$-C$_6$alkoxy, C$_1$-C$_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$SO$_2$R$_8$, —SO$_2$R$_8$, or —SO$_2$N(R$_7$)$_2$;
$R_4$ is hydrogen or C$_1$-C$_6$alkyl;
each $R_5$ is independently halogen, C$_1$-C$_6$alkyl, C$_1$-C$_6$haloalkyl, C$_1$-C$_6$alkoxy, C$_1$-C$_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$SO$_2$R$_8$, —SO$_2$R$_8$, or —SO$_2$N(R$_7$)$_2$;
each $R_6$ is independently hydrogen, C$_1$-C$_6$alkyl, or —C$_1$-C$_6$alkyl-Y—R$_9$;
each Y is independently —O—, —S—, or —N(R$_{10}$)—;
each $R_7$ is independently hydrogen, C$_1$-C$_6$alkyl, C$_1$-C$_6$haloalkyl, or C$_1$-C$_6$heteroalkyl;
each $R_8$ is independently C$_1$-C$_6$alkyl or C$_1$-C$_6$heteroalkyl;
each $R_9$ is independently hydrogen or C$_1$-C$_6$alkyl;
each $R_{10}$ is independently hydrogen or C$_1$-C$_6$alkyl;
m is 0, 1, 2, 3, or 4;
n is 0, 1, 2, 3, or 4; and
q is 0, 1, 2, or 3;
or a pharmaceutically acceptable salt or solvate thereof.

In another embodiment is a compound of Formula (Ib) wherein $R_1$ is —C(=O)OR$_6$. In a further embodiment is a compound of Formula (Ib) wherein $R_6$ is C$_1$-C$_6$alkyl. In a further embodiment is a compound of Formula (Ib) wherein $R_1$ is —C(=O)OCH$_3$, —C(=O)OCH$_2$CH$_3$, or —C(=O)OCH(CH$_3$)$_2$. In a further embodiment is a compound of Formula (Ib) wherein $R_1$ is —C(=O)OCH$_3$ or —C(=O)OCH$_2$CH$_3$. In another embodiment is a compound of Formula (Ib) wherein $R_1$ is —C(=O)OR$_6$ and $R_6$ is —C$_1$-C$_6$alkyl-Y—R$_9$. In a further embodiment is a compound of Formula (Ib) wherein $R_1$ is —C(=O)OR$_6$, $R_6$ is —C$_1$-C$_6$alkyl-Y—R$_9$, and Y is —O—. In a further embodiment is a compound of Formula (Ib) wherein $R_1$ is —C(=O)OR$_6$, $R_6$ is —C$_1$-C$_6$alkyl-Y—R$_9$, Y is —O—, and $R_9$ is hydrogen. In a further embodiment is a compound of Formula (Ib) wherein $R_1$ is —C(=O)OCH$_2$CH$_2$OH. In another embodiment is a compound of Formula (Ib) wherein $R_1$ is —C(=O)OR$_6$, $R_6$ is —C$_1$-C$_6$alkyl-Y—R$_9$, Y is —O—, and $R_9$ is C$_1$-C$_6$alkyl. In a further embodiment is a compound of Formula (Ib) wherein $R_1$ is —C(=O)OCH$_2$CH$_2$OCH$_2$CH$_3$. In another embodiment is a compound of Formula (Ib) wherein $R_1$ is —C(=O)OR$_6$, $R_6$ is —C$_1$-C$_6$alkyl-Y—R$_9$, and Y is —N(R$_{10}$)—. In a further embodiment is a compound of Formula (Ib) wherein $R_1$ is —C(=O)OR$_6$, $R_6$ is —C$_1$-C$_6$alkyl-Y—R$_9$, Y is —N(R$_{10}$)—, and $R_9$ is hydrogen. In a further embodiment is a compound of Formula (Ib) wherein $R_1$ is —C(=O)OCH$_2$CH$_2$NH$_2$. In a further embodiment is a compound of Formula (Ib) wherein $R_1$ is —C(=O)N(R$_6$)$_2$. In another embodiment is a compound of Formula (Ib) wherein $R_1$ is —C(=O)N(R$_6$)$_2$ and $R_6$ is —C$_1$-C$_6$alkyl. In another embodiment is a compound of Formula (Ib) wherein X is a bond. In another embodiment is a compound of Formula (Ib) wherein X is —C$_1$-C$_6$alkyl. In a further embodiment is a compound of Formula (Ib) wherein X is —CH$_2$—. In another embodiment is a compound of Formula (Ib) wherein each $R_3$ and each $R_5$ are each independently halogen, C$_1$-C$_6$alkyl, C$_1$-C$_6$haloalkyl, or C$_1$-C$_6$alkoxy. In another embodiment is a compound of Formula (Ib) wherein m is 0 or 1, n is 0 or 1, and q is 0 or 1. In another embodiment is a compound of Formula (Ib) wherein m is 0, n is 0, and q is 0. In another embodiment is a compound of Formula (Ib) wherein $R_4$ is hydrogen. In another embodiment is a compound of Formula (Ib) wherein $R_4$ is C$_1$-C$_6$alkyl. In another embodiment is a compound of Formula (Ib) wherein $R_4$ is —CH$_3$.

In another embodiment is a compound selected from:

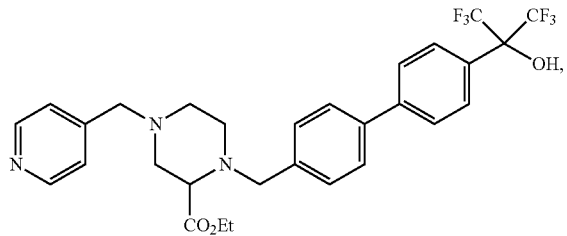

-continued
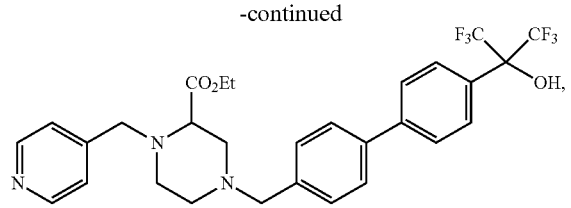
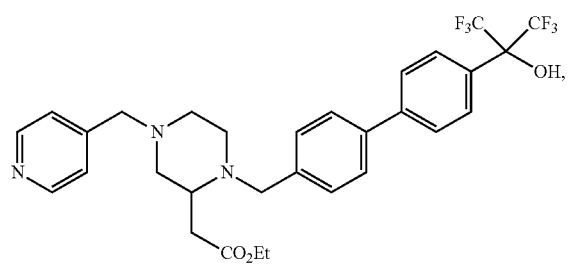
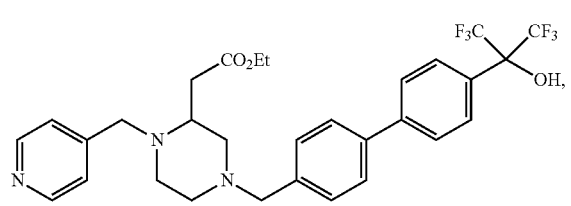
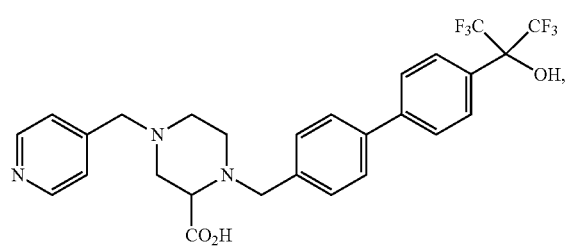
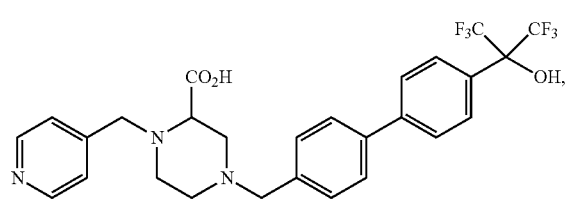
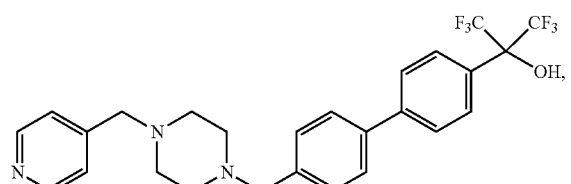
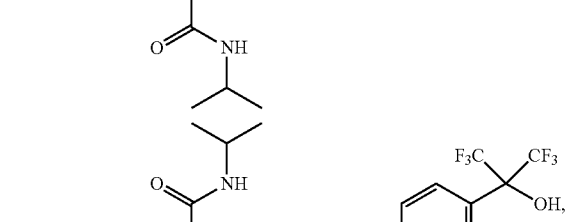
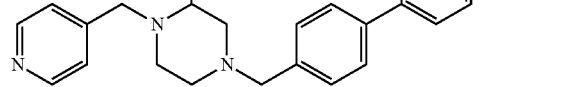
-continued
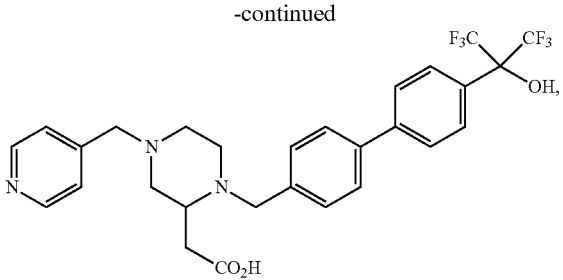
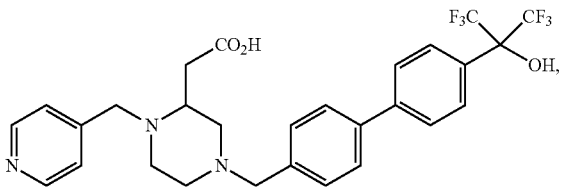
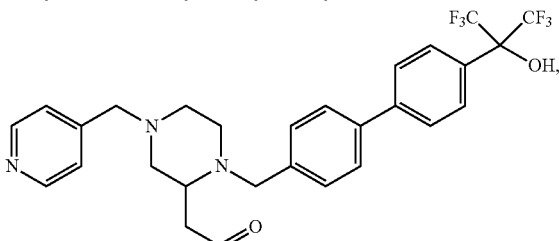
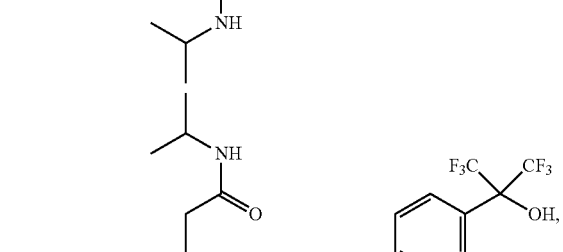
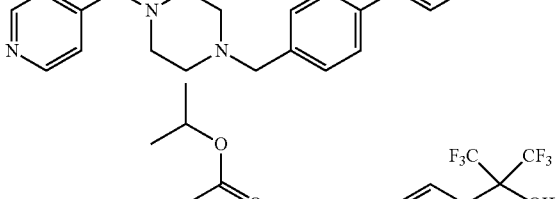
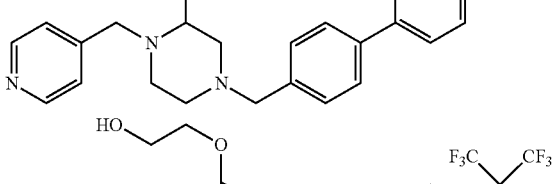
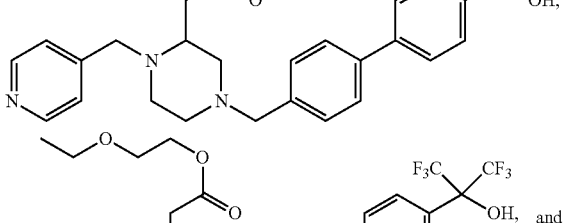
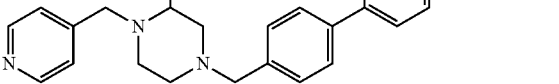
and

9

-continued

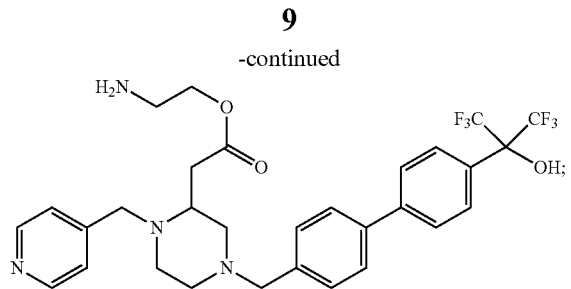

or a pharmaceutically acceptable salt or solvate thereof.

In another embodiment is a compound selected from:

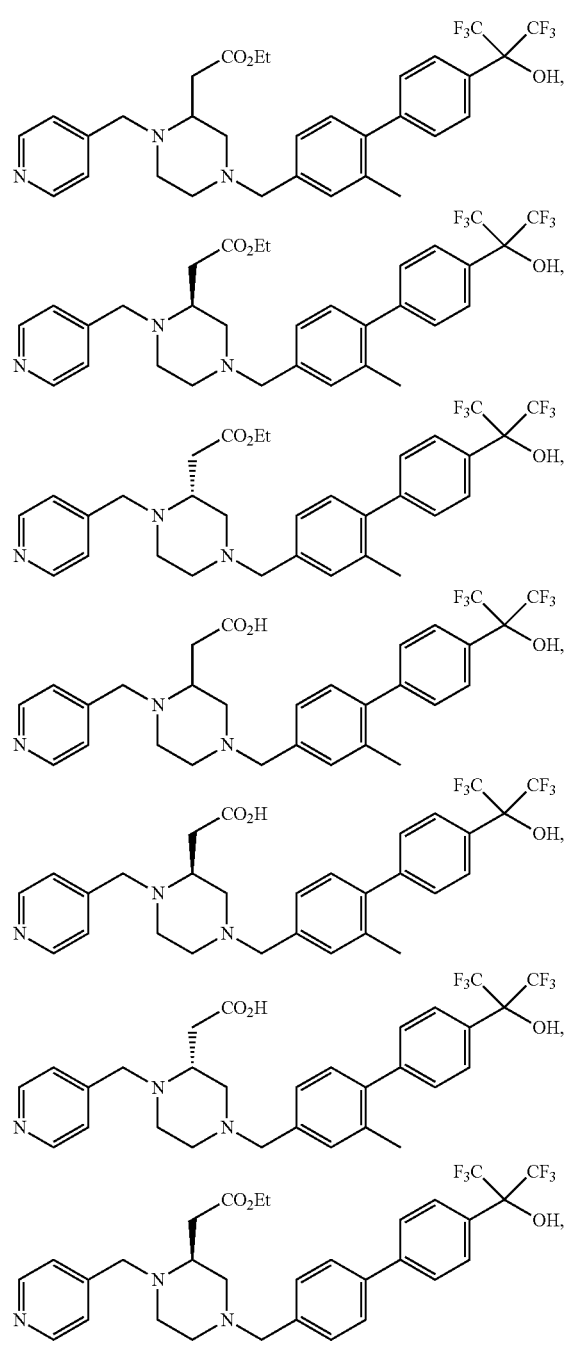

10

-continued

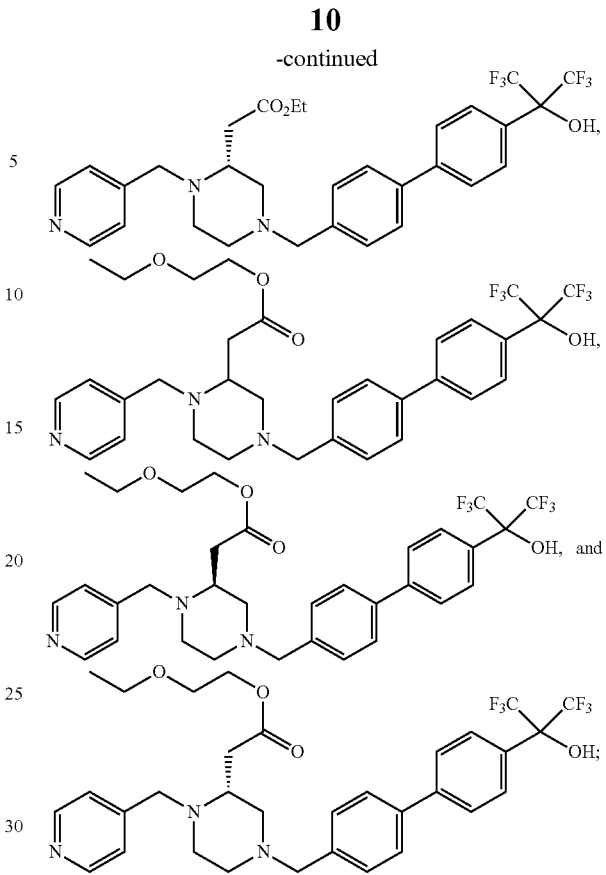

or a pharmaceutically acceptable salt or solvate thereof.

In another aspect is a pharmaceutical composition comprising a pharmaceutically acceptable diluent, excipient, carrier or binder, and a compound of Formula (I), (Ia), or (Ib), or a pharmaceutically acceptable salt or solvate thereof.

In another aspect is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is selected from the group consisting of skin aging, scarring, psoriasis, dermatitis, eczema, urticaria, rosacea, burns, and acne.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
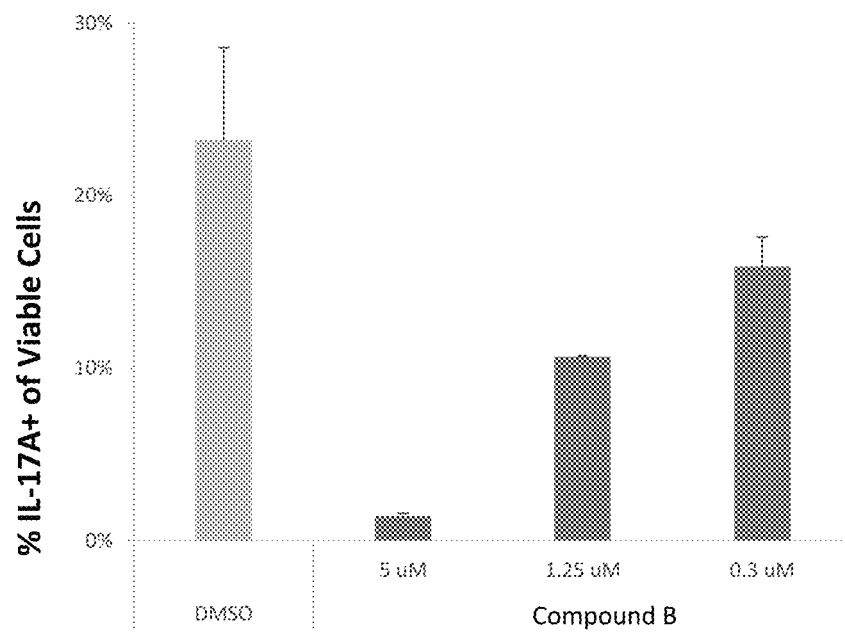
FIG. 1 shows the inhibition of Th17 cell differentiation with reduction of IL-17A+ cells in the presence of a compound of Formula (I) (Compound B).

Provided herein are methods and compositions comprising RORγ modulators as active ingredients in a formulation that is pharmaceutically acceptable for topical administration.

Topical formulations containing RORγ modulators described herein are applied to beneficial effect to skin and/or mucus membranes. The activators are formulated as lotions, solutions, gels, creams, emollient creams, unguents, sprays, or any other form that will permit topical application. The formulation may also contain one or more agents that promote the spreading of the formulation over the affected area, but are otherwise biologically inactive. Examples of these agents are surfactants, humectants, wetting agents, emulsifiers, or propellants.

Amounts that are referred to herein as effective in enhancing barrier development are any amount that will cause a substantial relief of the symptoms of a disrupted or dysfunctional epidermal permeability barrier when applied repeatedly over time. The optimum amounts in any given instance will be readily apparent to those skilled in the art or are capable of determination by routine experimentation.

Examples of skin conditions that are susceptible to topical treatment with RORγ modulators are: atopic and seborrheic dermatitis; inflammation to mucous membranes, such as cheilitis, chapped lips, nasal irritation and vulvovaginitis; eczematous dermatitis resulting from allergic and irritant contact, eczema craquelee, radiation and stasis dermatitis; ulcers and erosions due to chemical or thermal burns, bullous disorders, or vascular compromise or ischemia including venous, arterial, embolic or diabetic ulcers; ichthyoses, with or without an associated barrier abnormality; epidermolysis bullosa; psoriasis; hypertrophic scars and keloids; intrinsic aging, photo aging and/or dermatoheliosus; melanoma and non-melanoma skin cancer, including lignin melanoma, basal cell carcinoma, squamous cell carcinoma, actinic keratoses, and virally induced neoplasia (warts and condylomata accuminata).

Optimal methods and frequency of administration will be readily apparent to those skilled in the art or are capable of determination by routine experimentation. Effective results in most cases are achieved by topical application of a thin layer over the affected area, or the area where one seeks to achieve the desired effect. Depending on the condition being addressed, its stage or degree, and whether application is done for therapeutic or preventive reasons, effective results are achieved with application rates of from one application every two or three days to four or more applications per day.

The methods and compositions described herein are generally applicable to the treatment of mammalian skin including for example humans, domestic pets, and livestock and other farm animals.

Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

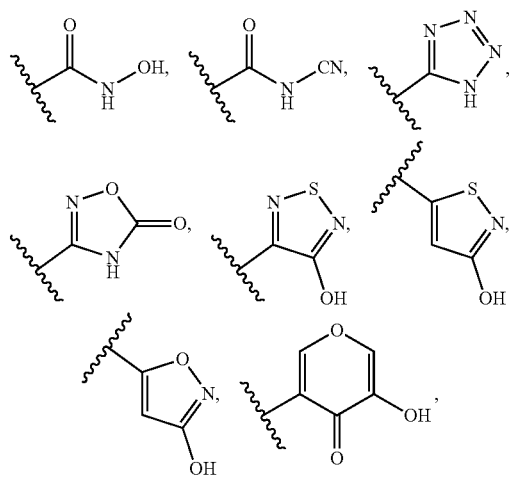

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—$N(CH_3)$—$CH_3$, —$CH_2$—$CH_2$—NH—$CH_3$, —$CH_2$—$CH_2$—$N(CH_3)$—$CH_3$, —$CH_2$—S—$CH_2$—$CH_3$, —$CH_2$—$CH_2$—S(O)—$CH_3$, —$CH_2$—$CH_2$—$S(O)_2$—$CH_3$, —$CH_2$—NH—$OCH_3$, —$CH_2$—O—$Si(CH_3)_3$, —$CH_2$—CH=N—$OCH_3$, and —CH=CH—$N(CH_3)$—$CH_3$. In addition, up to two heteroatoms may be consecutive, such as, by way of example, —$CH_2$—NH—$OCH_3$ and —$CH_2$—O—$Si(CH_3)_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —$N(R)_2$), and the protected derivatives thereof. By way of example, an optional substituents may be $L^sR^s$, wherein each $L^s$ is independently selected from a bond, —O—, —C(=O)—, —S—, —S(=O)—, —$S(=O)_2$—, —NH—, —NHC(O)—, —C(O)NH—, $S(=O)_2NH$—, —$NHS(=O)_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

As used herein, the term "about" or "approximately" means within 20%, preferably within 10%, and more preferably within 5% of a given value or range.

The term a "therapeutically effective amount" as used herein refers to the amount of an RORγ modulator that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

The term "soft-drug" as used herein, refers to drug substance and/or a chemical compound that is biologically active in the desired target tissue and that is metabolized, after exerting its effect in the target tissue, to a compound that is inactive against the biological target. In some embodiments, the soft-drug has no target biological activity in systemic circulation.

The term "skin aging" includes conditions derived from intrinsic chronological aging (for example, deepened expression lines, reduction of skin thickness, inelasticity, and/or unblemished smooth surface), those derived from photoaging (for example, deep wrinkles, yellow and leathery surface, hardening of the skin, elastosis, roughness, dyspigmentations (age spots) and/or blotchy skin), and those derived from steroid-induced skin thinning.

RORγ Modulators

RORγ modulators contemplated for use in the compositions and methods described herein are compounds with RORγ modulator activities. The term "RORγ modulator" includes RORγ and/or RORγt agonists and inverse agonists.

In some embodiments is a compound of Formula (I):

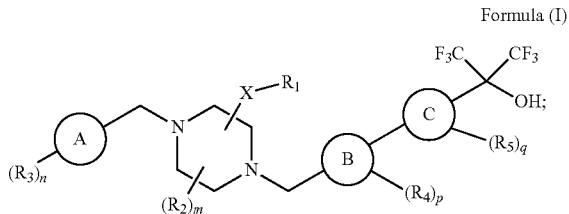

Formula (I)

wherein:

is phenyl, or a 5-membered or 6-membered heteroaryl ring;

is phenyl, or a 5-membered or 6-membered heteroaryl ring;

is phenyl, or a 5-membered or 6-membered heteroaryl ring;
X is a bond, $C_1$-$C_6$alkyl, or $C_1$-$C_6$heteroalkyl;
$R_1$ is —C(=O)O$R_6$ or —C(=O)N($R_6$)$_2$;
each $R_2$ is independently halogen, $C_1$-$C_6$alkyl, or $C_1$-$C_6$alkoxy;
each $R_3$, each $R_4$, and each $R_5$ are each independently halogen, $C_1$-$C_6$alkyl, $C_1$-$C_6$haloalkyl, $C_1$-$C_6$alkoxy, $C_1$-$C_6$heteroalkyl, —O$R_7$, —N($R_7$)$_2$, —CN, —C(=O)R, —C(=O)O$R_7$, —C(=O)N($R_7$)$_2$, —N$R_7$C(=O)$R_8$, —N$R_7$SO$_2$$R_8$, —SO$_2$R, or —SO$_2$N($R_7$)$_2$;
each $R_6$ is independently hydrogen, $C_1$-$C_6$alkyl, or —$C_1$-$C_6$alkyl-Y—$R_9$;
each Y is independently —O—, —S—, or —N($R_{10}$)—;
each $R_7$ is independently hydrogen, $C_1$-$C_6$alkyl, $C_1$-$C_6$haloalkyl, or $C_1$-$C_6$heteroalkyl;
each $R_8$ is independently $C_1$-$C_6$alkyl or $C_1$-$C_6$heteroalkyl;
each $R_9$ is independently hydrogen or $C_1$-$C_6$alkyl;
each $R_{10}$ is independently hydrogen or $C_1$-$C_6$alkyl;
m is 0, 1, 2, 3, or 4;
n is 0, 1, 2, 3, or 4;
p is 0, 1, 2, 3, or 4; and
q is 0, 1, 2, or 3;
or a pharmaceutically acceptable salt or solvate thereof.

In some embodiments is a compound of Formula (I) wherein X is a bond. In some embodiments is a compound of Formula (I) wherein X is $C_1$-$C_6$alkyl. In some embodiments is a compound of Formula (I) wherein X is —CH$_2$—. In some embodiments is a compound of Formula (I) wherein X is $C_1$-$C_6$heteroalkyl.

In some embodiments is a compound of Formula (I) wherein $R_1$ is —C(=O)O$R_6$. In some embodiments is a compound of Formula (I) wherein $R_1$ is —C(=O)O$R_6$ and $R_6$ is hydrogen. In some embodiments is a compound of Formula (I) wherein $R_1$ is —C(=O)O$R_6$ and $R_6$ is $C_1$-$C_6$alkyl. In some embodiments is a compound of Formula (I) wherein $R_1$ is —C(=O)O$R_6$ and $R_6$ is —CH$_3$. In some embodiments is a compound of Formula (I) wherein $R_1$ is —C(=O)O$R_6$ and $R_6$ is —CH$_2$CH$_3$. In some embodiments is a compound of Formula (I) wherein $R_1$ is —C(=O)O$R_6$ and $R_6$ is —CH(CH$_3$)$_2$. In some embodiments is a compound of Formula (I) wherein $R_1$ is —C(=O)O$R_6$ and $R_6$ is —$C_1$-$C_6$alkyl-Y—$R_9$. In some embodiments is a compound of Formula (I) wherein $R_1$ is —C(=O)O$R_6$, $R_6$ is —$C_1$-$C_6$alkyl-Y—$R_9$, and Y is —O—. In some embodiments is a compound of Formula (I) wherein $R_1$ is —C(=O)O$R_6$, $R_6$ is —$C_1$-$C_6$alkyl-Y—$R_9$, and Y is —S—. In some embodiments is a compound of Formula (I) wherein $R_1$ is —C(=O)O$R_6$, $R_6$ is —$C_1$-$C_6$alkyl-Y—$R_9$, and Y is —N($R_{10}$)—. In some embodiments is a compound of Formula (I) wherein $R_1$ is —C(=O)O$R_6$, $R_6$ is —$C_1$-$C_6$alkyl-Y—$R_9$, and Y is —N(H)—. In some embodiments is a compound of Formula (I) wherein $R_9$ is hydrogen. In some embodiments is a compound of Formula (I) wherein $R_9$ is $C_1$-$C_6$alkyl. In some embodiments is a compound of Formula (I) wherein $R_9$ is —CH$_3$. In some embodiments is a compound of Formula (I) wherein $R_9$ is —CH$_2$CH$_3$. In some embodiments is a compound of Formula (I) wherein $R_9$ is —CH(CH$_3$)$_2$. In some embodiments is a compound of Formula (I) wherein $R_1$ is —C(=O)OCH$_2$CH$_2$OH. In some embodiments is a compound of Formula (I) wherein $R_1$ is —C(=O)OCH$_2$CH$_2$OCH$_3$. In some embodiments is a compound of Formula (I) wherein $R_1$ is —C(=O)OCH$_2$CH$_2$OCH$_2$CH$_3$. In some embodiments is a compound of Formula (I) wherein $R_1$ is —C(=O)OCH$_2$CH$_2$NH$_2$. In some embodiments is a compound of Formula (I) wherein $R_1$ is —C(=O)OCH$_2$CH$_2$N(H)CH$_3$. In some embodiments is a compound of Formula (I) wherein $R_1$ is —C(=O)OCH$_2$CH$_2$N(H)CH$_2$CH$_3$.

In some embodiments is a compound of Formula (I) wherein $R_1$ is —C(=O)N($R_6$)$_2$. In some embodiments is a compound of Formula (I) wherein $R_1$ is —C(=O)N($R_6$)$_2$ and each $R_6$ is hydrogen. In some embodiments is a compound of Formula (I) wherein $R_1$ is —C(=O)N($R_6$)$_2$, and one $R_6$ is hydrogen and one $R_6$ is $C_1$-$C_6$alkyl. In some embodiments is a compound of Formula (I) wherein $R_1$ is —C(=O)N($R_6$)$_2$, and one $R_6$ is hydrogen and one $R_6$ is —CH$_3$. In some embodiments is a compound of Formula (I) wherein $R_1$ is —C(=O)N($R_6$)$_2$, and one $R_6$ is hydrogen and one $R_6$ is —CH$_2$CH$_3$. In some embodiments is a compound of Formula (I) wherein $R_1$ is —C(=O)N($R_6$)$_2$, and one $R_6$ is hydrogen and one $R_6$ is —CH(CH$_3$)$_2$. In some embodiments is a compound of Formula (I) wherein $R_1$ is —C(=O)N($R_6$)$_2$ and each $R_6$ is —CH$_3$. In some embodiments is a compound of Formula (I) wherein $R_1$ is —C(=O)N($R_6$)$_2$ and each $R_6$ is —CH$_2$CH$_3$. In some embodiments is a compound of Formula (I) wherein $R_1$ is —C(=O)N($R_6$)$_2$, and one $R_6$ is hydrogen and $R_6$ is —$C_1$-$C_6$alkyl-Y—$R_9$. In some embodiments is a compound of Formula (I) wherein $R_1$ is —C(=O)N($R_6$)$_2$, one $R_6$ is hydrogen and one $R_6$ is —$C_1$-$C_6$alkyl-Y—$R_9$, and Y is —O—. In some embodiments is a compound of Formula (I) wherein $R_1$ is —C(=O)N($R_6$)$_2$, one $R_6$ is hydrogen and one $R_6$ is —$C_1$-$C_6$alkyl-Y—$R_9$, and Y is —S—. In some embodiments is a compound of Formula (I) wherein $R_1$ is —C(=O)N($R_6$)$_2$, one $R_6$ is hydrogen and one $R_6$ is —$C_1$-$C_6$alkyl-Y—$R_9$, and Y is —N($R_{10}$)—. In some embodiments is a compound of Formula (I) wherein $R_1$ is —C(=O)N($R_6$)$_2$, one $R_6$ is hydrogen and one $R_6$ is —$C_1$-$C_6$alkyl-Y—$R_9$, and Y is —N(H)—. In some embodiments is a compound of Formula (I) wherein $R_9$ is hydrogen. In some embodiments is a compound of Formula (I) wherein $R_9$ is $C_1$-$C_6$alkyl. In some embodiments is a compound of Formula (I) wherein $R_9$ is —$CH_3$. In some embodiments is a compound of Formula (I) wherein $R_9$ is —$CH_2CH_3$. In some embodiments is a compound of Formula (I) wherein $R_9$ is —$CH(CH_3)_2$. In some embodiments is a compound of Formula (I) wherein $R_1$ is —C(=O)N(H)$CH_2CH_2OH$. In some embodiments is a compound of Formula (I) wherein $R_1$ is —C(=O)N(H)$CH_2CH_2OCH_3$. In some embodiments is a compound of Formula (I) wherein $R_1$ is —C(=O)N(H)$CH_2CH_2OCH_2CH_3$. In some embodiments is a compound of Formula (I) wherein $R_1$ is —C(=O)N(H)$CH_2CH_2NH_2$. In some embodiments is a compound of Formula (I) wherein $R_1$ is —C(=O)N(H)$CH_2CH_2$N(H)$CH_3$. In some embodiments is a compound of Formula (I) wherein $R_1$ is —C(=O)N(H)$CH_2CH_2$N(H)$CH_2CH_3$.

In some embodiments is a compound of Formula (I) wherein —X—$R_1$ is —C(=O)OH. In some embodiments is a compound of Formula (I) wherein —X—$R_1$ is —C(=O)$OCH_3$. In some embodiments is a compound of Formula (I) wherein —X—$R_1$ is —C(=O)$OCH_2CH_3$. In some embodiments is a compound of Formula (I) wherein —X—$R_1$ is —C(=O)OCH$(CH_3)_2$. In some embodiments is a compound of Formula (I) wherein —X—$R_1$ is —C(=O)$OCH_2CH_2OH$. In some embodiments is a compound of Formula (I) wherein —X—$R_1$ is —C(=O)$OCH_2CH_2OCH_3$. In some embodiments is a compound of Formula (I) wherein —X—$R_1$ is —C(=O)$OCH_2CH_2OCH_2CH_3$. In some embodiments is a compound of Formula (I) wherein —X—$R_1$ is —C(=O)$OCH_2CH_2NH_2$. In some embodiments is a compound of Formula (I) wherein —X—$R_1$ is —$CH_2$C(=O)OH. In some embodiments is a compound of Formula (I) wherein —X—$R_1$ is —$CH_2$C(=O)$OCH_3$. In some embodiments is a compound of Formula (I) wherein —X—$R_1$ is —$CH_2$C(=O)$OCH_2CH_3$. In some embodiments is a compound of Formula (I) wherein —X—$R_1$ is —$CH_2$C(=O)OCH$(CH_3)_2$. In some embodiments is a compound of Formula (I) wherein —X—$R_1$ is —$CH_2$C(=O)$OCH_2CH_2OH$. In some embodiments is a compound of Formula (I) wherein —X—$R_1$ is —$CH_2$C(=O)$OCH_2CH_2OCH_3$. In some embodiments is a compound of Formula (I) wherein —X—$R_1$ is —$CH_2$C(=O)$OCH_2CH_2OCH_2CH_3$. In some embodiments is a compound of Formula (I) wherein —X—$R_1$ is —$CH_2$C(=O)$OCH_2CH_2NH_2$.

In some embodiments is a compound of Formula (I) wherein —X—$R_1$ is —C(=O)N(H)$CH_3$. In some embodiments is a compound of Formula (I) wherein —X—$R_1$ is —C(=O)N(H)$CH_2CH_3$. In some embodiments is a compound of Formula (I) wherein —X—$R_1$ is —C(=O)N(H)CH$(CH_3)_2$. In some embodiments is a compound of Formula (I) wherein —X—$R_1$ is —C(=O)N(H)$CH_2CH_2OH$. In some embodiments is a compound of Formula (I) wherein —X—$R_1$ is —C(=O)N(H)$CH_2CH_2OCH_3$. In some embodiments is a compound of Formula (I) wherein —X—$R_1$ is —C(=O)N(H)$CH_2CH_2OCH_2CH_3$. In some embodiments is a compound of Formula (I) wherein —X—$R_1$ is —C(=O)N(H)$CH_2CH_2NH_2$. In some embodiments is a compound of Formula (I) wherein —X—$R_1$ is —$CH_2$C(=O)N(H)$CH_3$. In some embodiments is a compound of Formula (I) wherein —X—$R_1$ is —$CH_2$C(=O)N(H)$CH_2CH_3$. In some embodiments is a compound of Formula (I) wherein —X—$R_1$ is —$CH_2$C(=O)N(H)CH$(CH_3)_2$. In some embodiments is a compound of Formula (I) wherein —X—$R_1$ is —$CH_2$C(=O)N(H)$CH_2CH_2OH$. In some embodiments is a compound of Formula (I) wherein —X—$R_1$ is —$CH_2$C(=O)N(H)$CH_2CH_2OCH_3$. In some embodiments is a compound of Formula (I) wherein —X—$R_1$ is —$CH_2$C(=O)N(H)$CH_2CH_2OCH_2CH_3$. In some embodiments is a compound of Formula (I) wherein —X—$R_1$ is —$CH_2$C(=O)N(H)$CH_2CH_2NH_2$.

In some embodiments is a compound of Formula (I) wherein m is 0, 1, 2, or 3. In some embodiments is a compound of Formula (I) wherein m is 0, 1, or 2. In some embodiments is a compound of Formula (I) wherein m is 0 or 1. In some embodiments is a compound of Formula (I) wherein m is 0. In some embodiments is a compound of Formula (I) wherein m is 1. In some embodiments is a compound of Formula (I) wherein m is 2. In some embodiments is a compound of Formula (I) wherein m is 3. In some embodiments is a compound of Formula (I) wherein m is 4. In some embodiments is a compound of Formula (I) wherein m is 1, 2, or 3 and each $R_2$ is independently halogen, $C_1$-$C_6$alkyl, or $C_1$-$C_6$alkoxy. In some embodiments is a compound of Formula (I) wherein m is 1 or 2 and each $R_2$ is independently halogen, $C_1$-$C_6$alkyl, or $C_1$-$C_6$alkoxy. In some embodiments is a compound of Formula (I) wherein m is 1 and $R_2$ is halogen, $C_1$-$C_6$alkyl, or $C_1$-$C_6$alkoxy. In some embodiments is a compound of Formula (I) wherein m is 1 and $R_2$ is halogen. In some embodiments is a compound of Formula (I) wherein m is 1 and $R_2$ is —Cl. In some embodiments is a compound of Formula (I) wherein m is 1 and $R_2$ is $C_1$-$C_6$alkyl. In some embodiments is a compound of Formula (I) wherein m is 1 and $R_2$ is —$CH_3$. In some embodiments is a compound of Formula (I) wherein m is 1 and $R_2$ is $C_1$-$C_6$alkoxy. In some embodiments is a compound of Formula (I) wherein m is 1 and $R_2$ is —$OCH_3$.

In some embodiments is a compound of Formula (I) wherein n is 0, 1, 2, or 3. In some embodiments is a compound of Formula (I) wherein n is 0, 1, or 2. In some embodiments is a compound of Formula (I) wherein n is 0 or 1. In some embodiments is a compound of Formula (I) wherein n is 0. In some embodiments is a compound of Formula (I) wherein n is 1. In some embodiments is a compound of Formula (I) wherein n is 2. In some embodiments is a compound of Formula (I) wherein n is 3. In some embodiments is a compound of Formula (I) wherein n is 4. In some embodiments is a compound of Formula (I) wherein n is 1, 2, or 3 and each $R_3$ is independently halogen, $C_1$-$C_6$alkyl, $C_1$-$C_6$haloalkyl, or $C_1$-$C_6$alkoxy. In some embodiments is a compound of Formula (I) wherein n is 1 or 2 and each $R_3$ is independently halogen, $C_1$-$C_6$alkyl, $C_1$-$C_6$haloalkyl, or $C_1$-$C_6$alkoxy. In some embodiments is a compound of Formula (I) wherein n is 1 and $R_3$ is halogen, $C_1$-$C_6$alkyl, $C_1$-$C_6$haloalkyl, or $C_1$-$C_6$alkoxy. In some embodiments is a compound of Formula (I) wherein n is 1 and $R_3$ is halogen. In some embodiments is a compound of Formula (I) wherein n is 1 and $R_3$ is —F. In some embodiments is a compound of Formula (I) wherein n is 1 and $R_3$ is —Cl. In some embodiments is a compound of Formula (I) wherein n is 1 and $R_3$ is $C_1$-$C_6$alkyl. In some embodiments is a compound of Formula (I) wherein n is 1 and $R_3$ is —$CH_3$. In some embodiments is a compound of Formula (I) wherein n is 1 and $R_3$ is $C_1$-$C_6$haloalkyl. In some embodiments is a compound of Formula (I) wherein n is 1 and $R_3$ is —$CF_3$. In some embodiments is a compound of Formula (I) wherein n is 1 and $R_3$ is $C_1$-$C_6$alkoxy. In some embodiments is a compound of Formula (I) wherein n is 1 and $R_3$ is —$OCH_3$.

In some embodiments is a compound of Formula (I) wherein p is 0, 1, 2, or 3. In some embodiments is a compound of Formula (I) wherein p is 0, 1, or 2. In some embodiments is a compound of Formula (I) wherein p is 0 or 1. In some embodiments is a compound of Formula (I) wherein p is 0. In some embodiments is a compound of Formula (I) wherein p is 1. In some embodiments is a compound of Formula (I) wherein p is 2. In some embodiments is a compound of Formula (I) wherein p is 3. In some embodiments is a compound of Formula (I) wherein p is 4. In some embodiments is a compound of Formula (I) wherein p is 1, 2, or 3 and each $R_4$ is independently halogen, $C_1$-$C_6$alkyl, $C_1$-$C_6$haloalkyl, or $C_1$-$C_6$alkoxy. In some embodiments is a compound of Formula (I) wherein p is 1 or 2 and each $R_4$ is independently halogen, $C_1$-$C_6$alkyl, $C_1$-$C_6$haloalkyl, or $C_1$-$C_6$alkoxy. In some embodiments is a compound of Formula (I) wherein p is 1 and $R_4$ is halogen, $C_1$-$C_6$alkyl, $C_1$-$C_6$haloalkyl, or $C_1$-$C_6$alkoxy. In some embodiments is a compound of Formula (I) wherein p is 1 and $R_4$ is halogen. In some embodiments is a compound of Formula (I) wherein p is 1 and $R_4$ is —F. In some embodiments is a compound of Formula (I) wherein p is 1 and $R_4$ is —Cl. In some embodiments is a compound of Formula (I) wherein p is 1 and $R_4$ is $C_1$-$C_6$alkyl. In some embodiments is a compound of Formula (I) wherein p is 1 and $R_4$ is —$CH_3$. In some embodiments is a compound of Formula (I) wherein p is 1 and $R_4$ is $C_1$-$C_6$haloalkyl. In some embodiments is a compound of Formula (I) wherein p is 1 and $R_4$ is —$CF_3$. In some embodiments is a compound of Formula (I) wherein p is 1 and $R_4$ is $C_1$-$C_6$alkoxy. In some embodiments is a compound of Formula (I) wherein p is 1 and $R_4$ is —$OCH_3$.

In some embodiments is a compound of Formula (I) wherein q is 0, 1, or 2. In some embodiments is a compound of Formula (I) wherein q is 0 or 1. In some embodiments is a compound of Formula (I) wherein q is 0. In some embodiments is a compound of Formula (I) wherein q is 1. In some embodiments is a compound of Formula (I) wherein q is 2. In some embodiments is a compound of Formula (I) wherein q is 3. In some embodiments is a compound of Formula (I) wherein q is 1, 2, or 3 and each $R_5$ is independently halogen, $C_1$-$C_6$alkyl, $C_1$-$C_6$haloalkyl, or $C_1$-$C_6$alkoxy. In some embodiments is a compound of Formula (I) wherein q is 1 or 2 and each $R_5$ is independently halogen, $C_1$-$C_6$alkyl, $C_1$-$C_6$haloalkyl, or $C_1$-$C_6$alkoxy. In some embodiments is a compound of Formula (I) wherein q is 1 and $R_5$ is halogen, $C_1$-$C_6$alkyl, $C_1$-$C_6$haloalkyl, or $C_1$-$C_6$alkoxy. In some embodiments is a compound of Formula (I) wherein q is 1 and $R_5$ is halogen. In some embodiments is a compound of Formula (I) wherein q is 1 and $R_5$ is —F. In some embodiments is a compound of Formula (I) wherein q is 1 and $R_5$ is —Cl. In some embodiments is a compound of Formula (I) wherein q is 1 and $R_5$ is $C_1$-$C_6$alkyl. In some embodiments is a compound of Formula (I) wherein q is 1 and $R_5$ is —$CH_3$. In some embodiments is a compound of Formula (I) wherein q is 1 and $R_5$ is $C_1$-$C_6$haloalkyl. In some embodiments is a compound of Formula (I) wherein q is 1 and $R_5$ is —$CF_3$. In some embodiments is a compound of Formula (I) wherein q is 1 and $R_5$ is $C_1$-$C_6$alkoxy. In some embodiments is a compound of Formula (I) wherein q is 1 and $R_5$ is —$OCH_3$.

In some embodiments is a compound of Formula (I) wherein m is 0 or 1, n is 0 or 1, p is 0 or 1, and q is 0 or 1. In some embodiments is a compound of Formula (I) wherein m is 0, n is 0, p is 0, and q is 0. In some embodiments is a compound of Formula (I) wherein m is 1, n is 0, p is 0, q is 0 and $R_2$ is halogen, $C_1$-$C_6$alkyl, or $C_1$-$C_6$alkoxy. In some embodiments is a compound of Formula (I) wherein m is 0, n is 1, p is 0, q is 0, and $R_3$ is halogen, $C_1$-$C_6$alkyl, $C_1$-$C_6$haloalkyl, or $C_1$-$C_6$alkoxy. In some embodiments is a compound of Formula (I) wherein m is 0, n is 0, p is 1, q is 0 and $R_4$ is halogen, $C_1$-$C_6$alkyl, $C_1$-$C_6$haloalkyl, or $C_1$-$C_6$alkoxy. In some embodiments is a compound of Formula (I) wherein m is 0, n is 0, p is 0, q is 1, and $R_5$ is halogen, $C_1$-$C_6$alkyl, $C_1$-$C_6$haloalkyl, or $C_1$-$C_6$alkoxy.

In another embodiment is a compound of Formula (I) wherein (A)

is phenyl, or a 5-membered or 6-membered heteroaryl ring. In another embodiment is a compound of Formula (I) wherein (A)

is phenyl or a 5-membered heteroaryl ring. In another embodiment is a compound of Formula (I) wherein (A)

is phenyl or a 6-membered heteroaryl ring. In another embodiment is a compound of Formula (I) wherein (A)

is a 5-membered or 6-membered heteroaryl ring. In another embodiment is a compound of Formula (I) wherein (A)

is phenyl. In another embodiment is a compound of Formula (I) wherein (A)

is a 6-membered heteroaryl ring. In another embodiment is a compound of Formula (I) wherein (A)

is pyridyl. In another embodiment is a compound of Formula (I) wherein (A)

is pyrimidyl. In another embodiment is a compound of Formula (I) wherein (A)

is pyrazinyl. In another embodiment is a compound of Formula (I) wherein (A)

is pyridizinyl. In another embodiment is a compound of Formula (I) wherein (A)

is a 5-membered ring. In another embodiment is a compound of Formula (I) wherein (A)

is pyrazolyl. In another embodiment is a compound of Formula (I) wherein (A)

is pyrrolyl. In another embodiment is a compound of Formula (I) wherein (A)

is imidazolyl. In another embodiment is a compound of Formula (I) wherein (A)

is oxazolyl. In another embodiment is a compound of Formula (I) wherein (A)

is thiazolyl. In another embodiment is a compound of Formula (I) wherein (A)

is thiophenyl.

In another embodiment is a compound of Formula (I) wherein (B)

is phenyl, or a 5-membered or 6-membered heteroaryl ring. In another embodiment is a compound of Formula (I) wherein (B)

is phenyl or a 5-membered heteroaryl ring. In another embodiment is a compound of Formula (I) wherein (B)

is phenyl or a 6-membered heteroaryl ring. In another embodiment is a compound of Formula (I) wherein (B)

is a 5-membered or 6-membered heteroaryl ring. In another embodiment is a compound of Formula (I) wherein (B)

is phenyl. In another embodiment is a compound of Formula (I) wherein (B)

is a 6-membered heteroaryl ring. In another embodiment is a compound of Formula (I) wherein (B)

is pyridyl. In another embodiment is a compound of Formula (I) wherein (B)

is pyrimidyl. In another embodiment is a compound of Formula (I) wherein (B)

is pyrazinyl. In another embodiment is a compound of Formula (I) wherein (B)

is pyridizinyl. In another embodiment is a compound of Formula (I) wherein (B)

is a 5-membered ring. In another embodiment is a compound of Formula (I) wherein (B)

is pyrazolyl. In another embodiment is a compound of Formula (I) wherein (B)

is pyrrolyl. In another embodiment is a compound of Formula (I) wherein (B)

is imidazolyl. In another embodiment is a compound of Formula (I) wherein (B)

is oxazolyl. In another embodiment is a compound of Formula (I) wherein (B)

is thiazolyl. In another embodiment is a compound of Formula (I) wherein is (B)

is thiophenyl.

In another embodiment is a compound of Formula (I) wherein (C)

is phenyl, or a 5-membered or 6-membered heteroaryl ring. In another embodiment is a compound of Formula (I) wherein (C)

is phenyl or a 5-membered heteroaryl ring. In another embodiment is a compound of Formula (I) wherein (C)

is phenyl or a 6-membered heteroaryl ring. In another embodiment is a compound of Formula (I) wherein (C)

is a 5-membered or 6-membered heteroaryl ring. In another embodiment is a compound of Formula (I) wherein (C)

is phenyl. In another embodiment is a compound of Formula (I) wherein (C)

is a 6-membered heteroaryl ring. In another embodiment is a compound of Formula (I) wherein (C)

is pyridyl. In another embodiment is a compound of Formula (I) wherein (C)

is pyrimidyl. In another embodiment is a compound of Formula (I) wherein

is pyrazinyl. In another embodiment is a compound of Formula (I) wherein

is pyridizinyl. In another embodiment is a compound of Formula (I) wherein

is a 5-membered ring. In another embodiment is a compound of Formula (I) wherein

is pyrazolyl. In another embodiment is a compound of Formula (I) wherein

is pyrrolyl. In another embodiment is a compound of Formula (I) wherein

is imidazolyl. In another embodiment is a compound of Formula (I) wherein

is oxazolyl. In another embodiment is a compound of Formula (I) wherein

is thiazolyl. In another embodiment is a compound of Formula (I) wherein

is thiophenyl.

In another embodiment is a compound of Formula (I) wherein

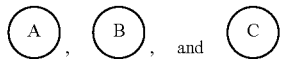

are phenyl. In another embodiment is a compound of Formula (I) wherein

is a 6-membered heteroaryl ring, and

are phenyl. In another embodiment is a compound of Formula (I) wherein

is pyridyl, and

are phenyl. In another embodiment is a compound of Formula (I) wherein

is a 6-membered heteroaryl ring, and

are phenyl. In another embodiment is a compound of Formula (I) wherein

is pyridyl, and

are phenyl. In another embodiment is a compound of Formula (I) wherein

is a 6-membered heteroaryl ring, and

are phenyl. In another embodiment is a compound of Formula (I) wherein

is pyridyl, and

are phenyl. In another embodiment is a compound of Formula (I) wherein

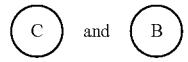

are a 6-membered heteroaryl ring, and

is phenyl. In another embodiment is a compound of Formula (I) wherein

are pyridyl, and

is phenyl. In another embodiment is a compound of Formula (I) wherein

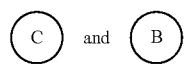

are a 6-membered heteroaryl ring, and

is phenyl. In another embodiment is a compound of Formula (I) wherein

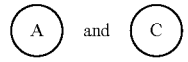

are pyridyl, and

is phenyl. In another embodiment is a compound of Formula (I) wherein

are a 6-membered heteroaryl ring, and

is phenyl. In another embodiment is a compound of Formula (I) wherein

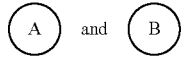

are pyridyl, and

is phenyl. In another embodiment is a compound of Formula (I) wherein

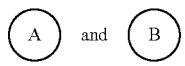, , and 

are a 6-membered heteroaryl ring. In another embodiment is a compound of Formula (I) wherein

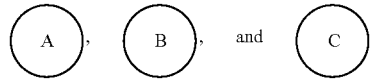, 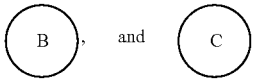, and 

are pyridyl. In another embodiment is a compound of Formula (I) wherein

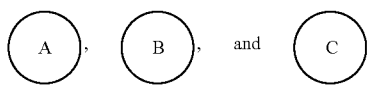

is phenyl, or a 5-membered or 6-membered heteroaryl ring.

In another aspect is a compound of Formula (Ia):

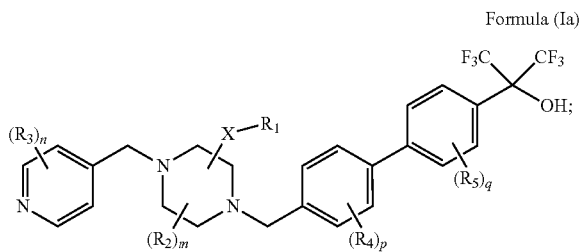

Formula (Ia)

wherein:
X is a bond, $C_1$-$C_6$alkyl, or $C_1$-$C_6$heteroalkyl;
$R_1$ is —C(=O)O$R_6$ or —C(=O)N($R_6$)$_2$;
each $R_2$ is independently halogen, $C_1$-$C_6$alkyl, or $C_1$-$C_6$alkoxy;
each $R_3$, each $R_4$, and each $R_5$ are each independently halogen, $C_1$-$C_6$alkyl, $C_1$-$C_6$haloalkyl, $C_1$-$C_6$alkoxy, $C_1$-$C_6$heteroalkyl, —O$R_7$, —N($R_7$)$_2$, —CN, —C(=O)R, —C(=O)O$R_7$, —C(=O)N($R_7$)$_2$, —N$R_7$C(=O)$R_8$, —N$R_7$SO$_2R_8$, —SO$_2R_8$, or —SO$_2$N($R_7$)$_2$;
each $R_6$ is independently hydrogen, $C_1$-$C_6$alkyl, or —$C_1$-$C_6$alkyl-Y—$R_9$;
each Y is independently —O—, —S—, or —N($R_{10}$)—;
each $R_7$ is independently hydrogen, $C_1$-$C_6$alkyl, $C_1$-$C_6$haloalkyl, or $C_1$-$C_6$heteroalkyl;
each $R_8$ is independently $C_1$-$C_6$alkyl or $C_1$-$C_6$heteroalkyl;
each $R_9$ is independently hydrogen or $C_1$-$C_6$alkyl;
each $R_{10}$ is independently hydrogen or $C_1$-$C_6$alkyl;
m is 0, 1, 2, 3, or 4;
n is 0, 1, 2, 3, or 4;
p is 0, 1, 2, 3, or 4; and
q is 0, 1, 2, or 3;
or a pharmaceutically acceptable salt or solvate thereof.

In some embodiments is a compound of Formula (Ia) wherein X is a bond. In some embodiments is a compound of Formula (Ia) wherein X is $C_1$-$C_6$alkyl. In some embodiments is a compound of Formula (Ia) wherein X is —CH$_2$—. In some embodiments is a compound of Formula (Ia) wherein X is $C_1$-$C_6$heteroalkyl.

In some embodiments is a compound of Formula (Ia) wherein $R_1$ is —C(=O)O$R_6$. In some embodiments is a compound of Formula (Ia) wherein $R_1$ is —C(=O)O$R_6$ and $R_6$ is hydrogen. In some embodiments is a compound of Formula (Ia) wherein $R_1$ is —C(=O)O$R_6$ and $R_6$ is $C_1$-$C_6$alkyl or —$C_1$-$C_6$alkyl-Y—$R_9$. In some embodiments is a compound of Formula (Ia) wherein $R_1$ is —C(=O)O$R_6$ and $R_6$ is $C_1$-$C_6$alkyl. In some embodiments is a compound of Formula (Ia) wherein $R_1$ is —C(=O)O$R_6$ and $R_6$ is —CH$_3$, —CH$_2$CH$_3$, or —CH(CH$_3$)$_2$. In some embodiments is a compound of Formula (Ia) wherein $R_1$ is —C(=O)O$R_6$ and $R_6$ is —CH$_3$. In some embodiments is a compound of Formula (Ia) wherein $R_1$ is —C(=O)O$R_6$ and $R_6$ is —CH$_2$CH$_3$. In some embodiments is a compound of Formula (Ia) wherein $R_1$ is —C(=O)O$R_6$ and $R_6$ is —CH(CH$_3$)$_2$. In some embodiments is a compound of Formula (Ia) wherein $R_1$ is —C(=O)O$R_6$, $R_6$ is $C_1$-$C_6$alkyl or —$C_1$-$C_6$alkyl-Y—$R_9$, Y is —O—, and $R_9$ is hydrogen or $C_1$-$C_6$alkyl. In some embodiments is a compound of Formula (Ia) wherein $R_1$ is —C(=O)O$R_6$ and $R_6$ is —$C_1$-$C_6$alkyl-Y—$R_9$. In some embodiments is a compound of Formula (Ia) wherein $R_1$ is —C(=O)O$R_6$, $R_6$ is —$C_1$-$C_6$alkyl-Y—$R_9$, and Y is —O—. In some embodiments is a compound of Formula (Ia) wherein $R_1$ is —C(=O)O$R_6$, $R_6$ is —$C_1$-$C_6$alkyl-Y—$R_9$, and Y is —O—, and $R_9$ is hydrogen. In some embodiments is a compound of Formula (Ia) wherein $R_1$ is —C(=O)O$R_6$, $R_6$ is —$C_1$-$C_6$alkyl-Y—$R_9$, and Y is —O—, and $R_9$ is $C_1$-$C_6$alkyl. In some embodiments is a compound of Formula (Ia) wherein $R_1$ is —C(=O)O$R_6$, $R_6$ is —$C_1$-$C_6$alkyl-Y—$R_9$, and Y is —S—. In some embodiments is a compound of Formula (Ia) wherein $R_1$ is —C(=O)O$R_6$, $R_6$ is —$C_1$-$C_6$alkyl-Y—$R_9$, and Y is —N($R_{10}$)—. In some embodiments is a compound of Formula (Ia) wherein $R_1$ is —C(=O)O$R_6$, $R_6$ is —$C_1$-$C_6$alkyl-Y—$R_9$, and Y is —N(H)—. In some embodiments is a compound of Formula (Ia) wherein $R_9$ is hydrogen. In some embodiments is a compound of Formula (Ia) wherein $R_9$ is $C_1$-$C_6$alkyl. In some embodiments is a compound of Formula (Ia) wherein $R_9$ is —CH$_3$. In some embodiments is a compound of Formula (Ia) wherein $R_9$ is —CH$_2$CH$_3$. In some embodiments is a compound of Formula (Ia) wherein $R_9$ is —CH(CH$_3$)$_2$. In some embodiments is a compound of Formula (Ia) wherein $R_1$ is —C(=O)OCH$_2$CH$_2$OH. In some embodiments is a compound of Formula (Ia) wherein $R_1$ is —C(=O)OCH$_2$CH$_2$OCH$_3$. In some embodiments is a compound of Formula (Ia) wherein $R_1$ is —C(=O)OCH$_2$CH$_2$OCH$_2$CH$_3$. In some embodiments is a compound of Formula (Ia) wherein $R_1$ is —C(=O)OCH$_2$CH$_2$NH$_2$. In some embodiments is a compound of Formula (Ia) wherein $R_1$ is —C(=O)OCH$_2$CH$_2$N(H)CH$_3$. In some embodiments is a compound of Formula (Ia) wherein $R_1$ is —C(=O)OCH$_2$CH$_2$N(H)CH$_2$CH$_3$.

In some embodiments is a compound of Formula (Ia) wherein $R_1$ is —C(=O)N($R_6$)$_2$. In some embodiments is a compound of Formula (Ia) wherein $R_1$ is —C(=O)N($R_6$)$_2$ and each $R_6$ is hydrogen. In some embodiments is a compound of Formula (Ia) wherein $R_1$ is —C(=O)N($R_6$)$_2$, and one $R_6$ is hydrogen and one $R_6$ is $C_1$-$C_6$alkyl. In some embodiments is a compound of Formula (Ia) wherein $R_1$ is —C(=O)N($R_6$)$_2$, and one $R_6$ is hydrogen and one $R_6$ is —CH$_3$. In some embodiments is a compound of Formula (Ia) wherein $R_1$ is —C(=O)N($R_6$)$_2$, and one $R_6$ is hydrogen and one $R_6$ is —CH$_2$CH$_3$. In some embodiments is a compound of Formula (Ia) wherein $R_1$ is —C(=O)N($R_6$)$_2$, and one $R_6$ is hydrogen and one $R_6$ is —CH(CH$_3$)$_2$. In some embodiments is a compound of Formula (Ia) wherein $R_1$ is —C(=O)N($R_6$)$_2$ and each $R_6$ is —CH$_3$. In some embodiments is a compound of Formula (Ia) wherein $R_1$ is —C(=O)N($R_6$)$_2$ and each $R_6$ is —CH$_2$CH$_3$. In some embodiments is a compound of Formula (Ia) wherein $R_1$ is —C(=O)N($R_6$)$_2$, and one $R_6$ is hydrogen and $R_6$ is —$C_1$-$C_6$alkyl-Y—$R_9$. In some embodiments is a compound of Formula (Ia) wherein $R_1$ is —C(=O)N($R_6$)$_2$, one $R_6$ is hydrogen and one $R_6$ is —$C_1$-$C_6$alkyl-Y—$R_9$, and Y is —O—. In some embodiments is a compound of Formula (Ia) wherein $R_1$ is —C(=O)N($R_6$)$_2$, one $R_6$ is hydrogen and one $R_6$ is —$C_1$-$C_6$alkyl-Y—$R_9$, and Y is —S—. In some embodiments is a compound of Formula (Ia) wherein $R_1$ is —C(=O)N($R_6$)$_2$, one $R_6$ is hydrogen and one $R_6$ is —$C_1$-$C_6$alkyl-Y—$R_9$, and Y is —N($R_{10}$)—. In some embodiments is a compound of Formula (Ia) wherein $R_1$ is —C(=O)N($R_6$)$_2$, one $R_6$ is hydrogen and one $R_6$ is —$C_1$-$C_6$alkyl-Y—$R_9$, and Y is —N(H)—. In some embodiments is a compound of Formula (Ia) wherein $R_9$ is hydrogen. In some embodiments is a compound of Formula (Ia) wherein $R_9$ is $C_1$-$C_6$alkyl. In some embodiments is a compound of Formula (Ia) wherein $R_9$ is —$CH_3$. In some embodiments is a compound of Formula (Ia) wherein $R_9$ is —$CH_2CH_3$. In some embodiments is a compound of Formula (Ia) wherein $R_9$ is —$CH(CH_3)_2$. In some embodiments is a compound of Formula (Ia) wherein $R_1$ is —C(=O)N(H)$CH_2CH_2$OH. In some embodiments is a compound of Formula (Ia) wherein $R_1$ is —C(=O)N(H)$CH_2CH_2OCH_3$. In some embodiments is a compound of Formula (Ia) wherein $R_1$ is —C(=O)N(H)$CH_2CH_2OCH_2CH_3$. In some embodiments is a compound of Formula (Ia) wherein $R_1$ is —C(=O)N(H)$CH_2CH_2NH_2$. In some embodiments is a compound of Formula (Ia) wherein $R_1$ is —C(=O)N(H)$CH_2CH_2$N(H)$CH_3$. In some embodiments is a compound of Formula (Ia) wherein $R_1$ is —C(=O)N(H)$CH_2CH_2$N(H)$CH_2CH_3$.

In some embodiments is a compound of Formula (Ia) wherein —X—$R_1$ is —C(=O)OH. In some embodiments is a compound of Formula (Ia) wherein —X—$R_1$ is —C(=O)$OCH_3$. In some embodiments is a compound of Formula (Ia) wherein —X—$R_1$ is —C(=O)$OCH_2CH_3$. In some embodiments is a compound of Formula (Ia) wherein —X—$R_1$ is —C(=O)$OCH(CH_3)_2$. In some embodiments is a compound of Formula (Ia) wherein —X—$R_1$ is —C(=O)$OCH_2CH_2$OH. In some embodiments is a compound of Formula (Ia) wherein —X—$R_1$ is —C(=O)$OCH_2CH_2OCH_3$. In some embodiments is a compound of Formula (Ia) wherein —X—$R_1$ is —C(=O)$OCH_2CH_2OCH_2CH_3$. In some embodiments is a compound of Formula (Ia) wherein —X—$R_1$ is —C(=O)$OCH_2CH_2NH_2$. In some embodiments is a compound of Formula (Ia) wherein —X—$R_1$ is —$CH_2$C(=O)OH. In some embodiments is a compound of Formula (Ia) wherein —X—$R_1$ is —$CH_2$C(=O)$OCH_3$. In some embodiments is a compound of Formula (Ia) wherein —X—$R_1$ is —$CH_2$C(=O)$OCH_2CH_3$. In some embodiments is a compound of Formula (Ia) wherein —X—$R_1$ is —$CH_2$C(=O)$OCH(CH_3)_2$. In some embodiments is a compound of Formula (Ia) wherein —X—$R_1$ is —$CH_2$C(=O)$OCH_2CH_2$OH. In some embodiments is a compound of Formula (Ia) wherein —X—$R_1$ is —$CH_2$C(=O)$OCH_2CH_2OCH_3$. In some embodiments is a compound of Formula (Ia) wherein —X—$R_1$ is —$CH_2$C(=O)$OCH_2CH_2OCH_2CH_3$. In some embodiments is a compound of Formula (Ia) wherein —X—$R_1$ is —$CH_2$C(=O)$OCH_2CH_2NH_2$.

In some embodiments is a compound of Formula (Ia) wherein —X—$R_1$ is —C(=O)N(H)$CH_3$. In some embodiments is a compound of Formula (Ia) wherein —X—$R_1$ is —C(=O)N(H)$CH_2CH_3$. In some embodiments is a compound of Formula (Ia) wherein —X—$R_1$ is —C(=O)N(H)$CH(CH_3)_2$. In some embodiments is a compound of Formula (Ia) wherein —X—$R_1$ is —C(=O)N(H)$CH_2CH_2$OH. In some embodiments is a compound of Formula (Ia) wherein —X—$R_1$ is —C(=O)N(H)$CH_2CH_2OCH_3$. In some embodiments is a compound of Formula (Ia) wherein —X—$R_1$ is —C(=O)N(H)$CH_2CH_2OCH_2CH_3$. In some embodiments is a compound of Formula (Ia) wherein —X—$R_1$ is —C(=O)N(H)$CH_2CH_2NH_2$. In some embodiments is a compound of Formula (Ia) wherein —X—$R_1$ is —$CH_2$C(=O)N(H)$CH_3$. In some embodiments is a compound of Formula (Ia) wherein —X—$R_1$ is —$CH_2$C(=O)N(H)$CH_2CH_3$. In some embodiments is a compound of Formula (Ia) wherein —X—$R_1$ is —$CH_2$C(=O)N(H)$CH(CH_3)_2$. In some embodiments is a compound of Formula (Ia) wherein —X—$R_1$ is —$CH_2$C(=O)N(H)$CH_2CH_2$OH. In some embodiments is a compound of Formula (Ia) wherein —X—$R_1$ is —$CH_2$C(=O)N(H)$CH_2CH_2OCH_3$. In some embodiments is a compound of Formula (Ia) wherein —X—$R_1$ is —$CH_2$C(=O)N(H)$CH_2CH_2OCH_2CH_3$. In some embodiments is a compound of Formula (Ia) wherein —X—$R_1$ is —$CH_2$C(=O)N(H)$CH_2CH_2NH_2$.

In some embodiments is a compound of Formula (Ia) wherein m is 0, 1, 2, or 3. In some embodiments is a compound of Formula (Ia) wherein m is 0, 1, or 2. In some embodiments is a compound of Formula (Ia) wherein m is 0 or 1. In some embodiments is a compound of Formula (Ia) wherein m is 0. In some embodiments is a compound of Formula (Ia) wherein m is 1. In some embodiments is a compound of Formula (Ia) wherein m is 2. In some embodiments is a compound of Formula (Ia) wherein m is 3. In some embodiments is a compound of Formula (Ia) wherein m is 4. In some embodiments is a compound of Formula (Ia) wherein m is 1, 2, or 3 and each $R_2$ is independently halogen, $C_1$-$C_6$alkyl, or $C_1$-$C_6$alkoxy. In some embodiments is a compound of Formula (Ia) wherein m is 1 or 2 and each $R_2$ is independently halogen, $C_1$-$C_6$alkyl, or $C_1$-$C_6$alkoxy. In some embodiments is a compound of Formula (Ia) wherein m is 1 and $R_2$ is halogen, $C_1$-$C_6$alkyl, or $C_1$-$C_6$alkoxy. In some embodiments is a compound of Formula (Ia) wherein m is 1 and $R_2$ is halogen. In some embodiments is a compound of Formula (Ia) wherein m is 1 and $R_2$ is —Cl. In some embodiments is a compound of Formula (Ia) wherein m is 1 and $R_2$ is $C_1$-$C_6$alkyl. In some embodiments is a compound of Formula (Ia) wherein m is 1 and $R_2$ is —$CH_3$. In some embodiments is a compound of Formula (Ia) wherein m is 1 and $R_2$ is $C_1$-$C_6$alkoxy. In some embodiments is a compound of Formula (Ia) wherein m is 1 and $R_2$ is —$OCH_3$.

In some embodiments is a compound of Formula (Ia) wherein n is 0, 1, 2, or 3. In some embodiments is a compound of Formula (Ia) wherein n is 0, 1, or 2. In some embodiments is a compound of Formula (Ia) wherein n is 0 or 1. In some embodiments is a compound of Formula (Ia) wherein n is 0. In some embodiments is a compound of Formula (Ia) wherein n is 1. In some embodiments is a compound of Formula (Ia) wherein n is 2. In some embodiments is a compound of Formula (Ia) wherein n is 3. In some embodiments is a compound of Formula (Ia) wherein n is 4. In some embodiments is a compound of Formula (Ia) wherein n is 1, 2, or 3 and each $R_3$ is independently halogen, $C_1$-$C_6$alkyl, $C_1$-$C_6$haloalkyl, or $C_1$-$C_6$alkoxy. In some embodiments is a compound of Formula (Ia) wherein n is 1 or 2 and each $R_3$ is independently halogen, $C_1$-$C_6$alkyl, $C_1$-$C_6$haloalkyl, or $C_1$-$C_6$alkoxy. In some embodiments is a compound of Formula (Ia) wherein n is 1 and $R_3$ is halogen, $C_1$-$C_6$alkyl, $C_1$-$C_6$haloalkyl, or $C_1$-$C_6$alkoxy. In some embodiments is a compound of Formula (Ia) wherein n is 1 and $R_3$ is halogen. In some embodiments is a compound of Formula (Ia) wherein n is 1 and $R_3$ is —F. In some embodiments is a compound of Formula (Ia) wherein n is 1 and $R_3$ is —Cl. In some embodiments is a compound of Formula (Ia) wherein n is 1 and $R_3$ is $C_1$-$C_6$alkyl. In some embodiments is a compound of Formula (Ia) wherein n is 1 and $R_3$ is —$CH_3$. In some embodiments is a compound of Formula (Ia) wherein n is 1 and $R_3$ is $C_1$-$C_6$haloalkyl. In some embodiments is a compound of Formula (Ia) wherein n is 1 and $R_3$ is —$CF_3$. In some embodiments is a compound of Formula (Ia) wherein n is 1 and $R_3$ is $C_1$-$C_6$alkoxy. In some embodiments is a compound of Formula (Ia) wherein n is 1 and $R_3$ is —$OCH_3$.

In some embodiments is a compound of Formula (Ia) wherein p is 0, 1, 2, or 3. In some embodiments is a compound of Formula (Ia) wherein p is 0, 1, or 2. In some embodiments is a compound of Formula (Ia) wherein p is 0 or 1. In some embodiments is a compound of Formula (Ia) wherein p is 0. In some embodiments is a compound of Formula (Ia) wherein p is 1. In some embodiments is a compound of Formula (Ia) wherein p is 2. In some embodiments is a compound of Formula (Ia) wherein p is 3. In some embodiments is a compound of Formula (Ia) wherein p is 4. In some embodiments is a compound of Formula (Ia) wherein p is 1, 2, or 3 and each $R_4$ is independently halogen, $C_1$-$C_6$alkyl, $C_1$-$C_6$haloalkyl, or $C_1$-$C_6$alkoxy. In some embodiments is a compound of Formula (Ia) wherein p is 1 or 2 and each $R_4$ is independently halogen, $C_1$-$C_6$alkyl, $C_1$-$C_6$haloalkyl, or $C_1$-$C_6$alkoxy. In some embodiments is a compound of Formula (Ia) wherein p is 1 and $R_4$ is halogen, $C_1$-$C_6$alkyl, $C_1$-$C_6$haloalkyl, or $C_1$-$C_6$alkoxy. In some embodiments is a compound of Formula (Ia) wherein p is 1 and $R_4$ is halogen. In some embodiments is a compound of Formula (Ia) wherein p is 1 and $R_4$ is —F. In some embodiments is a compound of Formula (Ia) wherein p is 1 and $R_4$ is —Cl. In some embodiments is a compound of Formula (Ia) wherein p is 1 and $R_4$ is $C_1$-$C_6$alkyl. In some embodiments is a compound of Formula (Ia) wherein p is 1 and $R_4$ is —CH$_3$. In some embodiments is a compound of Formula (Ia) wherein p is 1 and $R_4$ is $C_1$-$C_6$haloalkyl. In some embodiments is a compound of Formula (Ia) wherein p is 1 and $R_4$ is —CF$_3$. In some embodiments is a compound of Formula (Ia) wherein p is 1 and $R_4$ is $C_1$-$C_6$alkoxy. In some embodiments is a compound of Formula (Ia) wherein p is 1 and $R_4$ is —OCH$_3$.

In some embodiments is a compound of Formula (Ia) wherein q is 0, 1, or 2. In some embodiments is a compound of Formula (Ia) wherein q is 0 or 1. In some embodiments is a compound of Formula (Ia) wherein q is 0. In some embodiments is a compound of Formula (Ia) wherein q is 1. In some embodiments is a compound of Formula (Ia) wherein q is 2. In some embodiments is a compound of Formula (Ia) wherein q is 3. In some embodiments is a compound of Formula (Ia) wherein q is 1, 2, or 3 and each $R_5$ is independently halogen, $C_1$-$C_6$alkyl, $C_1$-$C_6$haloalkyl, or $C_1$-$C_6$alkoxy. In some embodiments is a compound of Formula (Ia) wherein q is 1 or 2 and each $R_5$ is independently halogen, $C_1$-$C_6$alkyl, $C_1$-$C_6$haloalkyl, or $C_1$-$C_6$alkoxy. In some embodiments is a compound of Formula (Ia) wherein q is 1 and $R_5$ is halogen, $C_1$-$C_6$alkyl, $C_1$-$C_6$haloalkyl, or $C_1$-$C_6$alkoxy. In some embodiments is a compound of Formula (Ia) wherein q is 1 and $R_5$ is halogen. In some embodiments is a compound of Formula (Ia) wherein q is 1 and $R_5$ is —F. In some embodiments is a compound of Formula (Ia) wherein q is 1 and $R_5$ is —Cl. In some embodiments is a compound of Formula (Ia) wherein q is 1 and $R_5$ is $C_1$-$C_6$alkyl. In some embodiments is a compound of Formula (Ia) wherein q is 1 and $R_5$ is —CH$_3$. In some embodiments is a compound of Formula (Ia) wherein q is 1 and $R_5$ is $C_1$-$C_6$haloalkyl. In some embodiments is a compound of Formula (Ia) wherein q is 1 and $R_5$ is —CF$_3$. In some embodiments is a compound of Formula (Ia) wherein q is 1 and $R_5$ is $C_1$-$C_6$alkoxy. In some embodiments is a compound of Formula (Ia) wherein q is 1 and $R_5$ is —OCH$_3$.

In some embodiments is a compound of Formula (Ia) wherein p is 1, $R_4$ is $C_1$-$C_6$alkyl and q is 0. In some embodiments is a compound of Formula (Ia) wherein p is 0 or 1 and $R_4$ is —CH$_3$. In some embodiments is a compound of Formula (Ia) wherein p is 0 or 1, $R_4$ is —CH$_3$ and q is 0. In some embodiments is a compound of Formula (Ia) wherein p is 1, $R_4$ is —CH$_3$ and q is 0. In some embodiments is a compound of Formula (Ia) wherein p is 1, $R_4$ is $C_1$-$C_6$haloalkyl and q is 0. In some embodiments is a compound of Formula (Ia) wherein p is 1, $R_4$ is —CF$_3$ and q is 0.

In some embodiments is a compound of Formula (Ia) wherein m is 0 or 1, n is 0 or 1, p is 0 or 1, and q is 0 or 1. In some embodiments is a compound of Formula (Ia) wherein m is 0, n is 0, p is 0, and q is 0. In some embodiments is a compound of Formula (Ia) wherein m is 1, n is 0, p is 0, q is 0 and $R_2$ is halogen, $C_1$-$C_6$alkyl, or $C_1$-$C_6$alkoxy. In some embodiments is a compound of Formula (Ia) wherein m is 0, n is 1, p is 0, q is 0, and $R_3$ is halogen, $C_1$-$C_6$alkyl, $C_1$-$C_6$haloalkyl, or $C_1$-$C_6$alkoxy. In some embodiments is a compound of Formula (Ia) wherein m is 0, n is 0, p is 1, q is 0 and $R_4$ is halogen, $C_1$-$C_6$alkyl, $C_1$-$C_6$haloalkyl, or $C_1$-$C_6$alkoxy. In some embodiments is a compound of Formula (Ia) wherein m is 0, n is 0, p is 0, q is 1, and $R_5$ is halogen, $C_1$-$C_6$alkyl, $C_1$-$C_6$haloalkyl, or $C_1$-$C_6$alkoxy.

In another aspect is a compound of Formula (Ib):

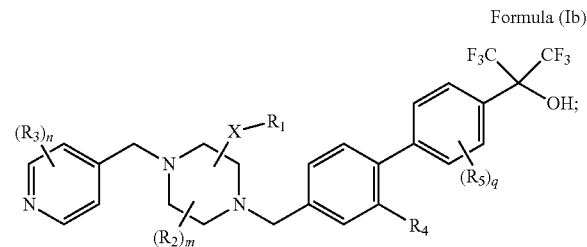

Formula (Ib)

wherein:
X is a bond, $C_1$-$C_6$alkyl, or $C_1$-$C_6$heteroalkyl;
$R_1$ is —C(=O)O$R_6$ or —C(=O)N($R_6$)$_2$;
each $R_2$ is independently halogen, $C_1$-$C_6$alkyl, or $C_1$-$C_6$alkoxy;
each $R_3$ is independently halogen, $C_1$-$C_6$alkyl, $C_1$-$C_6$haloalkyl, $C_1$-$C_6$alkoxy, $C_1$-$C_6$heteroalkyl, —O$R_7$, —N($R_7$)$_2$, —CN, —C(=O)R, —C(=O)O$R_7$, —C(=O)N($R_7$)$_2$, —N$R_7$C(=O)$R_8$, —N$R_7$SO$_2$$R_8$, —SO$_2$$R_8$, or —SO$_2$N($R_7$)$_2$;
$R_4$ is hydrogen or $C_1$-$C_6$alkyl;
each $R_5$ is independently halogen, $C_1$-$C_6$alkyl, $C_1$-$C_6$haloalkyl, $C_1$-$C_6$alkoxy, $C_1$-$C_6$heteroalkyl, —O$R_7$, —N($R_7$)$_2$, —CN, —C(=O)R, —C(=O)O$R_7$, —C(=O)N($R_7$)$_2$, —N$R_7$C(=O)$R_8$, —N$R_7$SO$_2$$R_8$, —SO$_2$$R_8$, or —SO$_2$N($R_7$)$_2$;
each $R_6$ is independently hydrogen, $C_1$-$C_6$alkyl, or —$C_1$-$C_6$alkyl-Y—$R_9$;
each Y is independently —O—, —S—, or —N($R_{10}$)—;
each $R_7$ is independently hydrogen, $C_1$-$C_6$alkyl, $C_1$-$C_6$haloalkyl, or $C_1$-$C_6$heteroalkyl;
each $R_8$ is independently $C_1$-$C_6$alkyl or $C_1$-$C_6$heteroalkyl;
each $R_9$ is independently hydrogen or $C_1$-$C_6$alkyl;
each $R_{10}$ is independently hydrogen or $C_1$-$C_6$alkyl;
m is 0, 1, 2, 3, or 4;
n is 0, 1, 2, 3, or 4; and
q is 0, 1, 2, or 3;
or a pharmaceutically acceptable salt or solvate thereof.

In some embodiments is a compound of Formula (Ib) wherein X is a bond. In some embodiments is a compound of Formula (Ib) wherein X is $C_1$-$C_6$alkyl. In some embodiments is a compound of Formula (Ib) wherein X is —CH$_2$—. In some embodiments is a compound of Formula (Ib) wherein X is $C_1$-$C_6$heteroalkyl.

In some embodiments is a compound of Formula (Ib) wherein $R_1$ is —C(=O)$OR_6$. In some embodiments is a compound of Formula (Ib) wherein $R_1$ is —C(=O)$OR_6$ and $R_6$ is hydrogen. In some embodiments is a compound of Formula (Ib) wherein $R_1$ is —C(=O)$OR_6$ and $R_6$ is $C_1$-$C_6$alkyl or —$C_1$-$C_6$alkyl-Y—$R_9$. In some embodiments is a compound of Formula (Ib) wherein $R_1$ is —C(=O)$OR_6$ and $R_6$ is $C_1$-$C_6$alkyl. In some embodiments is a compound of Formula (Ib) wherein $R_1$ is —C(=O)$OR_6$ and $R_6$ is —$CH_3$, —$CH_2CH_3$, or —CH($CH_3$)$_2$. In some embodiments is a compound of Formula (Ib) wherein $R_1$ is —C(=O)$OR_6$ and $R_6$ is —$CH_3$. In some embodiments is a compound of Formula (Ib) wherein $R_1$ is —C(=O)$OR_6$ and $R_6$ is —$CH_2CH_3$. In some embodiments is a compound of Formula (Ib) wherein $R_1$ is —C(=O)$OR_6$ and $R_6$ is —CH($CH_3$)$_2$. In some embodiments is a compound of Formula (Ib) wherein $R_1$ is —C(=O)$OR_6$, $R_6$ is $C_1$-$C_6$alkyl or —$C_1$-$C_6$alkyl-Y—$R_9$, Y is —O—, and $R_9$ is hydrogen or $C_1$-$C_6$alkyl. In some embodiments is a compound of Formula (Ib) wherein $R_1$ is —C(=O)$OR_6$ and $R_6$ is —$C_1$-$C_6$alkyl-Y—$R_9$. In some embodiments is a compound of Formula (Ib) wherein $R_1$ is —C(=O)$OR_6$, $R_6$ is —$C_1$-$C_6$alkyl-Y—$R_9$, and Y is —O—. In some embodiments is a compound of Formula (Ib) wherein $R_1$ is —C(=O)$OR_6$, $R_6$ is —$C_1$-$C_6$alkyl-Y—$R_9$, and Y is —O—, and $R_9$ is hydrogen. In some embodiments is a compound of Formula (Ib) wherein $R_1$ is —C(=O)$OR_6$, $R_6$ is —$C_1$-$C_6$alkyl-Y—$R_9$, and Y is —O—, and $R_9$ is $C_1$-$C_6$alkyl. In some embodiments is a compound of Formula (Ib) wherein $R_1$ is —C(=O)$OR_6$, $R_6$ is —$C_1$-$C_6$alkyl-Y—$R_9$, and Y is —S—. In some embodiments is a compound of Formula (Ib) wherein $R_1$ is —C(=O)$OR_6$, $R_6$ is —$C_1$-$C_6$alkyl-Y—$R_9$, and Y is —N($R_{10}$)—. In some embodiments is a compound of Formula (Ib) wherein $R_1$ is —C(=O)$OR_6$, $R_6$ is —$C_1$-$C_6$alkyl-Y—$R_9$, and Y is —N(H)—. In some embodiments is a compound of Formula (Ib) wherein $R_9$ is hydrogen. In some embodiments is a compound of Formula (Ib) wherein $R_9$ is $C_1$-$C_6$alkyl. In some embodiments is a compound of Formula (Ib) wherein $R_9$ is —$CH_3$. In some embodiments is a compound of Formula (Ib) wherein $R_9$ is —$CH_2CH_3$. In some embodiments is a compound of Formula (Ib) wherein $R_9$ is —CH($CH_3$)$_2$. In some embodiments is a compound of Formula (Ib) wherein $R_1$ is —C(=O)OCH$_2$CH$_2$OH. In some embodiments is a compound of Formula (Ib) wherein $R_1$ is —C(=O)OCH$_2$CH$_2$OCH$_3$. In some embodiments is a compound of Formula (Ib) wherein $R_1$ is —C(=O)OCH$_2$CH$_2$OCH$_2$CH$_3$. In some embodiments is a compound of Formula (Ib) wherein $R_1$ is —C(=O)OCH$_2$CH$_2$NH$_2$. In some embodiments is a compound of Formula (Ib) wherein $R_1$ is —C(=O)OCH$_2$CH$_2$N(H)CH$_3$. In some embodiments is a compound of Formula (Ib) wherein $R_1$ is —C(=O)OCH$_2$CH$_2$N(H)CH$_2$CH$_3$.

In some embodiments is a compound of Formula (Ib) wherein $R_1$ is —C(=O)N($R_6$)$_2$. In some embodiments is a compound of Formula (Ib) wherein $R_1$ is —C(=O)N($R_6$)$_2$ and each $R_6$ is hydrogen. In some embodiments is a compound of Formula (Ib) wherein $R_1$ is —C(=O)N($R_6$)$_2$, and one $R_6$ is hydrogen and one $R_6$ is $C_1$-$C_6$alkyl. In some embodiments is a compound of Formula (Ib) wherein $R_1$ is —C(=O)N($R_6$)$_2$, and one $R_6$ is hydrogen and one $R_6$ is —$CH_3$. In some embodiments is a compound of Formula (Ib) wherein $R_1$ is —C(=O)N($R_6$)$_2$, and one $R_6$ is hydrogen and one $R_6$ is —$CH_2CH_3$. In some embodiments is a compound of Formula (Ib) wherein $R_1$ is —C(=O)N($R_6$)$_2$, and one $R_6$ is hydrogen and one $R_6$ is —CH($CH_3$)$_2$. In some embodiments is a compound of Formula (Ib) wherein $R_1$ is —C(=O)N($R_6$)$_2$ and each $R_6$ is —$CH_3$. In some embodiments is a compound of Formula (Ib) wherein $R_1$ is —C(=O)N($R_6$)$_2$ and each $R_6$ is —$CH_2CH_3$. In some embodiments is a compound of Formula (Ib) wherein $R_1$ is —C(=O)N($R_6$)$_2$, and one $R_6$ is hydrogen and $R_6$ is —$C_1$-$C_6$alkyl-Y—$R_9$. In some embodiments is a compound of Formula (Ib) wherein $R_1$ is —C(=O)N($R_6$)$_2$, one $R_6$ is hydrogen and one $R_6$ is —$C_1$-$C_6$alkyl-Y—$R_9$, and Y is —O—. In some embodiments is a compound of Formula (Ib) wherein $R_1$ is —C(=O)N($R_6$)$_2$, one $R_6$ is hydrogen and one $R_6$ is —$C_1$-$C_6$alkyl-Y—$R_9$, and Y is —S—. In some embodiments is a compound of Formula (Ib) wherein $R_1$ is —C(=O)N($R_6$)$_2$, one $R_6$ is hydrogen and one $R_6$ is —$C_1$-$C_6$alkyl-Y—$R_9$, and Y is —N($R_{10}$)—. In some embodiments is a compound of Formula (Ib) wherein $R_1$ is —C(=O)N($R_6$)$_2$, one $R_6$ is hydrogen and one $R_6$ is —$C_1$-$C_6$alkyl-Y—$R_9$, and Y is —N(H)—. In some embodiments is a compound of Formula (Ib) wherein $R_9$ is hydrogen. In some embodiments is a compound of Formula (Ib) wherein $R_9$ is $C_1$-$C_6$alkyl. In some embodiments is a compound of Formula (Ib) wherein $R_9$ is —$CH_3$. In some embodiments is a compound of Formula (Ib) wherein $R_9$ is —$CH_2CH_3$. In some embodiments is a compound of Formula (Ib) wherein $R_9$ is —CH($CH_3$)$_2$. In some embodiments is a compound of Formula (Ib) wherein $R_1$ is —C(=O)N(H)CH$_2$CH$_2$OH. In some embodiments is a compound of Formula (Ib) wherein $R_1$ is —C(=O)N(H)CH$_2$CH$_2$OCH$_3$. In some embodiments is a compound of Formula (Ib) wherein $R_1$ is —C(=O)N(H)CH$_2$CH$_2$OCH$_2$CH$_3$. In some embodiments is a compound of Formula (Ib) wherein $R_1$ is —C(=O)N(H)CH$_2$CH$_2$NH$_2$. In some embodiments is a compound of Formula (Ib) wherein $R_1$ is —C(=O)N(H)CH$_2$CH$_2$N(H)CH$_3$. In some embodiments is a compound of Formula (Ib) wherein $R_1$ is —C(=O)N(H)CH$_2$CH$_2$N(H)CH$_2$CH$_3$.

In some embodiments is a compound of Formula (Ib) wherein —X—$R_1$ is —C(=O)OH. In some embodiments is a compound of Formula (Ib) wherein —X—$R_1$ is —C(=O)OCH$_3$. In some embodiments is a compound of Formula (Ib) wherein —X—$R_1$ is —C(=O)OCH$_2$CH$_3$. In some embodiments is a compound of Formula (Ib) wherein —X—$R_1$ is —C(=O)OCH(CH$_3$)$_2$. In some embodiments is a compound of Formula (Ib) wherein —X—$R_1$ is —C(=O)OCH$_2$CH$_2$OH. In some embodiments is a compound of Formula (Ib) wherein —X—$R_1$ is —C(=O)OCH$_2$CH$_2$OCH$_3$. In some embodiments is a compound of Formula (Ib) wherein —X—$R_1$ is —C(=O)OCH$_2$CH$_2$OCH$_2$CH$_3$. In some embodiments is a compound of Formula (Ib) wherein —X—$R_1$ is —C(=O)OCH$_2$CH$_2$NH$_2$. In some embodiments is a compound of Formula (Ib) wherein —X—$R_1$ is —CH$_2$C(=O)OH. In some embodiments is a compound of Formula (Ib) wherein —X—$R_1$ is —CH$_2$C(=O)OCH$_3$. In some embodiments is a compound of Formula (Ib) wherein —X—$R_1$ is —CH$_2$C(=O)OCH$_2$CH$_3$. In some embodiments is a compound of Formula (Ib) wherein —X—$R_1$ is —CH$_2$C(=O)OCH(CH$_3$)$_2$. In some embodiments is a compound of Formula (Ib) wherein —X—$R_1$ is —CH$_2$C(=O)OCH$_2$CH$_2$OH. In some embodiments is a compound of Formula (Ib) wherein —X—$R_1$ is —CH$_2$C(=O)OCH$_2$CH$_2$OCH$_3$. In some embodiments is a compound of Formula (Ib) wherein —X—$R_1$ is —CH$_2$C(=O)OCH$_2$CH$_2$OCH$_2$CH$_3$. In some embodiments is a compound of Formula (Ib) wherein —X—$R_1$ is —CH$_2$C(=O)OCH$_2$CH$_2$NH$_2$.

In some embodiments is a compound of Formula (Ib) wherein —X—$R_1$ is —C(=O)N(H)CH$_3$. In some embodiments is a compound of Formula (Ib) wherein —X—$R_1$ is —C(=O)N(H)CH$_2$CH$_3$. In some embodiments is a compound of Formula (Ib) wherein —X—$R_1$ is —C(=O)N(H)

$CH(CH_3)_2$. In some embodiments is a compound of Formula (Ib) wherein —X—$R_1$ is —C(=O)N(H)$CH_2CH_2$OH. In some embodiments is a compound of Formula (Ib) wherein —X—$R_1$ is —C(=O)N(H)$CH_2CH_2OCH_3$. In some embodiments is a compound of Formula (Ib) wherein —X—$R_1$ is —C(=O)N(H)$CH_2CH_2OCH_2CH_3$. In some embodiments is a compound of Formula (Ib) wherein —X—$R_1$ is —C(=O)N(H)$CH_2CH_2NH_2$. In some embodiments is a compound of Formula (Ib) wherein —X—$R_1$ is —$CH_2$C(=O)N(H)$CH_3$. In some embodiments is a compound of Formula (Ib) wherein —X—$R_1$ is —$CH_2$C(=O)N(H)$CH_2CH_3$. In some embodiments is a compound of Formula (Ib) wherein —X—$R_1$ is —$CH_2$C(=O)N(H)CH$(CH_3)_2$. In some embodiments is a compound of Formula (Ib) wherein —X—$R_1$ is —$CH_2$C(=O)N(H)$CH_2CH_2$OH. In some embodiments is a compound of Formula (Ib) wherein —X—$R_1$ is —$CH_2$C(=O)N(H)$CH_2CH_2OCH_3$. In some embodiments is a compound of Formula (Ib) wherein —X—$R_1$ is —$CH_2$C(=O)N(H)$CH_2CH_2OCH_2CH_3$. In some embodiments is a compound of Formula (Ib) wherein —X—$R_1$ is —$CH_2$C(=O)N(H)$CH_2CH_2NH_2$.

In some embodiments is a compound of Formula (Ib) wherein m is 0, 1, 2, or 3. In some embodiments is a compound of Formula (Ib) wherein m is 0, 1, or 2. In some embodiments is a compound of Formula (Ib) wherein m is 0 or 1. In some embodiments is a compound of Formula (Ib) wherein m is 0. In some embodiments is a compound of Formula (Ib) wherein m is 1. In some embodiments is a compound of Formula (Ib) wherein m is 2. In some embodiments is a compound of Formula (Ib) wherein m is 3. In some embodiments is a compound of Formula (Ib) wherein m is 4. In some embodiments is a compound of Formula (Ib) wherein m is 1, 2, or 3 and each $R_2$ is independently halogen, $C_1$-$C_6$alkyl, or $C_1$-$C_6$alkoxy. In some embodiments is a compound of Formula (Ib) wherein m is 1 or 2 and each $R_2$ is independently halogen, $C_1$-$C_6$alkyl, or $C_1$-$C_6$alkoxy. In some embodiments is a compound of Formula (Ib) wherein m is 1 and $R_2$ is halogen, $C_1$-$C_6$alkyl, or $C_1$-$C_6$alkoxy. In some embodiments is a compound of Formula (Ib) wherein m is 1 and $R_2$ is halogen. In some embodiments is a compound of Formula (Ib) wherein m is 1 and $R_2$ is —Cl. In some embodiments is a compound of Formula (Ib) wherein m is 1 and $R_2$ is $C_1$-$C_6$alkyl. In some embodiments is a compound of Formula (Ib) wherein m is 1 and $R_2$ is —$CH_3$. In some embodiments is a compound of Formula (Ib) wherein m is 1 and $R_2$ is $C_1$-$C_6$alkoxy. In some embodiments is a compound of Formula (Ib) wherein m is 1 and $R_2$ is —$OCH_3$.

In some embodiments is a compound of Formula (Ib) wherein n is 0, 1, 2, or 3. In some embodiments is a compound of Formula (Ib) wherein n is 0, 1, or 2. In some embodiments is a compound of Formula (Ib) wherein n is 0 or 1. In some embodiments is a compound of Formula (Ib) wherein n is 0. In some embodiments is a compound of Formula (Ib) wherein n is 1. In some embodiments is a compound of Formula (Ib) wherein n is 2. In some embodiments is a compound of Formula (Ib) wherein n is 3. In some embodiments is a compound of Formula (Ib) wherein n is 4. In some embodiments is a compound of Formula (Ib) wherein n is 1, 2, or 3 and each $R_3$ is independently halogen, $C_1$-$C_6$alkyl, $C_1$-$C_6$haloalkyl, or $C_1$-$C_6$alkoxy. In some embodiments is a compound of Formula (Ib) wherein n is 1 or 2 and each $R_3$ is independently halogen, $C_1$-$C_6$alkyl, $C_1$-$C_6$haloalkyl, or $C_1$-$C_6$alkoxy. In some embodiments is a compound of Formula (Ib) wherein n is 1 and $R_3$ is halogen, $C_1$-$C_6$alkyl, $C_1$-$C_6$haloalkyl, or $C_1$-$C_6$alkoxy. In some embodiments is a compound of Formula (Ib) wherein n is 1 and $R_3$ is halogen. In some embodiments is a compound of Formula (Ib) wherein n is 1 and $R_3$ is —F. In some embodiments is a compound of Formula (Ib) wherein n is 1 and $R_3$ is —Cl. In some embodiments is a compound of Formula (Ib) wherein n is 1 and $R_3$ is $C_1$-$C_6$alkyl. In some embodiments is a compound of Formula (Ib) wherein n is 1 and $R_3$ is —$CH_3$. In some embodiments is a compound of Formula (Ib) wherein n is 1 and $R_3$ is $C_1$-$C_6$haloalkyl. In some embodiments is a compound of Formula (Ib) wherein n is 1 and $R_3$ is —$CF_3$. In some embodiments is a compound of Formula (Ib) wherein n is 1 and $R_3$ is $C_1$-$C_6$alkoxy. In some embodiments is a compound of Formula (Ib) wherein n is 1 and $R_3$ is —$OCH_3$.

In some embodiments is a compound of Formula (Ib) wherein $R_4$ is hydrogen. In some embodiments is a compound of Formula (Ib) wherein $R_4$ is $C_1$-$C_6$alkyl. In some embodiments is a compound of Formula (Ib) wherein $R_4$ is $CH_3$.

In some embodiments is a compound of Formula (Ib) wherein q is 0, 1, or 2. In some embodiments is a compound of Formula (Ib) wherein q is 0 or 1. In some embodiments is a compound of Formula (Ib) wherein q is 0. In some embodiments is a compound of Formula (Ib) wherein q is 1. In some embodiments is a compound of Formula (Ib) wherein q is 2. In some embodiments is a compound of Formula (Ib) wherein q is 3. In some embodiments is a compound of Formula (Ib) wherein q is 1, 2, or 3 and each $R_5$ is independently halogen, $C_1$-$C_6$alkyl, $C_1$-$C_6$haloalkyl, or $C_1$-$C_6$alkoxy. In some embodiments is a compound of Formula (Ib) wherein q is 1 or 2 and each $R_5$ is independently halogen, $C_1$-$C_6$alkyl, $C_1$-$C_6$haloalkyl, or $C_1$-$C_6$alkoxy. In some embodiments is a compound of Formula (Ib) wherein q is 1 and $R_5$ is halogen, $C_1$-$C_6$alkyl, $C_1$-$C_6$haloalkyl, or $C_1$-$C_6$alkoxy. In some embodiments is a compound of Formula (Ib) wherein q is 1 and $R_5$ is halogen. In some embodiments is a compound of Formula (Ib) wherein q is 1 and $R_5$ is —F. In some embodiments is a compound of Formula (Ib) wherein q is 1 and $R_5$ is —Cl. In some embodiments is a compound of Formula (Ib) wherein q is 1 and $R_5$ is $C_1$-$C_6$alkyl. In some embodiments is a compound of Formula (Ib) wherein q is 1 and $R_5$ is —$CH_3$. In some embodiments is a compound of Formula (Ib) wherein q is 1 and $R_5$ is $C_1$-$C_6$haloalkyl. In some embodiments is a compound of Formula (Ib) wherein q is 1 and $R_5$ is —$CF_3$. In some embodiments is a compound of Formula (Ib) wherein q is 1 and $R_5$ is $C_1$-$C_6$alkoxy. In some embodiments is a compound of Formula (Ib) wherein q is 1 and $R_5$ is —$OCH_3$.

In some embodiments is a compound of Formula (Ib) wherein m is 0 or 1, n is 0 or 1, and q is 0 or 1. In some embodiments is a compound of Formula (Ib) wherein m is 0 or 1, n is 0 or 1, q is 0 or 1, and $R_4$ is hydrogen. In some embodiments is a compound of Formula (Ib) wherein m is 0 or 1, n is 0 or 1, q is 0 or 1, and $R_4$ is $C_1$-$C_6$alkyl. In some embodiments is a compound of Formula (Ib) wherein m is 0 or 1, n is 0 or 1, q is 0 or 1, and $R_4$ is —$CH_3$. In some embodiments is a compound of Formula (Ib) wherein m is 0, n is 0, q is 0, and $R_4$ is hydrogen. In some embodiments is a compound of Formula (Ib) wherein m is 0, n is 0, q is 0, and $R_4$ is $C_1$-$C_6$alkyl. In some embodiments is a compound of Formula (Ib) wherein m is 0, n is 0, q is 0, and $R_4$ is —$CH_3$. In some embodiments is a compound of Formula (Ib) wherein m is 1, n is 0, q is 0 and $R_2$ is halogen, $C_1$-$C_6$alkyl, or $C_1$-$C_6$alkoxy. In some embodiments is a compound of Formula (Ib) wherein m is 0, n is 1, q is 0, $R_4$ is hydrogen, and $R_3$ is halogen, $C_1$-$C_6$alkyl, $C_1$-$C_6$haloalkyl, or $C_1$-$C_6$alkoxy. In some embodiments is a compound of Formula (Ib) wherein m is 0, n is 1, q is 0, $R_4$ is $C_1$-$C_6$alkyl, and $R_3$ is halogen, $C_1$-$C_6$alkyl, $C_1$-$C_6$haloalkyl, or $C_1$-$C_6$alkoxy. In some embodiments is a compound of Formula (Ib) wherein m is 0, n is 1, q is 0, $R_4$ is —$CH_3$, and $R_3$ is halogen, $C_1$-$C_6$alkyl, $C_1$-$C_6$haloalkyl, or $C_1$-$C_6$alkoxy. In some embodiments is a compound of Formula (Ib) wherein m is 0, n is 0, q is 1, $R_4$ is hydrogen, and $R_5$ is halogen, $C_1$-$C_6$alkyl, $C_1$-$C_6$haloalkyl, or $C_1$-$C_6$alkoxy. In some embodiments is a compound of Formula (Ib) wherein m is 0, n is 0, q is 1, $R_4$ is $C_1$-$C_6$alkyl, and $R_5$ is halogen, $C_1$-$C_6$alkyl, $C_1$-$C_6$haloalkyl, or $C_1$-$C_6$alkoxy. In some embodiments is a compound of Formula (Ib) wherein m is 0, n is 0, q is 1, $R_4$ is —$CH_3$, and $R_5$ is halogen, $C_1$-$C_6$alkyl, $C_1$-$C_6$haloalkyl, or $C_1$-$C_6$alkoxy.

In some embodiments is a compound selected from:

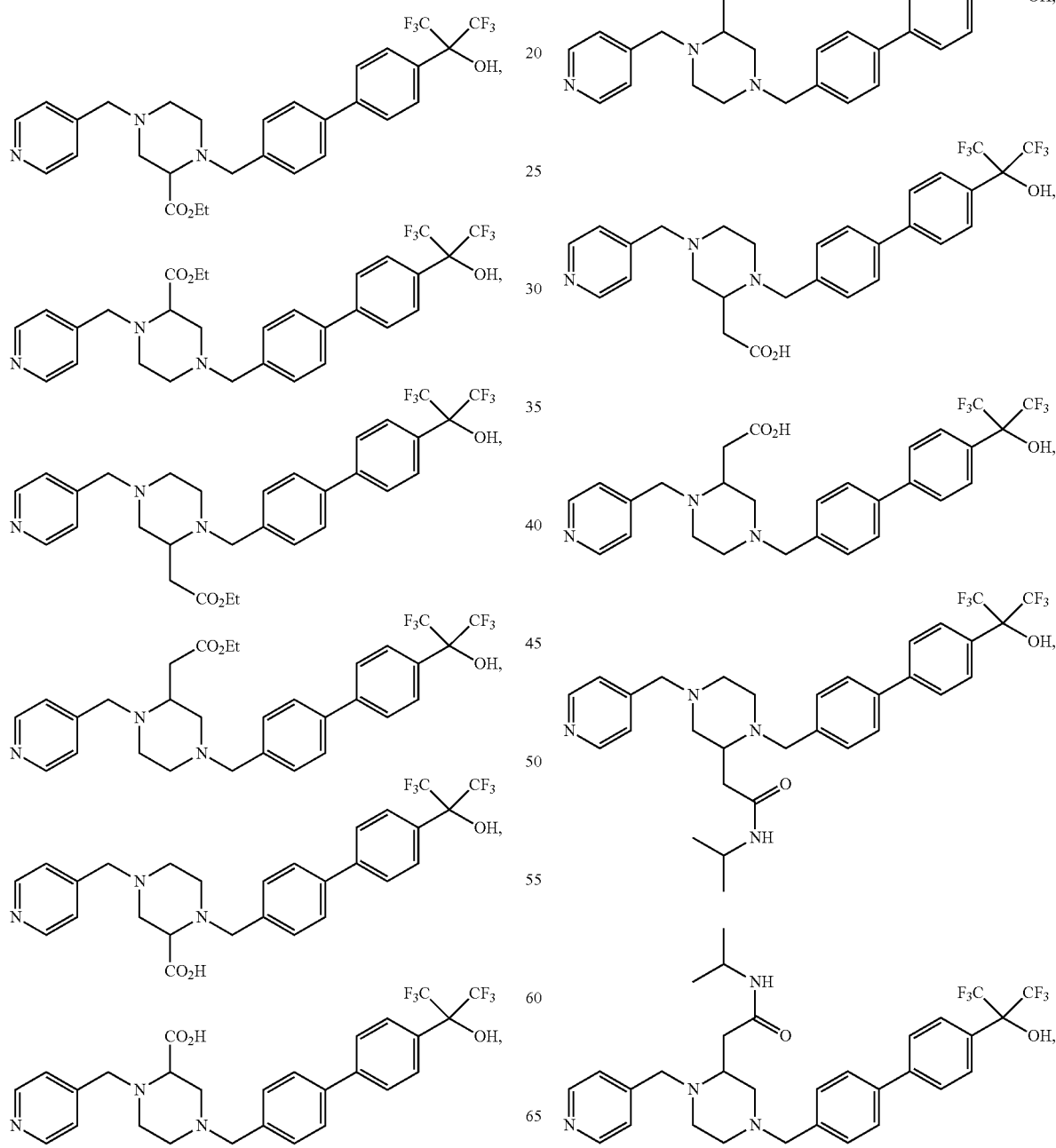

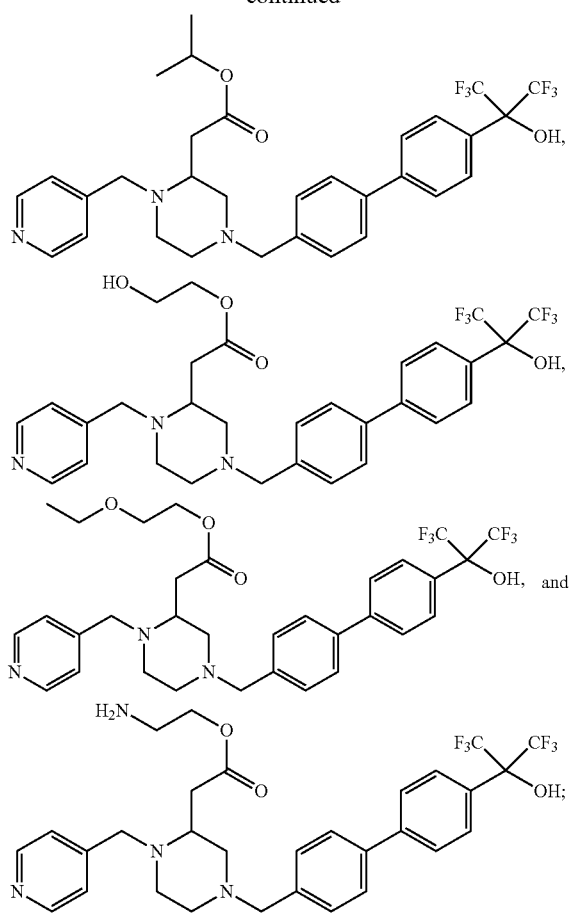
or a pharmaceutically acceptable salt or solvate thereof.
In some embodiments is a compound selected from:
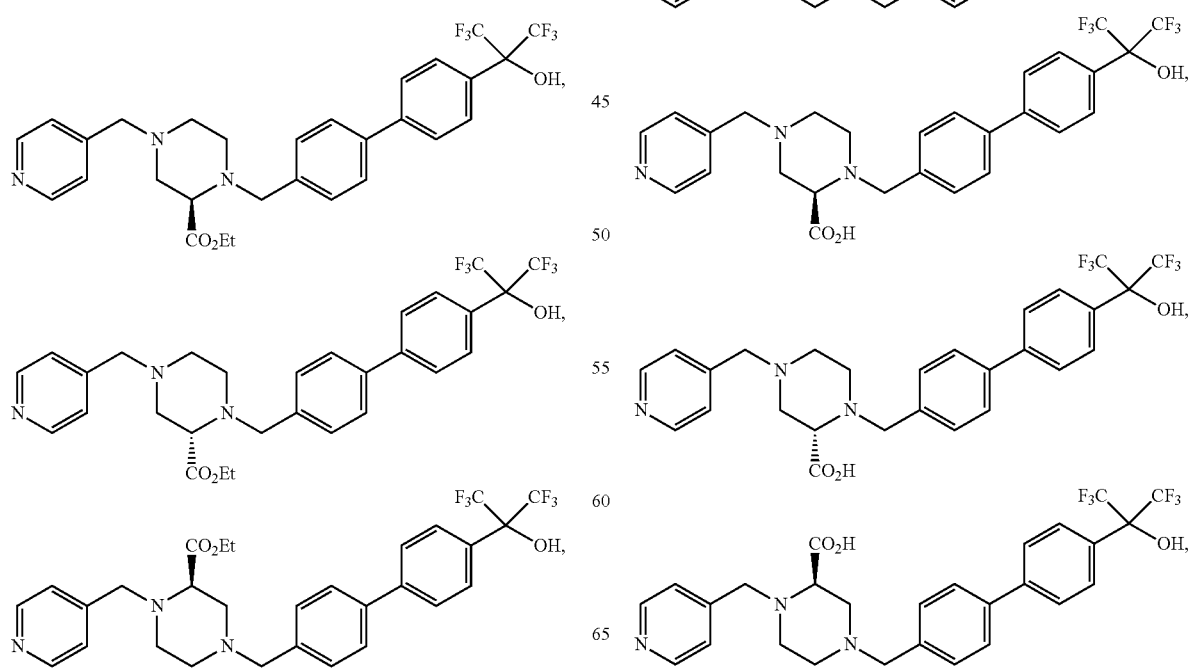
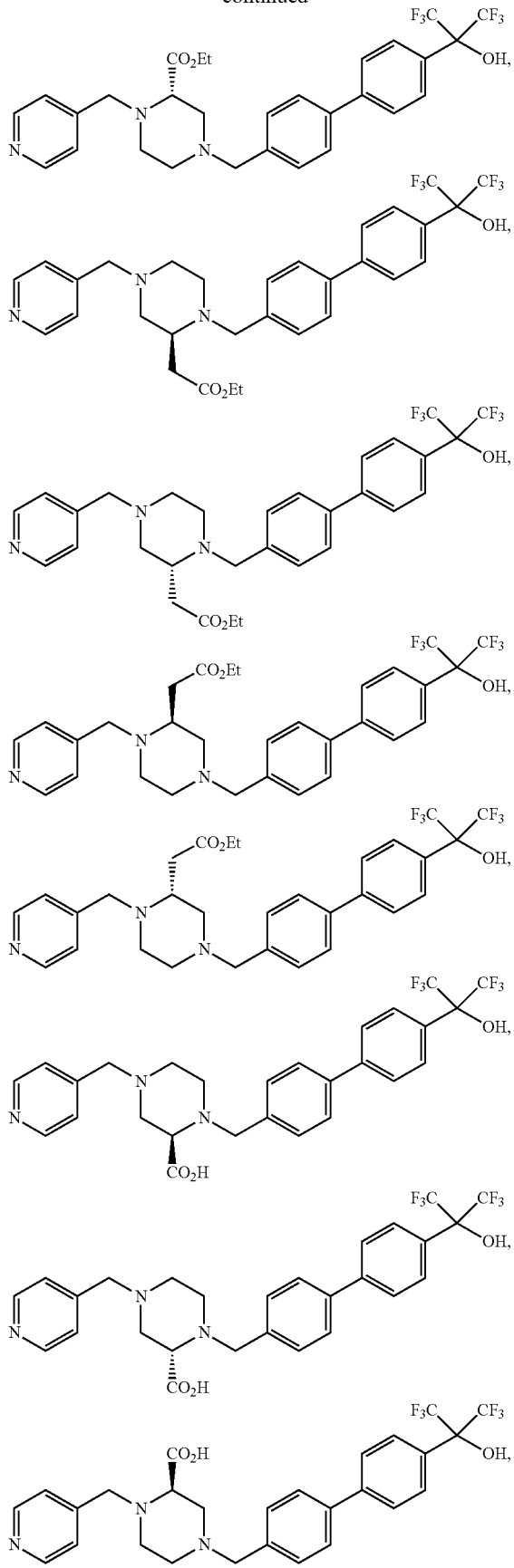

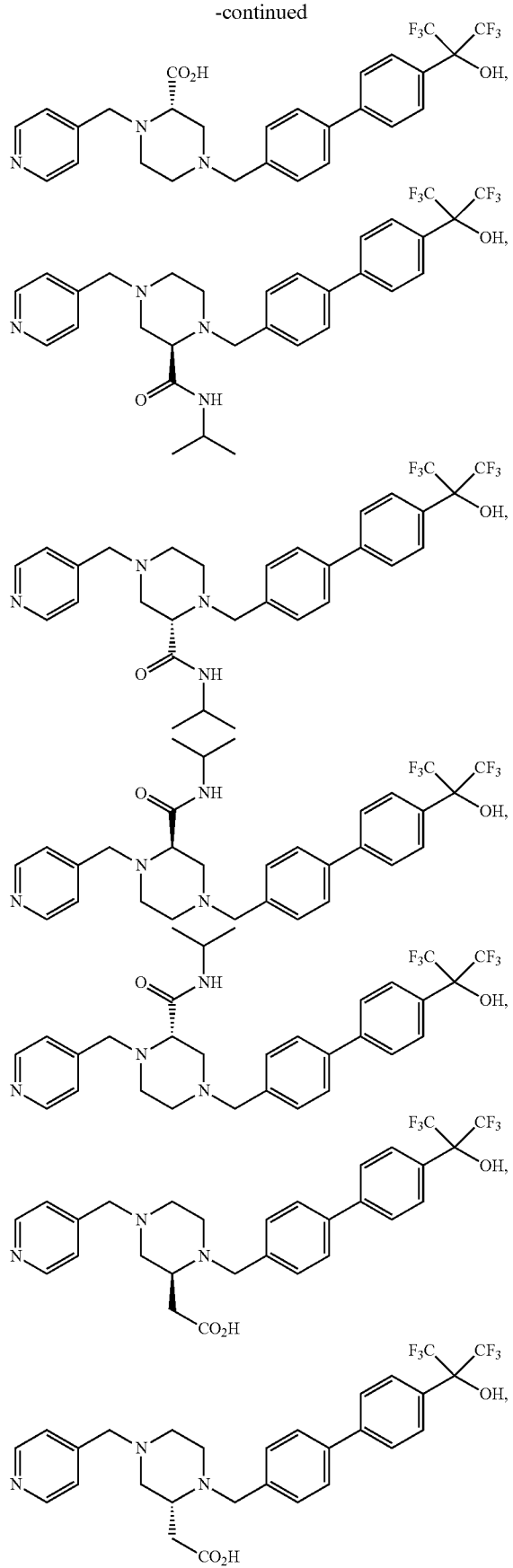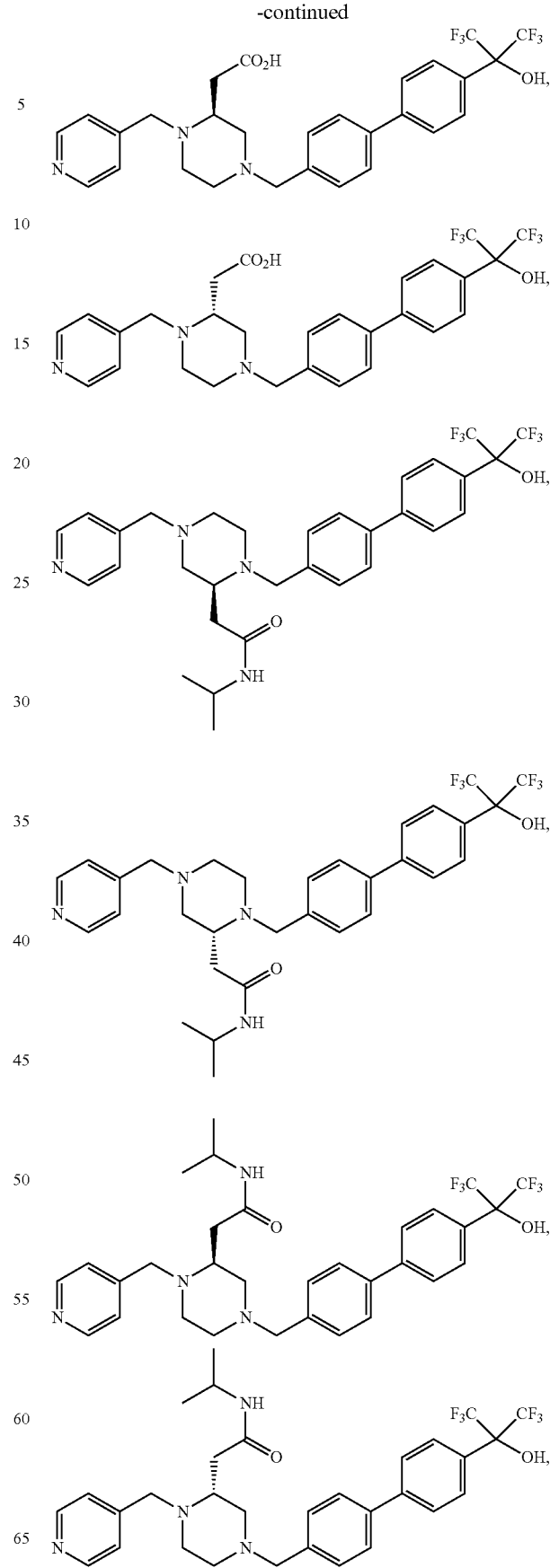

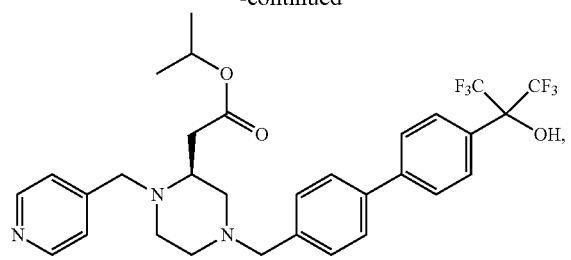
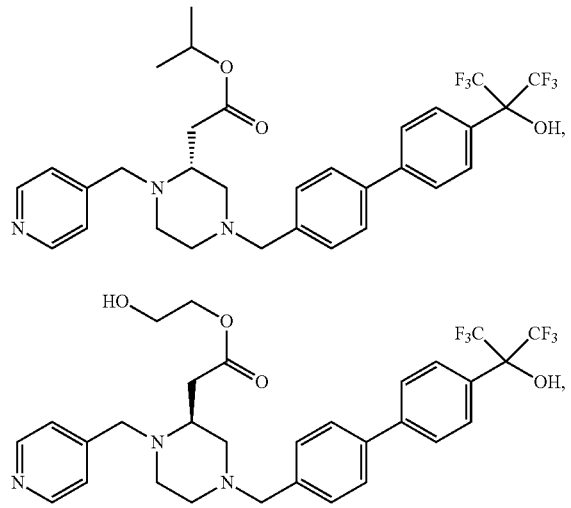
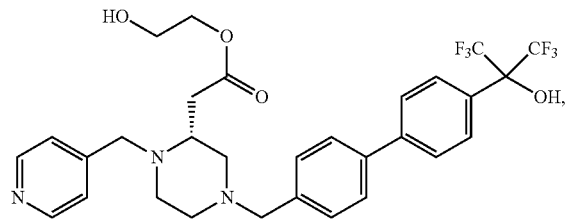
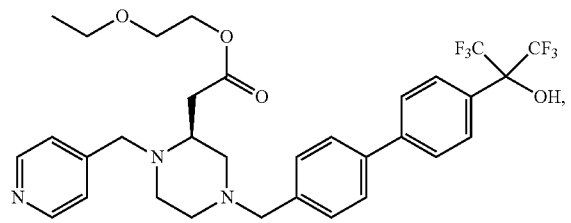
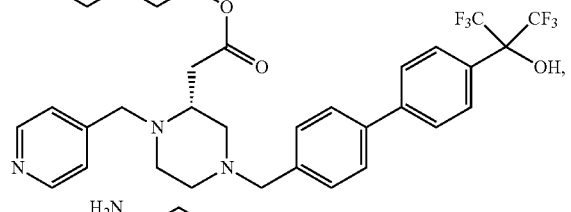
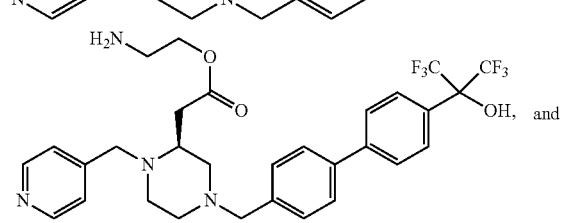
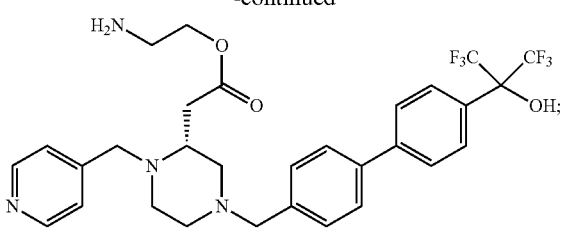
or a pharmaceutically acceptable salt or solvate thereof.
In some embodiments is a compound selected from:
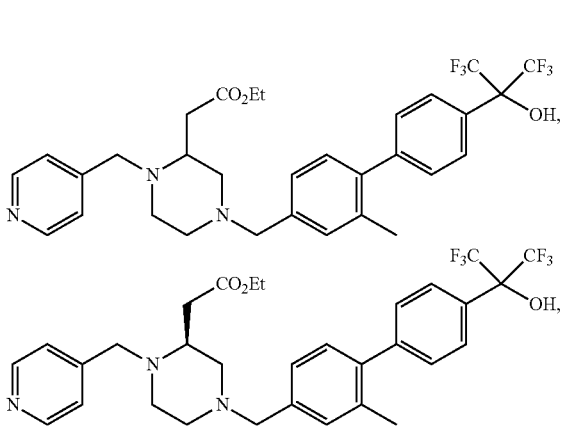
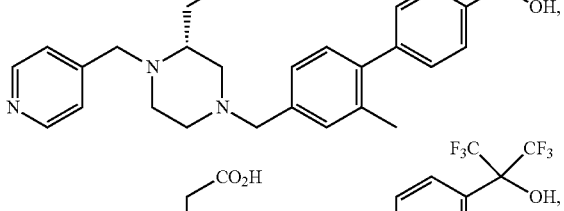
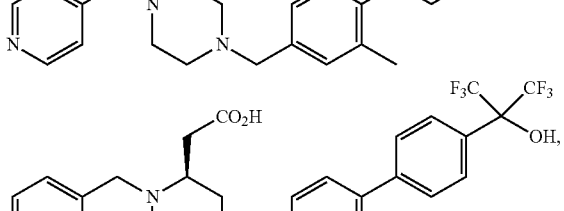
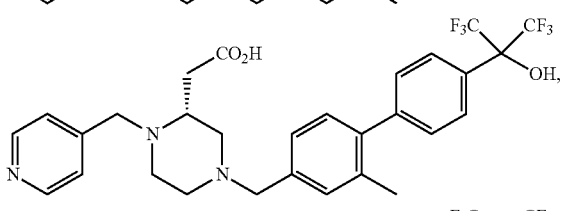
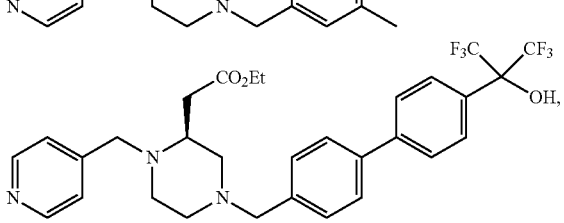

-continued

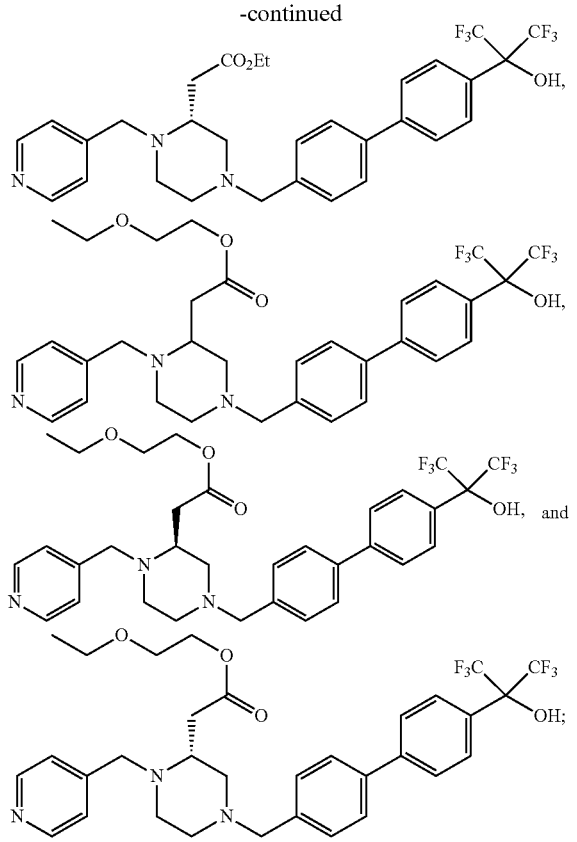

or a pharmaceutically acceptable salt or solvate thereof.

Any combination of the groups described above for the various variables is contemplated herein. Throughout the specification, groups and substituents thereof can be chosen by one skilled in the field to provide stable moieties and compounds.

In some embodiments, the therapeutic agent(s) (e.g. compound of Formula (I), (Ia), or (Ib)) is present in the pharmaceutical composition as a pharmaceutically acceptable salt. In some embodiments, any compound described above is suitable for any method or composition described herein.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of Formula (I), (Ia), or (Ib) is used as a single enantiomer. In some embodiments, a compound of Formula (I), (Ia), or (Ib) is used as a racemic mixture.

The methods and formulations described herein include the use of N-oxides (if appropriate), or pharmaceutically acceptable salts of compounds having the structures presented herein, as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

In some embodiments, the compounds of Formula (I), (Ia), or (Ib) described herein include solvent addition forms thereof. Solvates contain either stoichiometric or non-stoichiometric amounts of a solvent with pharmaceutically acceptable solvents such as water, ethanol, and the like. Hydrates are formed when the solvent is water, or alcoholates are formed when the solvent is alcohol.

In some embodiments, sites on the compounds of Formula (I), (Ia), or (Ib) disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds of Formula (I), (Ia), or (Ib) disclosed herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

Throughout the specification, groups and substituents thereof can be chosen to provide stable moieties and compounds.

RORγ Soft-Drugs

In some embodiments disclosed herein are RORγ modulators which have been structurally modified to incorporate a carboxylic ester functional group to produce an RORγ soft-drug. The carboxylic ester RORγ modulators described herein retain RORγ activity. However, the corresponding carboxylic acids of the ester derivatives lack appreciable RORγ activity. Thus, the carboxylic esters described herein provide an optimal delivery for a topically administered RORγ modulator. The carboxylic esters are potent RORγ modulators which induce the expression and/or protein levels of RORγ in skin cells. However, upon hydrolysis, the corresponding carboxylic acids are devoid of appreciable RORγ activity. Thus, the carboxylic esters will have little or no systemic exposure as they are readily hydrolyzed upon entering the systemic circulation (Scheme A).

Scheme A

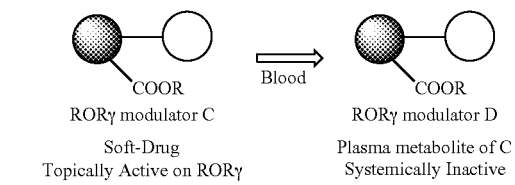

RORγ modulator C
Soft-Drug
Topically Active on RORγ

RORγ modulator D
Plasma metabolite of C
Systemically Inactive

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd$^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

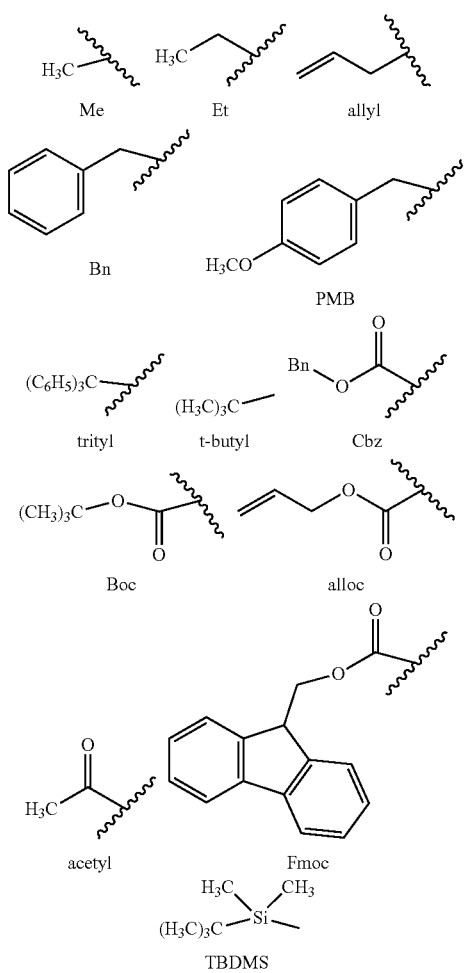

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Methods of Treatment and Prevention

In one embodiment, provided herein are methods for modulating of RORγ activity in a cell by contacting the cell with an RORγ modulator. Examples of such RORγ modulators are described above.

In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition selected from the group consisting of skin aging, scarring, psoriasis, dermatitis, eczema, urticaria, rosacea, burns, and acne. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is skin aging. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is scarring. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is psoriasis. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is dermatitis. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is eczema. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is urticaria. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is rosacea. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is burns. In some embodiments is a method of treating a disease, disorder or condition in an individual in need thereof comprising administering to the individual a therapeutically effective amount of a compound of Formula (I), (Ia), or (Ib), or a pharmaceutically acceptable salt or solvate thereof, wherein the disease, disorder or condition is a dermal disease, disorder or condition is acne.

Pharmaceutical Compositions and Methods of Administration of RORγ Modulators

RORγ modulators described herein are administered to subjects in a biologically compatible form suitable for topical administration to treat or prevent dermal diseases, disorders or conditions. By "biologically compatible form suitable for topical administration" is meant a form of the RORγ modulator to be administered in which any toxic effects are outweighed by the therapeutic effects of the modulator. Administration of RORγ modulators as described herein can be in any pharmacological form including a therapeutically effective amount of an RORγ modulator alone or in combination with a pharmaceutically acceptable carrier.

Topical administration of an RORγ modulator may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin. The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

A therapeutically effective amount of an RORγ modulator may vary according to factors such as the skin aging state, age, sex, and weight of the individual, and the ability of the RORγ modulator to elicit a desired response in the individual. Dosage regime may be adjusted to provide the optimum cosmetic, response. For example, several divided doses may be administered daily, or the dose may be proportionally reduced as indicated by the exigencies of the skin aging.

RORγ modulators can also be linked or conjugated with agents that provide desirable pharmaceutical or pharmacodynamic properties. For example, ROR$_γ$ modulators can be stably linked to a polymer such as polyethylene glycol to obtain desirable properties of solubility, stability, half-life, and other pharmaceutically advantageous properties (see, e.g., Davis et al., Enzyme Eng. 4:169-73 (1978); Bumham N L, Am. J. Hosp. Pharm. 51:210-18 (1994)).

RORγ modulators can be in a composition which aids in delivery into the cytosol of a cell. For example, an RORγ modulator may be conjugated with a carrier moiety such as a liposome that is capable of delivering the modulator into the cytosol of a cell. Such methods are well known in the art (see, e.g., Amselem S et al., Chem. Phys. Lipids 64:219-37 (1993)).

RORγ modulators can be employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the RORγ modulator, use thereof in the cosmetic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

In one embodiment, the anti-skin aging compositions disclosed herein can further comprise a retinoic acid receptor (RAR) ligand. Useful RAR ligands include, for example, all-trans retinoic acid (tretinoin) and/or synthetic retinoic acid receptor ligands. Tretinoin is sold under such trademarks as Atragen®, Avita®, Renova®, Retin-A®, Vesanoid®, and Vitinoin®. Exemplary synthetic retinoic acid receptor ligands include tazarotene (Avage®; ethyl 6-[2-(4,4-dimethylthiochroman-6-yl)ethynyl]pyridine-3-carboxylate) and Differin® (adapalene; 6-[3-(1-adamantyl)-4-methoxyphenyl]-2-naphthoic acid; CD271).

Topical compositions can be prepared by combining the anti-skin aging composition with conventional pharmaceutically acceptable diluents and carriers commonly used in topical dry, liquid, cream, and aerosol formulations. Ointment and creams can, for example, be formulated with an aqueous or oily base with the addition of suitable thickening and/or gelling agents. An exemplary base is water. Thickening agents which can be used according to the nature of the base include aluminum stearate, cetostearyl alcohol, propylene glycol, polyethylene glycols, hydrogenated lanolin, and the like. Lotions can be formulated with an aqueous base and will, in general, also include one or more of the following: stabilizing agents, emulsifying agents, dispersing agents, suspending agents, thickening agents, coloring agents, perfumes, and the like. Powders can be formed with the aid of any suitable powder base, for example, talc, lactose, starch, and the like. Drops can be formulated with an aqueous base or non-aqueous base, and can also include one or more dispersing agents, suspending agents, solubilizing agents, and the like.

In one embodiment, the topical composition may, for example, take the form of hydrogel based on polyacrylic acid or polyacrylamide; as an ointment, for example with polyethyleneglycol (PEG) as the carrier, like the standard ointment DAB 8 (50% PEG 300, 50% PEG 1500); or as an emulsion, especially a microemulsion based on water-in-oil or oil-in-water, optionally with added liposomes. Suitable permeation accelerators (entraining agents) include sulphoxide derivatives such as dimethylsulphoxide (DMSO) or decylmethylsulphoxide (decyl-MSO) and transcutol (diethyleneglycolmonoethylether) or cyclodextrin; as well as pyrrolidones, for example 2-pyrrolidone, N-methyl-2-pyrrolidone, 2-pyrrolidone-5-carboxylic acid, or the biodegradable N-(2-hydroxyethyl)-2-pyrrolidone and the fatty acid esters thereof; urea derivatives such as dodecylurea, 1,3-didodecylurea, and 1,3-diphenylurea; terpenes, for example D-limonene, menthone, a-terpinol, carvol, limonene oxide, or 1,8-cineol.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The carrier can also contain other pharmaceutically-acceptable excipients for modifying or maintaining the pH, osmolarity, viscosity, clarity, color, sterility, stability, rate of dissolution, or odor of the formulation. The anti-skin aging compositions can also further comprise antioxidants, sun screens, natural retinoids (e.g., retinol), and other additives commonly found in skin treatment compositions.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the RORγ modulator and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the RORγ modulator activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such RORγ modulators can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. RORγ modulators that exhibit large therapeutic indices are preferred. While RORγ modulators that exhibit toxic side effects may be used, care should be taken to design a delivery system that targets such modulators to the site of affected tissue in order to minimize potential damage to uninfected cells and, thereby, reduce side effects.

The data obtained from the cell culture assays and animal studies can be used in formulating a range of dosage for use in humans. The dosage of such RORγ modulators lies preferably within a range of circulating concentrations that include the $ED_{50}$ with little or no toxicity. The dosage may vary within this range depending upon the dosage form employed and the route of administration utilized. For any RORγ modulator used in a method described herein, the therapeutically effective dose can be estimated initially from cell culture assays. A dose may be formulated in animal models to achieve a circulating plasma concentration range that includes the $IC_{50}$ (i.e., the concentration of RORγ modulator that achieves a half-maximal inhibition of symptoms) as determined in cell culture. Such information can be used to more accurately determine useful doses in humans. Levels in plasma may be measured, for example, by high performance liquid chromatography.

EXAMPLES

The following examples are offered for purposes of illustration, and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Example 1: Synthesis of Intermediate 4'-(1,1,1,3,3,3-hexafluoro-2-hydroxypropan-2-yl)-[1,1'-biphenyl]-4-carbaldehyde (4)

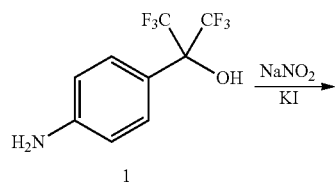

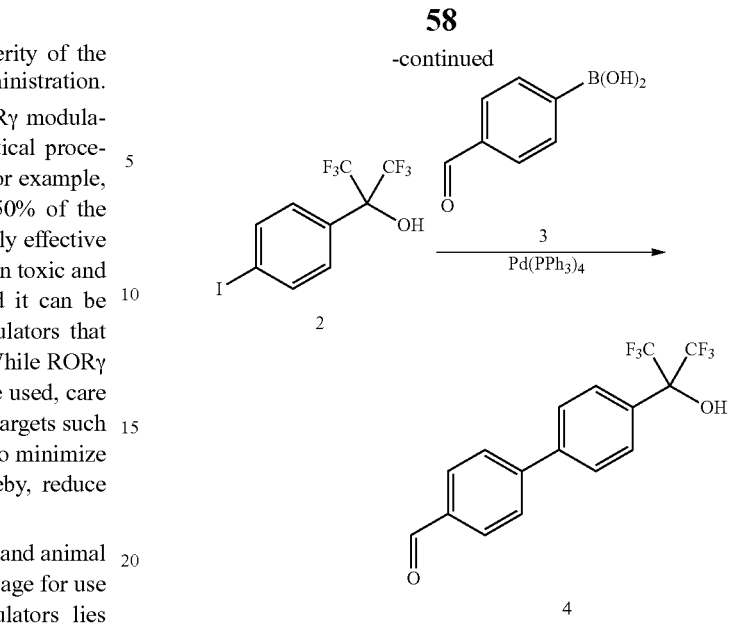

Step A: To a solution of 1 (15 g, 1.0 eq) in DMF (120 mL) was added a solution of $NaNO_2$ (4.4 g, 1.1 eq) in water (30 mL). The mixture was cooled to 0° C. for 15 minutes and 6N HCl (29 mL, 3.0 eq) was added dropwise to the reaction mixture for over 15 minutes at 0° C. The resulting mixture was stirred at 0° C. for 1 h. KI (10.1 g, 1.05 eq) was added with portions (over 15 minutes). The reaction mixture was stirred at 0° C. for 1 h, and then stirred at room temperature overnight. The reaction mixture was diluted with water (~500 mL) and extracted with EtOAc/Hexane (2:1, 3×150 mL). The combined organic phase was washed with $NaHSO_3$, water, and brine. The crude mixture was purified on a silica gel column to afford 2 (18.85 g, 88%) as a pale yellow oil.

Step B: To 2 (6.6 g, 1.0 eq), 3 (3.21 g, 1.2 eq), $Pd(PPh_3)_4$ (2.05 g, 0.1 eq), and $K_2CO_3$ (7.4 g, 3.0 eq) were combined in dioxane (150 mL) and water (40 mL). The mixture was flushed with $N_2$ for 5 minutes and then heated at 80° C. for 8 h under $N_2$. The reaction mixture was cooled and extracted with EtOAc (2×200 mL). The combined organic phase was washed with 1N HCl and brine. The crude mixture was purified on a silica gel column to afford the title compound 4 (4.6 g, 74%) as a white solid.

Synthesis Protocol A

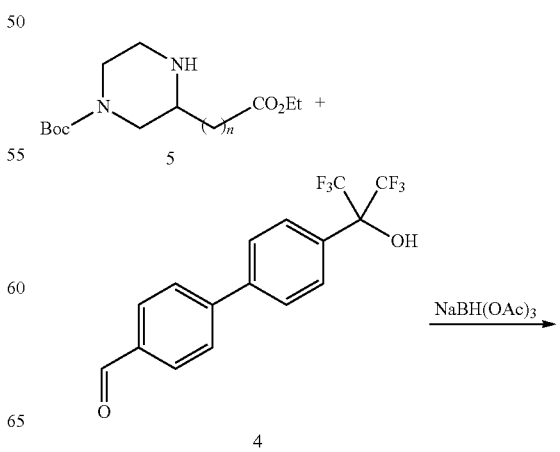

-continued

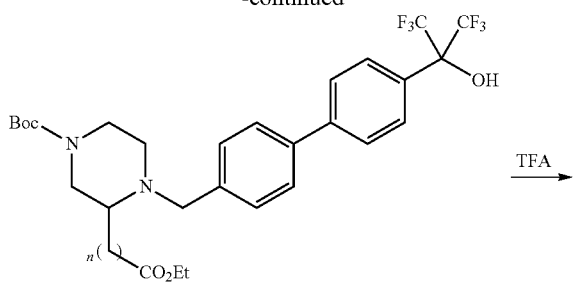

6

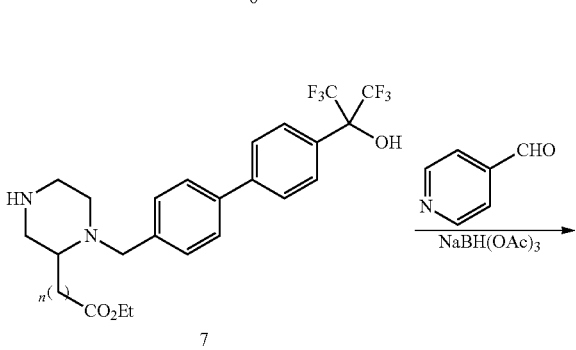

7

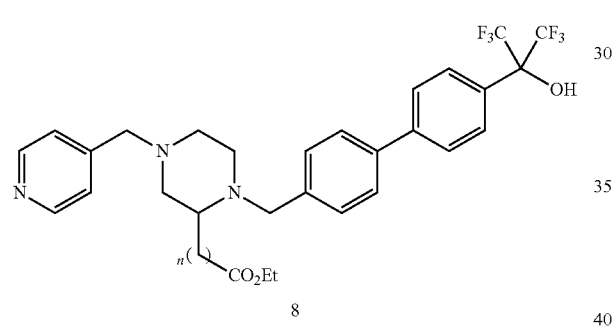

8

Boc-piperazine 5 (1.0 eq) and aldehyde 4 (1.0 eq) were dissolved in 1,2-DCE and TFA (0.2 eq) was added. The mixture was stirred at room temperature for 3 h and NaBH(OAc)$_3$ (3.0 eq) was then added. The resulting mixture was stirred at room temperature overnight. The reaction mixture was quenched with MeOH and washed with saturated NaHCO$_3$, water and brine. The crude mixture was purified on a silica gel column to afford compound 6.

Compound 6 was dissolved in CH$_2$Cl$_2$ and TFA (1:1). The mixture was stirred at room temperature for 2 h. The solvent was removed in vacuo. The residue was dissolved in CH$_2$Cl$_2$ and washed with saturated NaHCO$_3$ to afford compound 7.

4-Pyridine aldehyde (1.0 eq) and compound 7 (1.0 eq) were dissolved in 1,2-DCE and TFA (0.2 eq) was added. The mixture was stirred at room temperature for 3 h. NaBH(OAc)$_3$ (3.0 eq) was then added. The resulting mixture was stirred at room temperature overnight. The reaction mixture was quenched with MeOH and washed with saturated NaHCO$_3$, water and brine. The crude mixture was purified on a silica gel column to afford compound 8.

Example 2: Synthesis of ethyl 1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate (9)

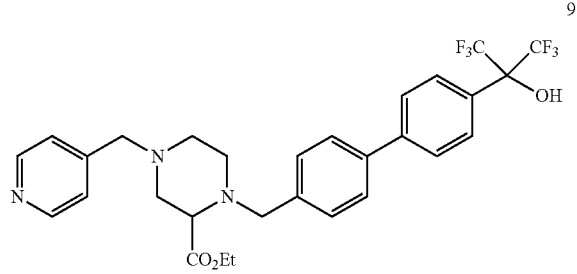 [SMILES: CCOC(=O)C1CN(Cc2ccncc2)CCN1Cc1ccc(-c2ccc(C(O)(C(F)(F)F)C(F)(F)F)cc2)cc1]

9

The title compound 9 was prepared as described in Synthesis Protocol A wherein n is 0. LC-MS: 582.4 [M+H]$^+$.

Example 3: Synthesis of ethyl 2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl) acetate (10)

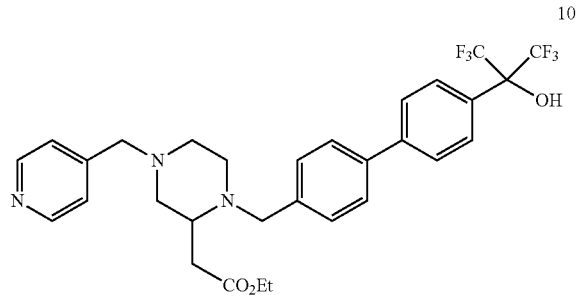 [SMILES: CCOC(=O)CC1CN(Cc2ccncc2)CCN1Cc1ccc(-c2ccc(C(O)(C(F)(F)F)C(F)(F)F)cc2)cc1]

10

The title compound 10 was prepared as described in Synthesis Protocol A wherein n is 1. LC-MS: 596.3 [M+H]$^+$.

Synthesis Protocol B

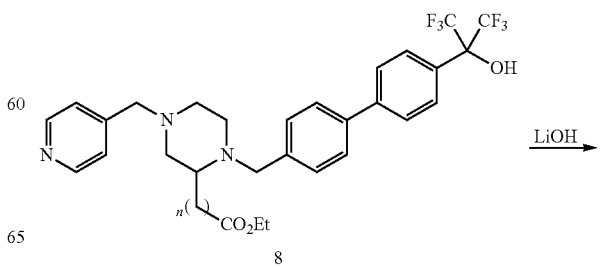

8

-continued

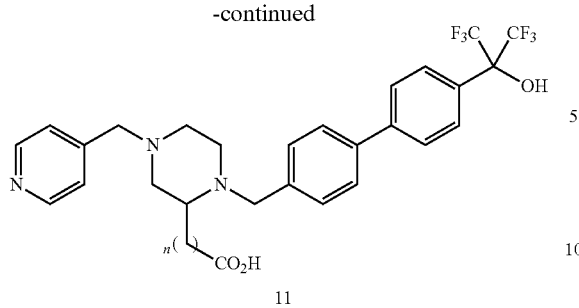

11

Compound 8 was treated with aqueous LiOH under standard conditions to afford the corresponding acid 11.

Example 4: Synthesis of 1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylic acid (12)

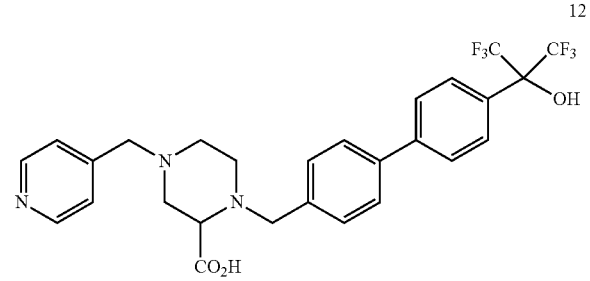 [SMILES: O=C(O)C1CN(Cc2ccncc2)CCN1Cc1ccc(-c2ccc(C(O)(C(F)(F)F)C(F)(F)F)cc2)cc1]

12

The title compound 12 was prepared as described in Synthesis Protocol B wherein n is 0. LC-MS: 554.4 [M+H]⁺.

Example 5: Synthesis of 2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetic acid (13)

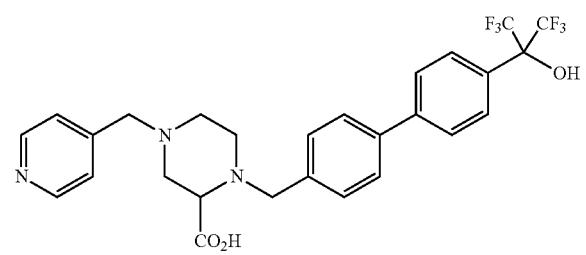

13

The title compound 13 was prepared as described in Synthesis Protocol B wherein n is 1. LC-MS: 568.3 [M+H]⁺.

Synthesis Protocol C

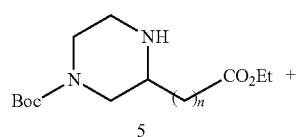

5

-continued

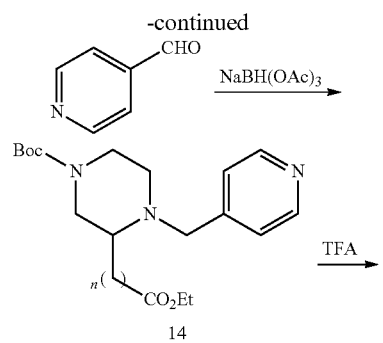

14

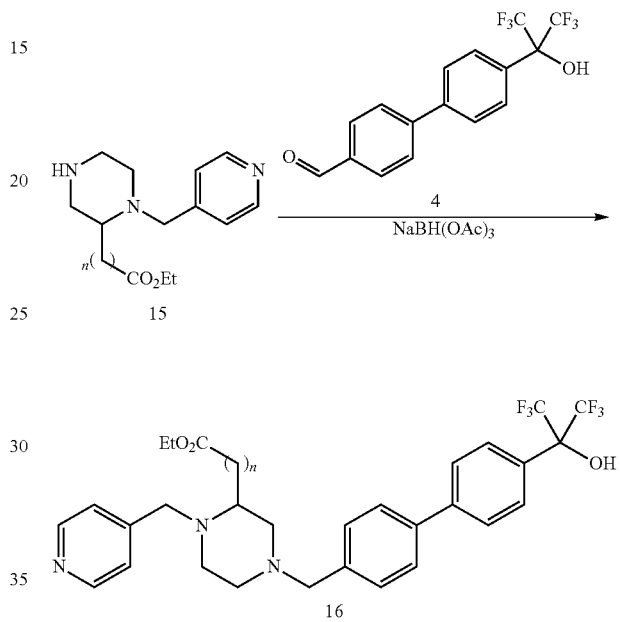

Step A: Boc-piperazine 5 (1.0 eq) and 4-pyridine aldehyde (1.0 eq) were dissolved in 1,2-DCE and TFA (0.2 eq) was added. The mixture was stirred at room temperature for 3 h and NaBH(OAc)₃ (3.0 eq) was then added. The resulting mixture was stirred at room temperature overnight. The reaction mixture was quenched with MeOH and washed with saturated NaHCO₃, water, and brine. The crude mixture was purified on a silica gel column to afford compound 14. Compound 14 was dissolved in CH₂Cl₂ and TFA (1:1). The mixture was stirred at room temperature for 2 h. The solvent was removed in vacuo. The residue was dissolved in CH₂Cl₂ and washed with saturated NaHCO₃ to afford compound 15.

Step B: Compound 4 (1.0 eq) and compound 15 (1.0 eq) were dissolved in 1,2-DCE and TFA (0.2 eq) was added. The mixture was stirred at room temperature for 3 h. NaBH(OAc)₃ (3.0 eq) was then added. The resulting mixture was stirred at room temperature overnight. The reaction mixture was quenched with MeOH and washed with saturated NaHCO₃, water, and brine. The crude mixture was purified on a silica gel column to afford compound 16.

Example 6: Synthesis of ethyl 4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate (17)

Example 8: Synthesis of 4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylic acid (20)

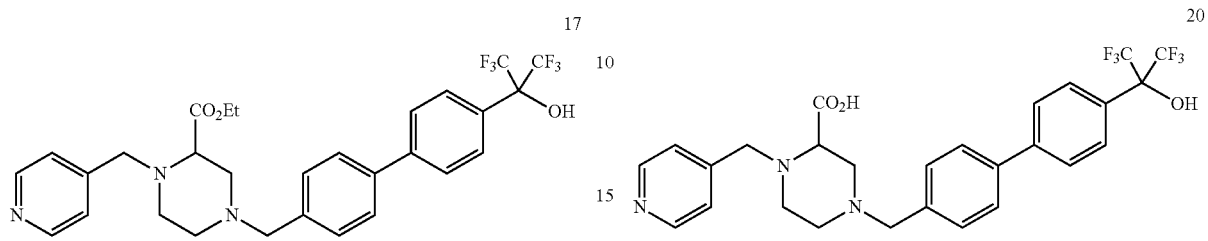

The title compound 17 was prepared as described in Synthesis Protocol C wherein n is 0. LC-MS: 582.4 [M+H]$^+$.

The title compound 20 was prepared as described in Synthesis Protocol D' wherein n is 0. LC-MS: 554.4 [M+H]$^+$.

Example 7: Synthesis of ethyl 2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate (18)

Example 9: Synthesis of 2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetic acid (21)

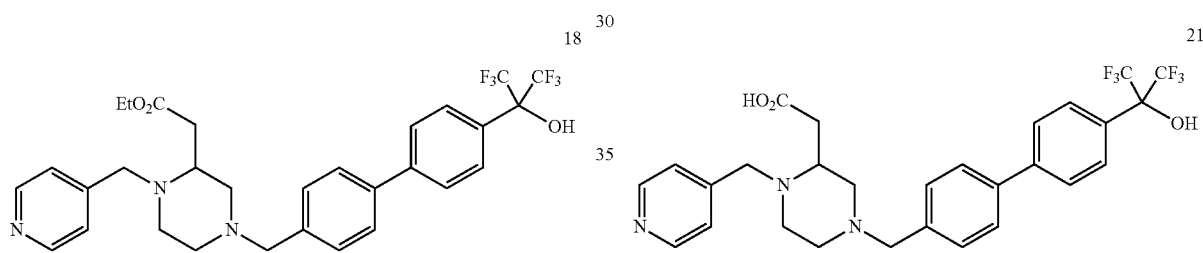

The title compound 18 was prepared as described in Synthesis Protocol C wherein n is 1. LC-MS: 596.3 [M+H]$^+$.

The title compound 21 was prepared as described in Synthesis Protocol B wherein n is 1. LC-MS: 568.3 [M+H]$^+$.

Synthesis Protocol D

Synthesis Protocol E

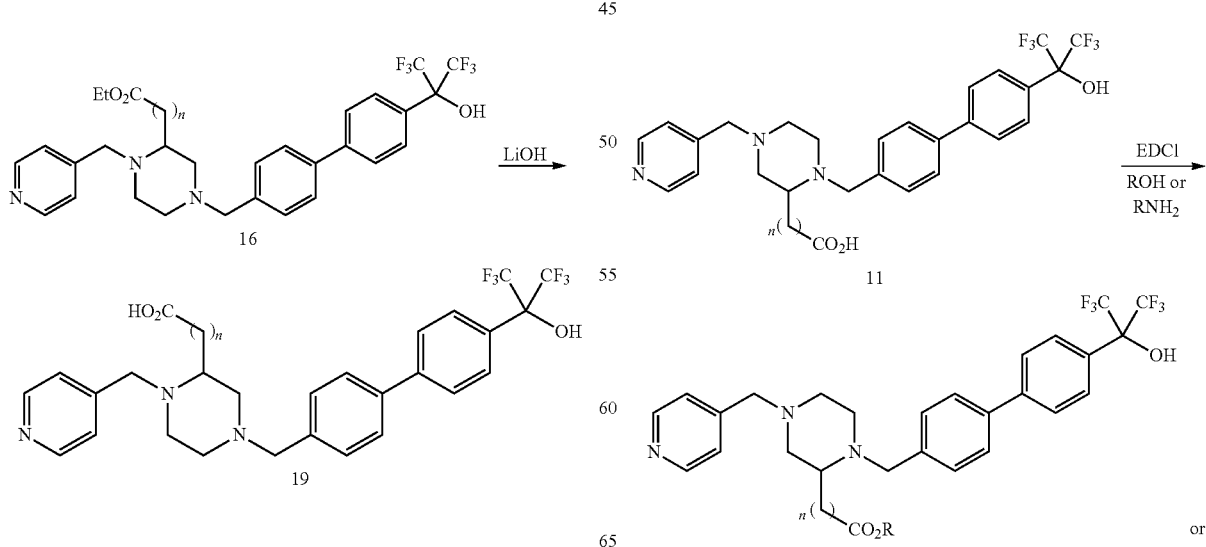

Compound 16 was treated with aqueous LiOH under standard conditions to afford the corresponding acid 19.

-continued

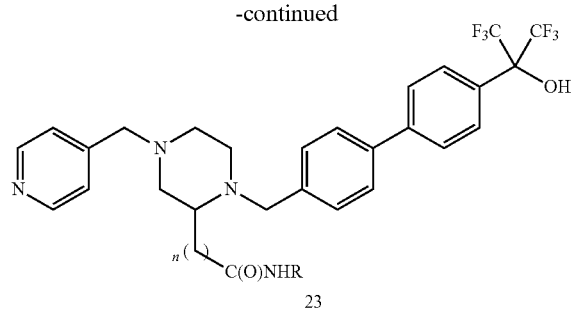

23

Compound 11 was coupled with ROH or RNH$_2$ in presence of EDCI to afford ester 22 or amide 23, respectively.

Example 10: Synthesis of 1-((4'-(1,1,1,3,3,3-hexafluoro-2-hydroxypropan-2-yl)-[1,1'-biphenyl]-4-yl)methyl)-N-isopropyl-4-(pyridin-4-ylmethyl)piperazine-2-carboxamide (24)

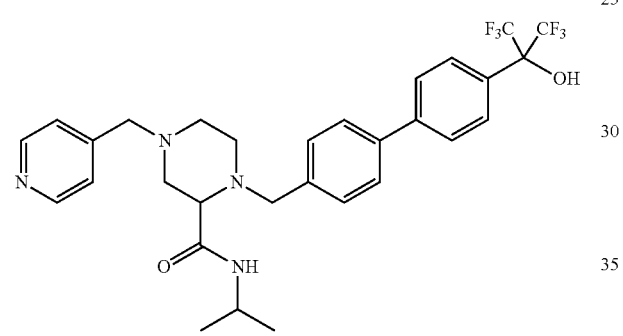

24

The title compound 24 was prepared as described in Synthesis Protocol E wherein n is 0. LC-MS: 595.2 [M+H]$^+$.

Example 11: Synthesis of 2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)-N-isopropylacetamide (25)

25

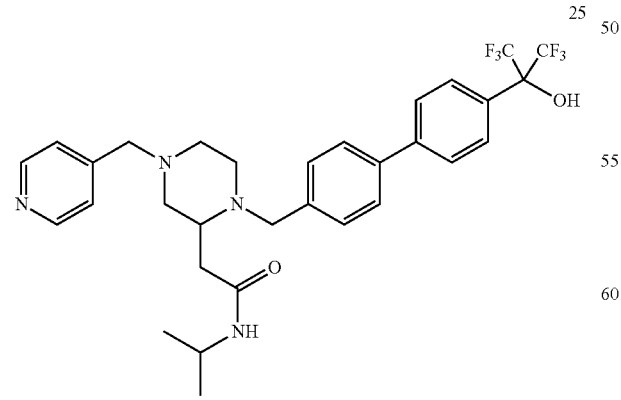

The title compound 25 was prepared as described in Synthesis Protocol E wherein n is 1. LC-MS: 609.2 [M+H]$^+$.

Synthesis Protocol F

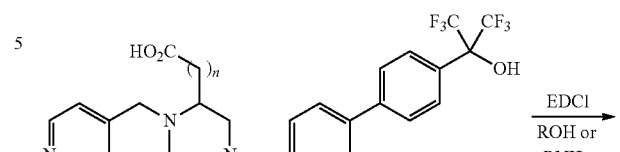

19

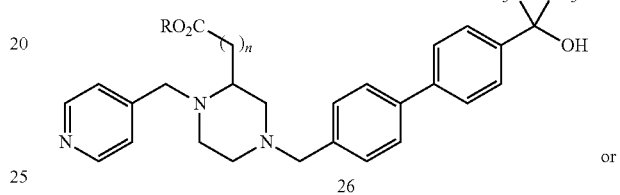

26 or

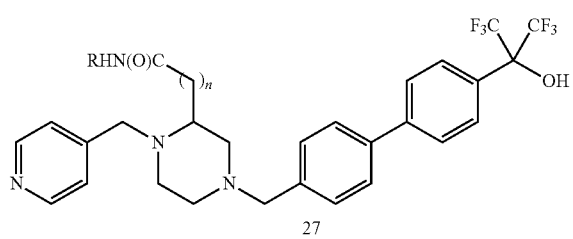

27

Compound 19 was coupled with ROH or RNH$_2$ in presence of EDCI to afford ester 26 or amide 27, respectively.

Example 12: Synthesis of 4-((4'-(1,1,1,3,3,3-hexafluoro-2-hydroxypropan-2-yl)-[1,1'-biphenyl]-4-yl)methyl)-N-isopropyl-1-(pyridin-4-ylmethyl)piperazine-2-carboxamide (28)

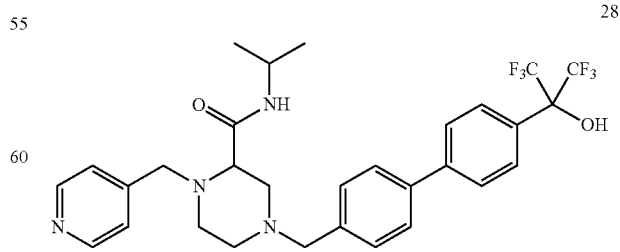

28

The title compound 28 was prepared as described in Synthesis Protocol F wherein n is 0. LC-MS: 595.3 [M+H]$^+$.

Example 13: Synthesis of 2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)-N-isopropylacetamide (29)

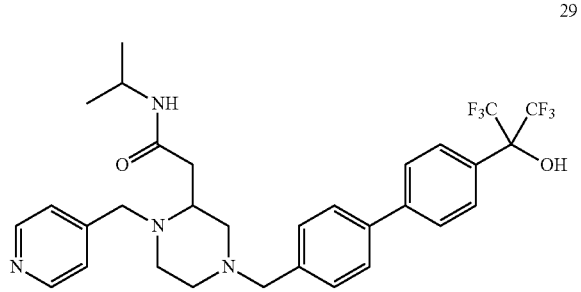 [SMILES: CC(C)NC(=O)CC1CN(Cc2ccc(-c3ccc(C(O)(C(F)(F)F)C(F)(F)F)cc3)cc2)CCN1Cc1ccncc1]

The title compound 29 was prepared as described in Synthesis Protocol F wherein n is 1. LC-MS: 609.3 [M+H]$^+$.

Example 14: Synthesis of isopropyl 2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate (30)

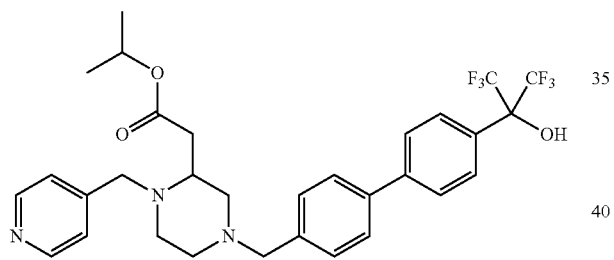

The title compound 30 was prepared as described in Synthesis Protocol F wherein n is 1. LC-MS: 610.3 [M+H]$^+$.

Example 15: Synthesis of 2-hydroxyethyl 2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate (31)

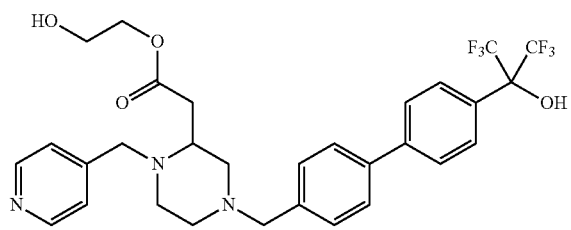

The title compound 31 was prepared as described in Synthesis Protocol F wherein n is 1. LC-MS: 612.4 [M+H]$^+$.

Example 16: Synthesis of 2-ethoxyethyl 2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate (32)

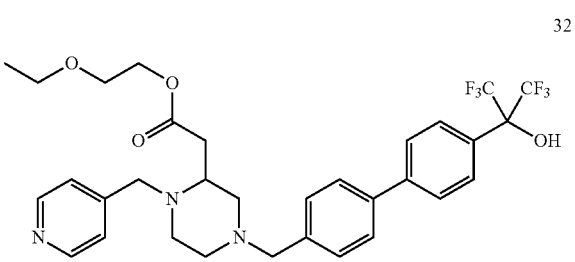 [SMILES: CCOCCOC(=O)CC1CN(Cc2ccc(-c3ccc(C(O)(C(F)(F)F)C(F)(F)F)cc3)cc2)CCN1Cc1ccncc1]

The title compound 32 was prepared as described in Synthesis Protocol F wherein n is 1. LC-MS: 640.1 [M+H]$^+$.

Example 17: Synthesis of 2-aminoethyl 2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate hydrochloride (33)

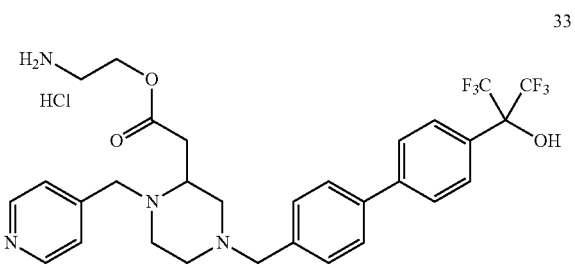 [SMILES: NCCOC(=O)CC1CN(Cc2ccc(-c3ccc(C(O)(C(F)(F)F)C(F)(F)F)cc3)cc2)CCN1Cc1ccncc1 ; Cl]

Step A. The title compound 33 was prepared as described in Synthesis Protocol F wherein Compound 29 from Example 9 (1.0 eq) in DMF was the starting material to which was added EDCI (2.5 eq) and tert-butyl (2-hydroxyethyl)carbamate (10 eq). The mixture was stirred at room temperature overnight. The crude mixture was purified on silica gel column to afford the ester intermediate 2-((tert-butoxycarbonyl)amino)ethyl 2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate.

Step B. The ester was treated with 4N HCl in dioxane to afford the title compound. LC-MS: 611.3 [M+H]$^+$.

Example 18: Synthesis of ethyl 2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate (35)

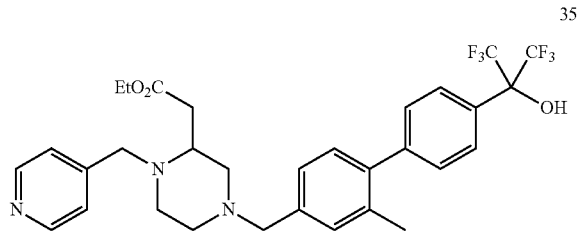 [SMILES: CCOC(=O)CC1CN(Cc2ccc(-c3ccc(C(O)(C(F)(F)F)C(F)(F)F)cc3)c(C)c2)CCN1Cc1ccncc1]

Step A: The aldehyde intermediate 4'-(1,1,1,3,3,3-hexafluoro-2-hydroxypropan-2-yl)-2-methyl-[1,1'-biphenyl]-4-carbaldehyde (compound 34) was synthesized as described in Step B of Example 1, but substituting (4-formyl-2-methylphenyl)boronic acid for compound 3.

Step B: The title compound was prepared as described in Synthesis Protocol C, but substituting 4'-(1,1,1,3,3,3-hexafluoro-2-hydroxypropan-2-yl)-2-methyl-[1,1'-biphenyl]-4-carbaldehyde (compound 34) for compound 4 and wherein n is 1. LC-MS: 610.2 [M+H]$^+$.

Example 19: Synthesis of ethyl (S)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate (47)

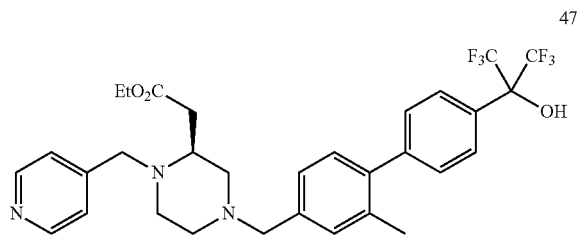 [SMILES: CCOC(=O)C[C@H]1CN(Cc2ccc(-c3ccc(C(O)(C(F)(F)F)C(F)(F)F)cc3)c(C)c2)CCN1Cc1ccncc1]

To a suspension solution of commercially available (R)-piperazine-2-carboxylic acid dihydrochloride 36 (25 g, 1.0 eq) in 350 mL dioxane and 200 mL DMF was added Et$_3$N (83.7 mL, 5.0 eq) and benzyl bromide (73 mL, 5.0 eq). The resulting mixture was heated at 100° C. for 8 h. After the reaction cooled to room temperature, the mixture was diluted with water (1 L), then extracted with EtOAC/Hexane (1:1, 3×500 mL). The combined organic phase was washed with saturated NaHCO$_3$ (200 mL), water (3×500 mL) and brine (500 mL). The crude mixture was purified on silica gel column to provide benzyl (R)-1,4-dibenzylpiperazine-2-carboxylate 37 (22.18 g, 45%) oil.

To a solution of benzyl (R)-1,4-dibenzylpiperazine-2-carboxylate 37 (19 g, 1.0 eq) in THF (80 mL) was added dropwise 1M LAH (72 mL, 1.5 eq) over 15 mins at 0° C. under N$_2$. The resulting mixture was stirred at 0° C. for 30 min, then room temperature for 1 h. The reaction mixture was cooled with ice-water bath, quenched with water (4 mL), NaOH (20%, 4 mL) and water 6 mL. The reaction was diluted with 100 mL acetate and 100 mL hexane, the inorganic solid was filtered off, and washed with acetate (2×30 mL). The combined organic phase was washed with brine and concentrate in vacuum to afford oil. The oil was dissolved in 50 mL DCM, slowly added 2M HCl in ether (80 mL), the mixture was stirred at room temperature for 20 min. The white solid was collected by filtration to afford (R)-(1,4-dibenzylpiperazin-2-yl)methanol 38 (17.3 g, 97%) as dihydrochloride salt.

(R)-(1,4-Dibenzylpiperazin-2-yl)methanol dihydrochloride 38 (17.3 g, 1.0 eq) was suspended in 120 mL SOCl$_2$. The mixture was heated at 60° C. for 4 h. The excess SOCl$_2$ was removed in vacuo, the residue was diluted with 200 mL ice water. To the mixture was added solid Na$_2$CO$_3$ to adjust pH 9, then extracted with 3×50 mL DCM to afford pale yellow oil (R)-1,4-dibenzyl-2-(chloromethyl)piperazine 39 (13.6 g, 93%) which was used without purification.

(R)-1,4-Dibenzyl-2-(chloromethyl)piperazine 39 (13.6 g, 1.0 eq) was dissolved in 100 mL DMSO, to which was added NaCN (7.0 g, 2.5 eq) and KI (200 mg). The resulting mixture was heated to 65° C. for 3 h. The reaction mixture was diluted with ice-water (300 mL), then extracted with EtOAc/Hexane (1:1, 2×120 mL). The combined organic phase was washed with saturated NaHCO$_3$ and brine to afford (S)-2-(1,4-dibenzylpiperazin-2-yl)acetonitrile as a pale yellow oil 40 (13.2 g, 100%) which was used without purification.

(S)-2-(1,4-Dibenzylpiperazin-2-yl)acetonitrile 40 (13.2 g, 1.0 eq) was dissolved in 120 mL absolute EtOH. To the solution was carefully added 80 mL H$_2$SO$_4$. The reaction mixture was heated at 110° C. for 3 h, then diluted with 500 g ice. The mixture was basified to pH 8-9 by adding 10% NaOH at 0° C. The product was extracted with EtOAc/Hexane (1:1, 3×150 mL) and dried in vacuo to provide ethyl (S)-2-(1,4-dibenzylpiperazin-2-yl)acetate as a pale yellow oil 41 (14.6 g, 96%) which was used without purification.

Ethyl (S)-2-(1,4-dibenzylpiperazin-2-yl)acetate 41 (14.6 g, 1.0 eq) was dissolved in 100 mL EtOH, added 2M HCl in EtOH (75 mL) and Pd/C (2.5 g, 10%). The mixture was hydrogenated at 60 PSI H$_2$ for 8 h. The catalyst was removed, and the mixture was concentrated in vacuo. The residue white solid was washed with EtOAC/Hexane (1:5, 2×20 mL) to afford ethyl (S)-2-(piperazin-2-yl)acetate 42 (9.2 g, 91%) as a dihydrochloride salt.

Ethyl (S)-2-(piperazin-2-yl)acetate 42 (9.2 g, 1.0 eq) was dissolved in THF (50 mL) and water (50 mL). To the mixture was added 2M K$_2$CO$_3$ to adjust pH 9-10 at 0° C., then Boc-ON (2-(tert-butoxycarbonyloxyimino)-2-phenylacetonitrile) (9.4 g, 1.0 eq) was added. The resulting mixture was stirred at 0° C. for 2 h, then rt. overnight. THF was removed in vacuo, then extracted with acetate (3×100 mL). The mixture was purified on silica gel column to provide oil tert-butyl (S)-3-(2-ethoxy-2-oxoethyl)piperazine-1-carboxylate 43 (6.65 g, 59%)

tert-Butyl (S)-3-(2-ethoxy-2-oxoethyl)piperazine-1-carboxylate 43 (1.0 eq) and 4-pyridine aldehyde (1.0 eq) were dissolved in 1,2-DCE to which TFA (0.2 eq) was added. The mixture was stirred at room temperature for 3 h after which NaBH(OAc)$_3$ (3.0 eq) was added. The resulting mixture was stirred at room temperature overnight. The reaction mixture was quenched with MeOH and washed with saturated NaHCO$_3$, water, and brine. The crude mixture was purified on a silica gel column to afford tert-butyl (S)-3-(2-ethoxy-2-oxoethyl)-4-(pyridin-4-ylmethyl)piperazine-1-carboxylate 44.

tert-Butyl (S)-3-(2-ethoxy-2-oxoethyl)-4-(pyridin-4-ylmethyl)piperazine-1-carboxylate 44 was dissolved in CH₂Cl₂ and TFA (1:1). The mixture was stirred at room temperature for 2 h. The solvent was removed in vacuo. The residue was dissolved in CH₂Cl₂ and washed with saturated NaHCO₃ to afford ethyl (S)-2-(1-(pyridin-4-ylmethyl)piperazin-2-yl)acetate 45.

4'-(1,1,1,3,3,3-Hexafluoro-2-hydroxypropan-2-yl)-2-methyl-[1,1'-biphenyl]-4-carbaldehyde (compound 34 described in Example 18) (1.0 eq) and ethyl (S)-2-(1-(pyridin-4-ylmethyl)piperazin-2-yl)acetate 45 (1.0 eq) were dissolved in 1,2-DCE and TFA (0.2 eq) was added. The mixture was stirred at room temperature for 3 h. NaBH(OAc)₃ (3.0 eq) was then added. The resulting mixture was stirred at room temperature overnight. The reaction mixture was quenched with MeOH and washed with saturated NaHCO₃, water, and brine. The crude mixture was purified on a silica gel column to afford the title compound 47. LC-MS: 610.5 [M+H]⁺.

Example 20: Synthesis of ethyl (S)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate (48)

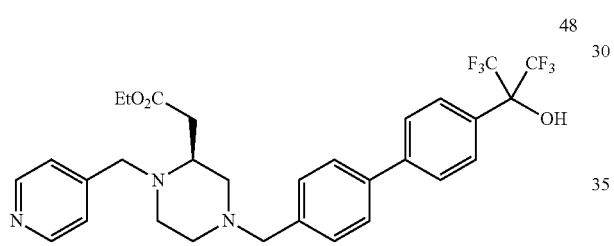

The title compound was prepared as described in Example 19, but substituting aldehyde compound 4 for 4'-(1,1,1,3,3,3-hexafluoro-2-hydroxypropan-2-yl)-2-methyl-[1,1'-biphenyl]-4-carbaldehyde in the final reaction step. LC-MS: 596.3 [M+H]⁺.

Example 21: Synthesis of ethyl (R)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate (49)

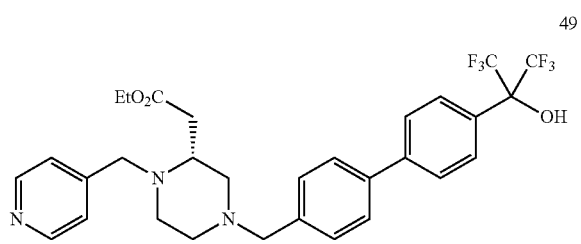 [SMILES: CCOC(=O)C[C@@H]1CN(Cc2ccc(-c3ccc(C(O)(C(F)(F)F)C(F)(F)F)cc3)cc2)CCN1Cc1ccncc1]

The title compound was prepared as described in Example 19, but substituting commercially available (S)-piperazine-2-carboxylic acid for (R)-piperazine-2-carboxylic acid dihydrochloride in the first reaction step, and substituting aldehyde compound 4 for 4'-(1,1,1,3,3,3-hexafluoro-2-hydroxypropan-2-yl)-2-methyl-[1,1'-biphenyl]-4-carbaldehyde in the final reaction step. LC-MS: 596.4 [M+H]⁺.

Example 22: Synthesis of (S)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetic acid (50)

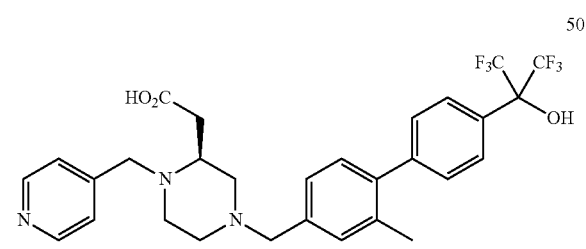

Compound 47 of Example 19 was treated with 1N LiOH.H₂O solution in methanol to afford the title compound. LC-MS: 582.4 [M+H]⁺.

Example 23: Synthesis of 2-ethoxyethyl (S)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate (51)

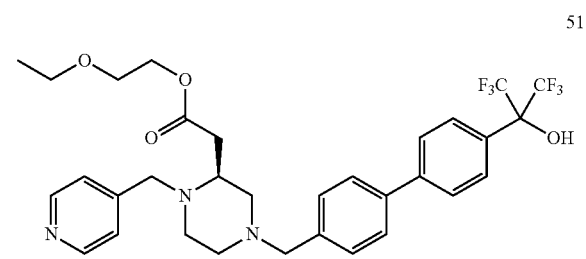 [SMILES: CCOCCOC(=O)C[C@H]1CN(Cc2ccc(-c3ccc(C(O)(C(F)(F)F)C(F)(F)F)cc3)cc2)CCN1Cc1ccncc1]

Compound 48 of Example 20 was treated with 1N LiOH.H₂O in methanol to provide (S)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetic acid. The acetic acid intermediate from the previous step (1.0 eq) and 2-ethoxyethan-1-ol (10 eq) was dissolved in DMF. To the mixture was added EDCI (2.5 eq). The mixture was stirred at RT overnight, and then heated at 55° C. for 8 h. The crude mixture was purified on silica gel column to afford the title compound. LC-MS: 640.5 [M+H]⁺.

Example 24: Synthesis of Additional Examples

Table 1 shows additional compounds of Formula (I) that are prepared using the protocols and intermediates described above.

TABLE 1

| Compound No. | Structure | Compound name | Synthetic Protocol/ Intermediates to be used |
|---|---|---|---|
| 52 | 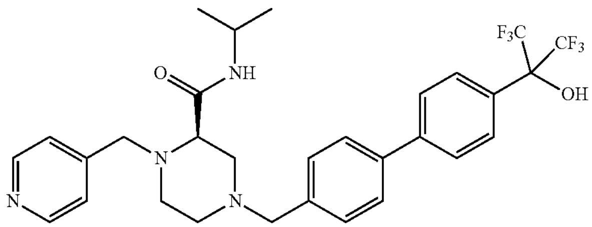 [SMILES: CC(C)NC(=O)[C@H]1CN(Cc2ccc(-c3ccc(C(O)(C(F)(F)F)C(F)(F)F)cc3)cc2)CCN1Cc1ccncc1] | (R)-4-((4'-(1,1,1,3,3,3-hexafluoro-2-hydroxypropan-2-yl)-[1,1'-biphenyl]-4-yl)methyl)-N-isopropyl-1-(pyridin-4-ylmethyl)piperazine-2-carboxamide | Protocol F using 179 |
| 53 | 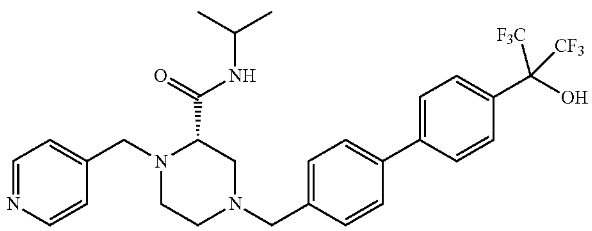 [SMILES: CC(C)NC(=O)[C@@H]1CN(Cc2ccc(-c3ccc(C(O)(C(F)(F)F)C(F)(F)F)cc3)cc2)CCN1Cc1ccncc1] | (S)-4-((4'-(1,1,1,3,3,3-hexafluoro-2-hydroxypropan-2-yl)-[1,1'-biphenyl]-4-yl)methyl)-N-isopropyl-1-(pyridin-4-ylmethyl)piperazine-2-carboxamide | Protocol F using 180 |
| 54 | 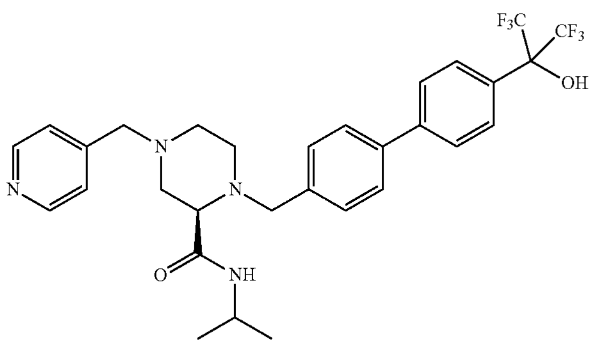 [SMILES: CC(C)NC(=O)[C@H]1CN(Cc2ccncc2)CCN1Cc1ccc(-c2ccc(C(O)(C(F)(F)F)C(F)(F)F)cc2)cc1] | (R)-1-((4'-(1,1,1,3,3,3-hexafluoro-2-hydroxypropan-2-yl)-[1,1'-biphenyl]-4-yl)methyl)-N-isopropyl-4-(pyridin-4-ylmethyl)piperazine-2-carboxamide | Protocol E using 181 |
| 55 | 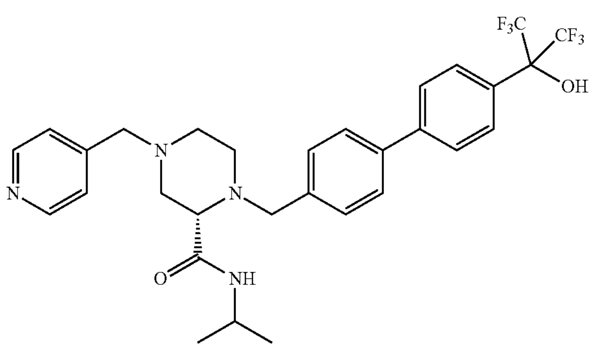 [SMILES: CC(C)NC(=O)[C@@H]1CN(Cc2ccncc2)CCN1Cc1ccc(-c2ccc(C(O)(C(F)(F)F)C(F)(F)F)cc2)cc1] | (S)-1-((4'-(1,1,1,3,3,3-hexafluoro-2-hydroxypropan-2-yl)-[1,1'-biphenyl]-4-yl)methyl)-N-isopropyl-4-(pyridin-4-ylmethyl)piperazine-2-carboxamide | Protocol E using 181 |
| 56 | 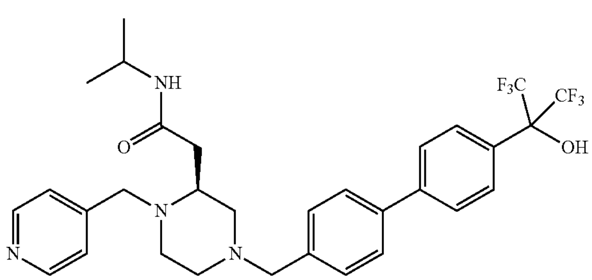 [SMILES: CC(C)NC(=O)C[C@H]1CN(Cc2ccc(-c3ccc(C(O)(C(F)(F)F)C(F)(F)F)cc3)cc2)CCN1Cc1ccncc1] | (S)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)-N-isopropylacetamide | Protocol F using 183 |

TABLE 1-continued

| Compound No. | Structure | Compound name | Synthetic Protocol/ Intermediates to be used |
|---|---|---|---|
| 57 | 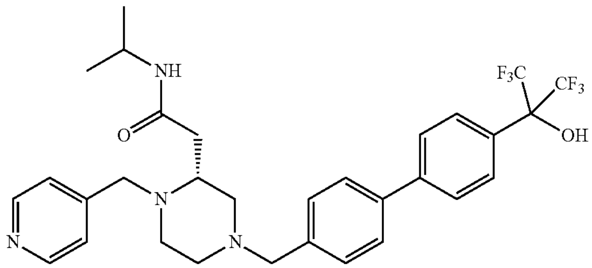 [SMILES: CC(C)NC(=O)C[C@@H]1CN(Cc2ccc(-c3ccc(C(O)(C(F)(F)F)C(F)(F)F)cc3)cc2)CCN1Cc1ccncc1] | (R)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)-N-isopropylacetamide | Protocol F using 184 |
| 58 | 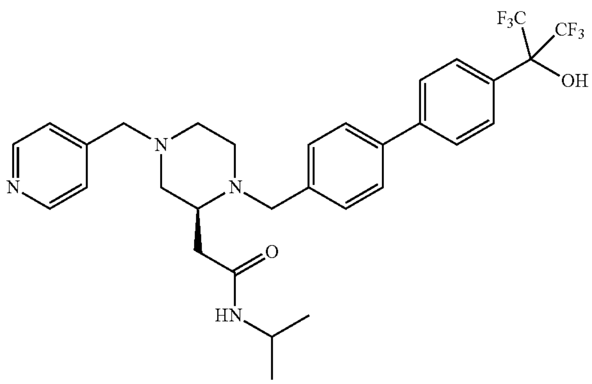 [SMILES: CC(C)NC(=O)C[C@H]1CN(Cc2ccncc2)CCN1Cc1ccc(-c2ccc(C(O)(C(F)(F)F)C(F)(F)F)cc2)cc1] | (S)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)-N-isopropylacetamide | Protocol E using 185 |
| 59 | 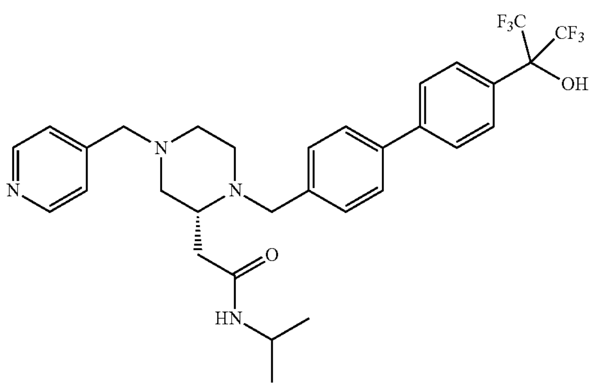 [SMILES: CC(C)NC(=O)C[C@@H]1CN(Cc2ccncc2)CCN1Cc1ccc(-c2ccc(C(O)(C(F)(F)F)C(F)(F)F)cc2)cc1] | (R)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)-N-isopropylacetamide | Protocol E using 186 |
| 60 | 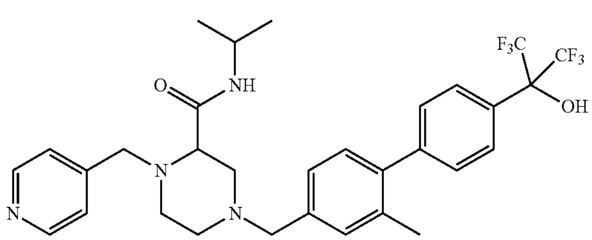 [SMILES: Cc1cc(CN2CCN(Cc3ccncc3)C(C(=O)NC(C)C)C2)ccc1-c1ccc(C(O)(C(F)(F)F)C(F)(F)F)cc1] | 4-((4'-(1,1,1,3,3,3-hexafluoro-2-hydroxypropan-2-yl)-2-methyl-[1,1'-biphenyl]-4-yl)methyl)-N-isopropyl-1-(pyridin-4-ylmethyl)piperazine-2-carboxamide | Protocol F using 187 |
| 61 | 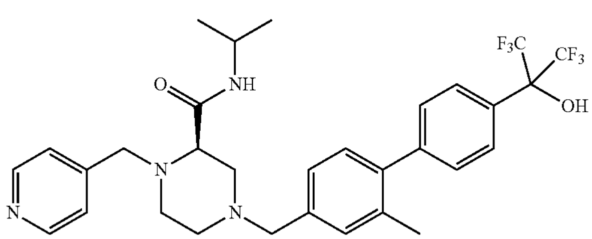 [SMILES: Cc1cc(CN2CCN(Cc3ccncc3)[C@@H](C(=O)NC(C)C)C2)ccc1-c1ccc(C(O)(C(F)(F)F)C(F)(F)F)cc1] | (R)-4-((4'-(1,1,1,3,3,3-hexafluoro-2-hydroxypropan-2-yl)-2-methyl-[1,1'-biphenyl]-4-yl)methyl)-N-isopropyl-1-(pyridin-4-ylmethyl)piperazine-2-carboxamide | Protocol F using 188 |

TABLE 1-continued

| Compound No. | Structure | Compound name | Synthetic Protocol/ Intermediates to be used |
|---|---|---|---|
| 62 | 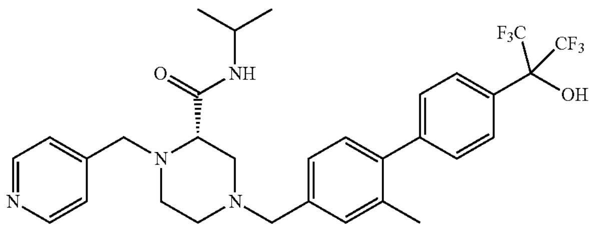 | (S)-4-((4'-(1,1,1,3,3,3-hexafluoro-2-hydroxypropan-2-yl)-2-methyl-[1,1'-biphenyl]-4-yl)methyl)-N-isopropyl-1-(pyridin-4-ylmethyl)piperazine-2-carboxamide | Protocol F using 189 |
| 63 | 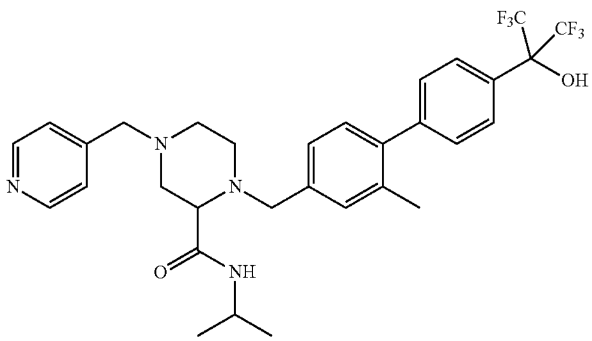 [SMILES: Cc1cc(CN2CCN(Cc3ccncc3)CC2C(=O)NC(C)C)ccc1-c1ccc(C(O)(C(F)(F)F)C(F)(F)F)cc1] | 1-((4'-(1,1,1,3,3,3-hexafluoro-2-hydroxypropan-2-yl)-2-methyl-[1,1'-biphenyl]-4-yl)methyl)-N-isopropyl-4-(pyridin-4-ylmethyl)piperazine-2-carboxamide | Protocol E using 190 |
| 64 | 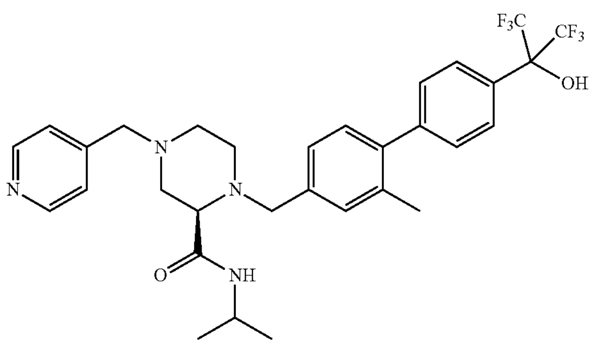 [SMILES: Cc1cc(CN2CCN(Cc3ccncc3)C[C@@H]2C(=O)NC(C)C)ccc1-c1ccc(C(O)(C(F)(F)F)C(F)(F)F)cc1] | (R)-1-((4'-(1,1,1,3,3,3-hexafluoro-2-hydroxypropan-2-yl)-2-methyl-[1,1'-biphenyl]-4-yl)methyl)-N-isopropyl-4-(pyridin-4-ylmethyl)piperazine-2-carboxamide | Protocol E using 191 |
| 65 | 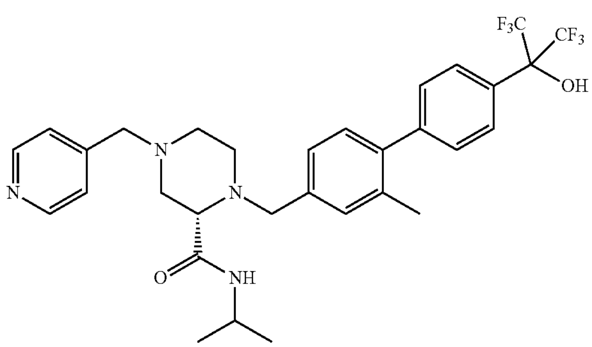 | (S)-1-((4'-(1,1,1,3,3,3-hexafluoro-2-hydroxypropan-2-yl)-2-methyl-[1,1'-biphenyl]-4-yl)methyl)-N-isopropyl-4-(pyridin-4-ylmethyl)piperazine-2-carboxamide | Protocol E using 192 |
| 66 | 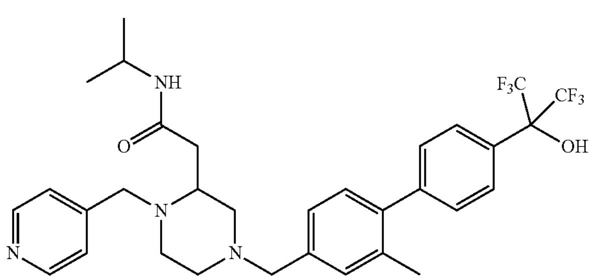 [SMILES: Cc1cc(CN2CCN(Cc3ccncc3)C(CC(=O)NC(C)C)C2)ccc1-c1ccc(C(O)(C(F)(F)F)C(F)(F)F)cc1] | 2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)-N-isopropylacetamide | Protocol F using 193 |

TABLE 1-continued

| Compound No. | Structure | Compound name | Synthetic Protocol/ Intermediates to be used |
|---|---|---|---|
| 67 | 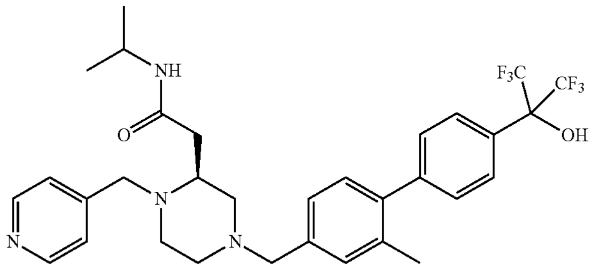 [SMILES: Cc1cc(CN2CCN(Cc3ccncc3)[C@@H](CC(=O)NC(C)C)C2)ccc1-c1ccc(C(O)(C(F)(F)F)C(F)(F)F)cc1] | (S)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)-N-isopropylacetamide | Protocol F using 50 |
| 68 | 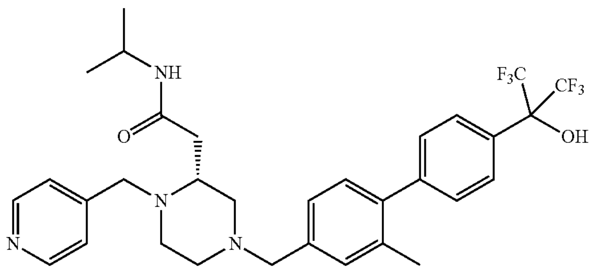 [SMILES: Cc1cc(CN2CCN(Cc3ccncc3)[C@H](CC(=O)NC(C)C)C2)ccc1-c1ccc(C(O)(C(F)(F)F)C(F)(F)F)cc1] | (R)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)-N-isopropylacetamide | Protocol F using 194 |
| 69 | 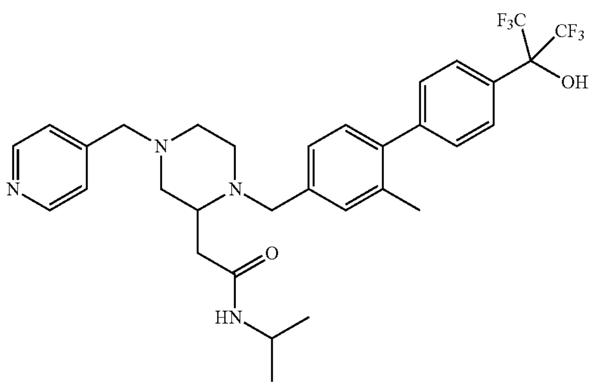 [SMILES: Cc1cc(CN2CCN(Cc3ccncc3)CC2CC(=O)NC(C)C)ccc1-c1ccc(C(O)(C(F)(F)F)C(F)(F)F)cc1] | 2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)-N-isopropylacetamide | Protocol E using 195 |
| 70 | 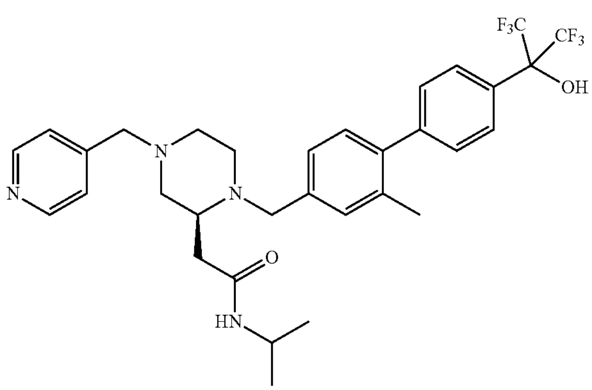 [SMILES: Cc1cc(CN2CCN(Cc3ccncc3)C[C@@H]2CC(=O)NC(C)C)ccc1-c1ccc(C(O)(C(F)(F)F)C(F)(F)F)cc1] | (S)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)-N-isopropylacetamide | Protocol E using 196 |

TABLE 1-continued

| Compound No. | Structure | Compound name | Synthetic Protocol/ Intermediates to be used |
|---|---|---|---|
| 71 | 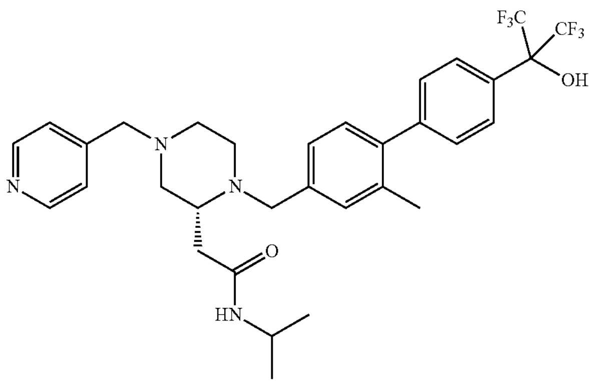 [SMILES: Cc1cc(CN2CCN(Cc3ccncc3)C[C@H]2CC(=O)NC(C)C)ccc1-c1ccc(C(O)(C(F)(F)F)C(F)(F)F)cc1] | (R)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)-N-isopropylacetamide | Protocol E using 197 |
| 72 | 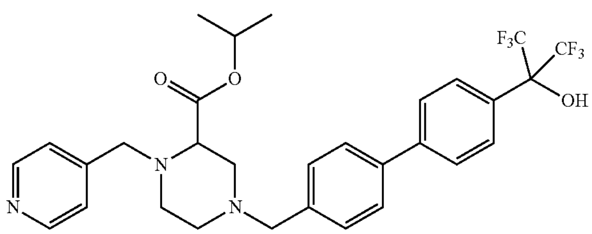 [SMILES: CC(C)OC(=O)C1CN(Cc2ccc(-c3ccc(C(O)(C(F)(F)F)C(F)(F)F)cc3)cc2)CCN1Cc1ccncc1] | isopropyl 4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 20 |
| 73 | 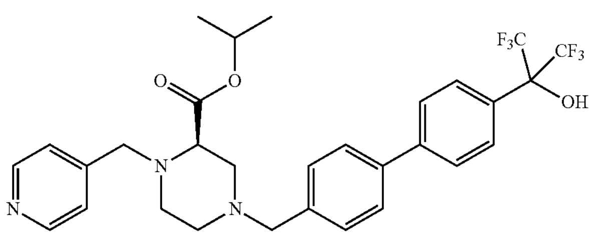 [SMILES: CC(C)OC(=O)[C@H]1CN(Cc2ccc(-c3ccc(C(O)(C(F)(F)F)C(F)(F)F)cc3)cc2)CCN1Cc1ccncc1] | isopropyl (R)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 179 |
| 74 | 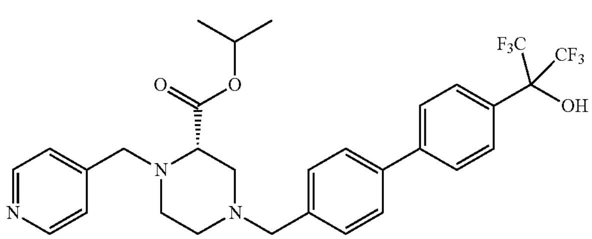 [SMILES: CC(C)OC(=O)[C@@H]1CN(Cc2ccc(-c3ccc(C(O)(C(F)(F)F)C(F)(F)F)cc3)cc2)CCN1Cc1ccncc1] | isopropyl (S)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 180 |
| 75 | 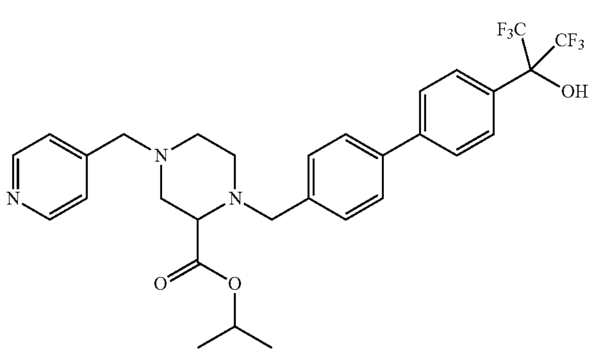 [SMILES: CC(C)OC(=O)C1CN(Cc2ccncc2)CCN1Cc1ccc(-c2ccc(C(O)(C(F)(F)F)C(F)(F)F)cc2)cc1] | isopropyl (R)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 12 |

TABLE 1-continued

| Compound No. | Structure | Compound name | Synthetic Protocol/ Intermediates to be used |
|---|---|---|---|
| 76 | 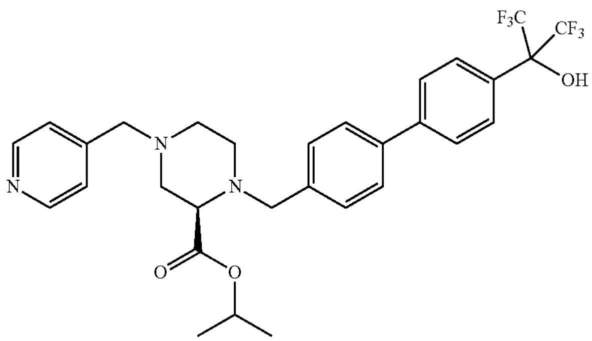 [SMILES: CC(C)OC(=O)[C@H]1CN(Cc2ccncc2)CCN1Cc1ccc(-c2ccc(C(O)(C(F)(F)F)C(F)(F)F)cc2)cc1] | isopropyl (R)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 181 |
| 77 | 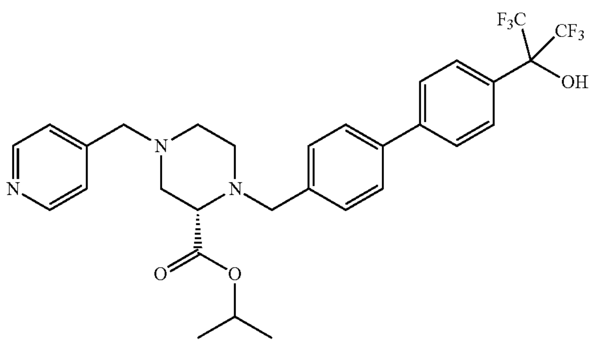 [SMILES: CC(C)OC(=O)[C@@H]1CN(Cc2ccncc2)CCN1Cc1ccc(-c2ccc(C(O)(C(F)(F)F)C(F)(F)F)cc2)cc1] | isopropyl (S)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 182 |
| 78 | 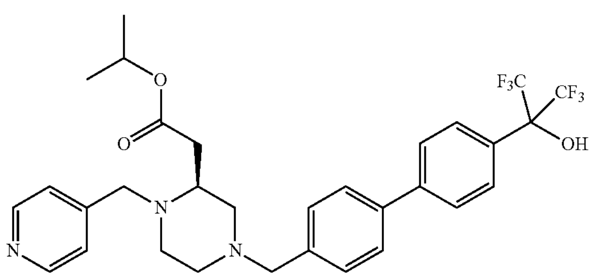 [SMILES: CC(C)OC(=O)C[C@H]1CN(Cc2ccc(-c3ccc(C(O)(C(F)(F)F)C(F)(F)F)cc3)cc2)CCN1Cc1ccncc1] | isopropyl (S)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate | Protocol F using 183 |
| 79 | 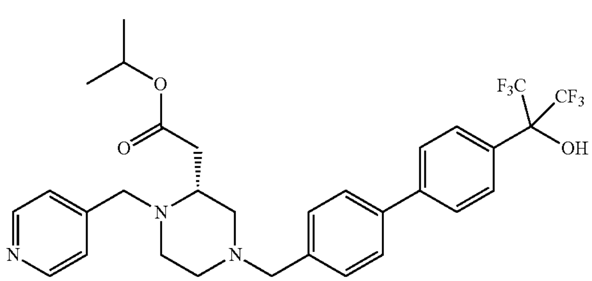 [SMILES: CC(C)OC(=O)C[C@@H]1CN(Cc2ccc(-c3ccc(C(O)(C(F)(F)F)C(F)(F)F)cc3)cc2)CCN1Cc1ccncc1] | isopropyl (R)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate | Protocol F using 184 |

TABLE 1-continued

| Compound No. | Structure | Compound name | Synthetic Protocol/ Intermediates to be used |
| --- | --- | --- | --- |
| 80 | 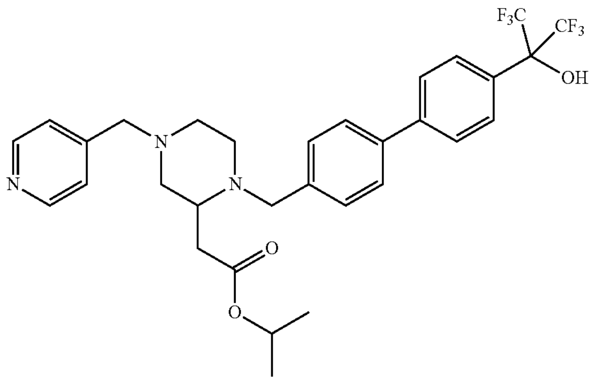 | isopropyl 2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 13 |
| 81 | 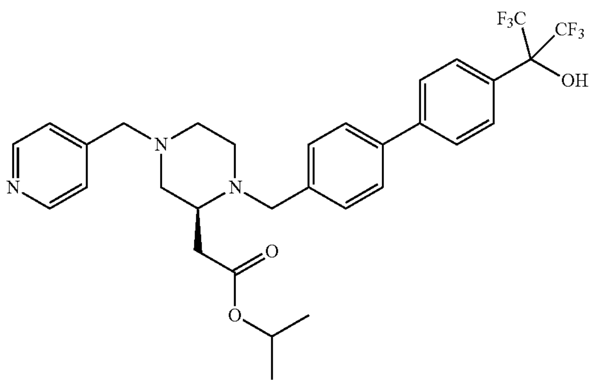 | isopropyl (S)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 185 |
| 82 | 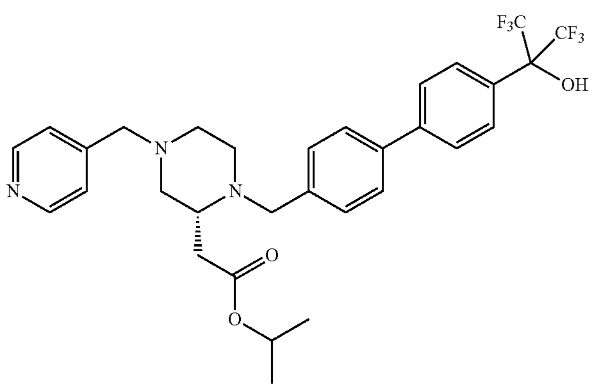 [SMILES: CC(C)OC(=O)CC1CN(Cc2ccncc2)CCN1Cc1ccc(-c2ccc(C(O)(C(F)(F)F)C(F)(F)F)cc2)cc1] | isopropyl (R)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 186 |
| 83 | 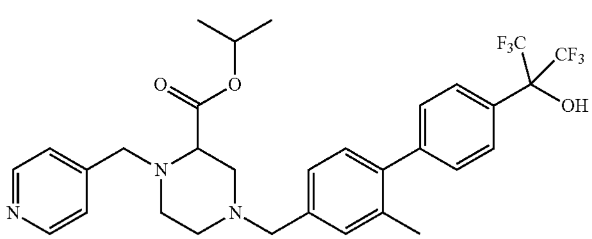 | isopropyl 4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 187 |

TABLE 1-continued

| Compound No. | Structure | Compound name | Synthetic Protocol/ Intermediates to be used |
|---|---|---|---|
| 84 | 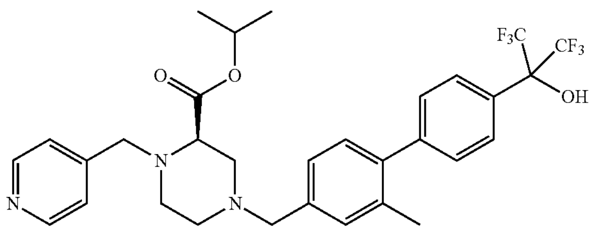 [SMILES: Cc1cc(CN2CCN(Cc3ccncc3)[C@@H](C(=O)OC(C)C)C2)ccc1-c1ccc(C(O)(C(F)(F)F)C(F)(F)F)cc1] | isopropyl (R)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 188 |
| 85 | 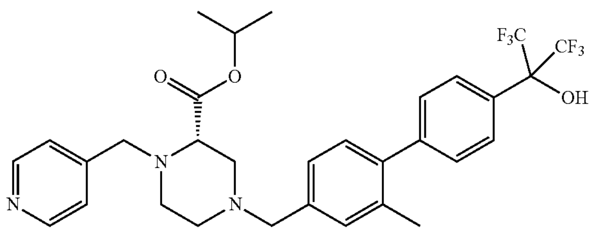 [SMILES: Cc1cc(CN2CCN(Cc3ccncc3)[C@H](C(=O)OC(C)C)C2)ccc1-c1ccc(C(O)(C(F)(F)F)C(F)(F)F)cc1] | isopropyl (S)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 189 |
| 86 | 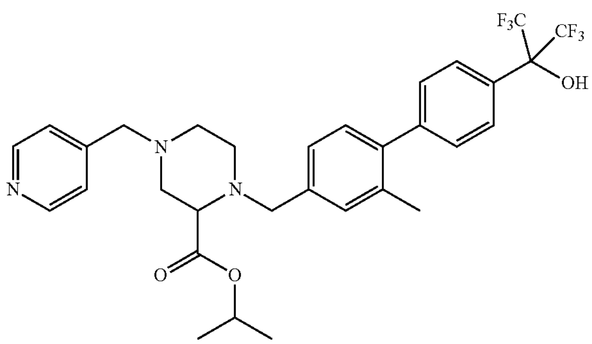 [SMILES: Cc1cc(CN2CCN(Cc3ccncc3)CC2C(=O)OC(C)C)ccc1-c1ccc(C(O)(C(F)(F)F)C(F)(F)F)cc1] | isopropyl 1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 190 |
| 87 | 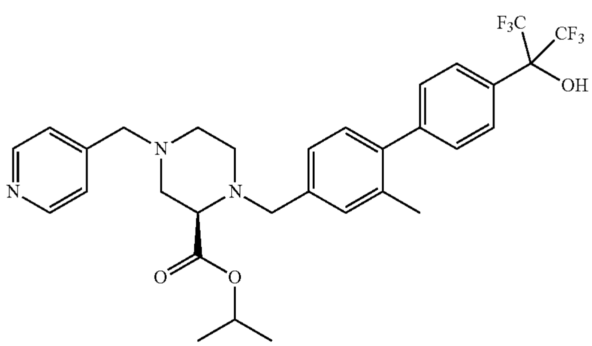 [SMILES: Cc1cc(CN2CCN(Cc3ccncc3)C[C@@H]2C(=O)OC(C)C)ccc1-c1ccc(C(O)(C(F)(F)F)C(F)(F)F)cc1] | isopropyl (R)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 191 |
| 88 | 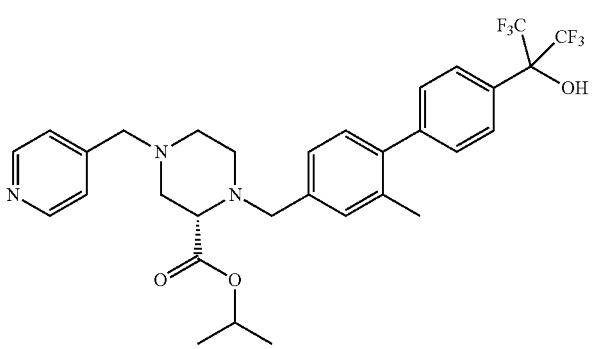 [SMILES: Cc1cc(CN2CCN(Cc3ccncc3)C[C@H]2C(=O)OC(C)C)ccc1-c1ccc(C(O)(C(F)(F)F)C(F)(F)F)cc1] | isopropyl (S)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 192 |

TABLE 1-continued

| Compound No. | Structure | Compound name | Synthetic Protocol/ Intermediates to be used |
|---|---|---|---|
| 89 | 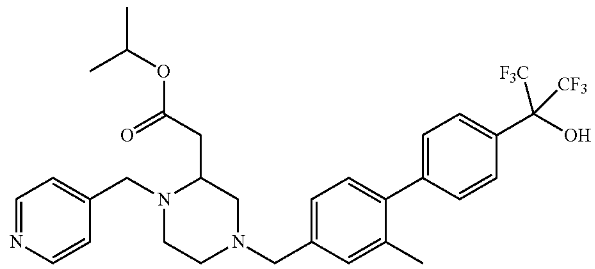 [SMILES: Cc1cc(CN2CCN(Cc3ccncc3)C(CC(=O)OC(C)C)C2)ccc1-c1ccc(C(O)(C(F)(F)F)C(F)(F)F)cc1] | isopropyl 2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 193 |
| 90 | 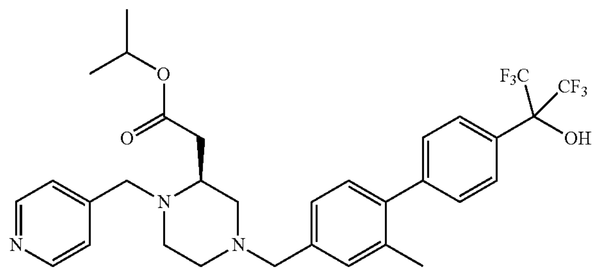 [SMILES: Cc1cc(CN2CCN(Cc3ccncc3)[C@@H](CC(=O)OC(C)C)C2)ccc1-c1ccc(C(O)(C(F)(F)F)C(F)(F)F)cc1] | isopropyl (S)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 50 |
| 91 | 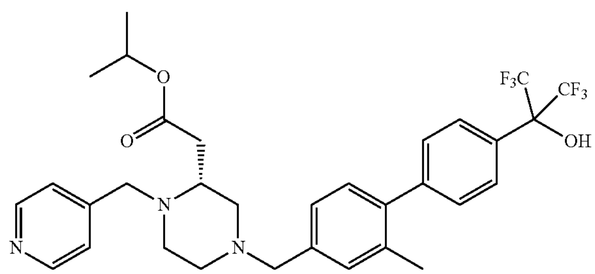 [SMILES: Cc1cc(CN2CCN(Cc3ccncc3)[C@H](CC(=O)OC(C)C)C2)ccc1-c1ccc(C(O)(C(F)(F)F)C(F)(F)F)cc1] | isopropyl (R)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 194 |
| 92 | 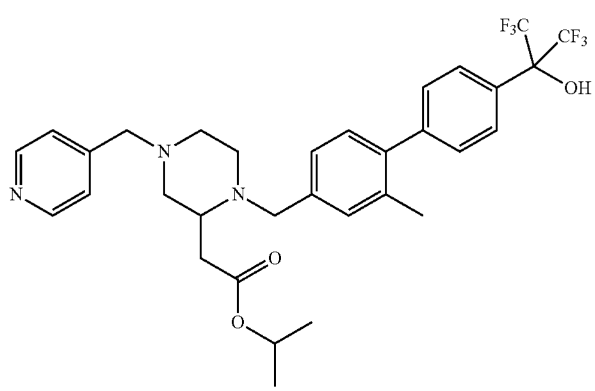 [SMILES: Cc1cc(CN2CCN(Cc3ccncc3)CC2CC(=O)OC(C)C)ccc1-c1ccc(C(O)(C(F)(F)F)C(F)(F)F)cc1] | isopropyl 2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 195 |

TABLE 1-continued

| Compound No. | Structure | Compound name | Synthetic Protocol/ Intermediates to be used |
|---|---|---|---|
| 93 | 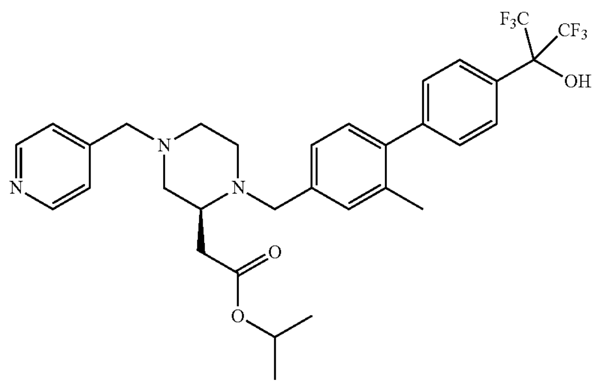 [SMILES: Cc1cc(CN2CCN(Cc3ccncc3)C[C@@H]2CC(=O)OC(C)C)ccc1-c1ccc(C(O)(C(F)(F)F)C(F)(F)F)cc1] | isopropyl (S)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 196 |
| 94 | 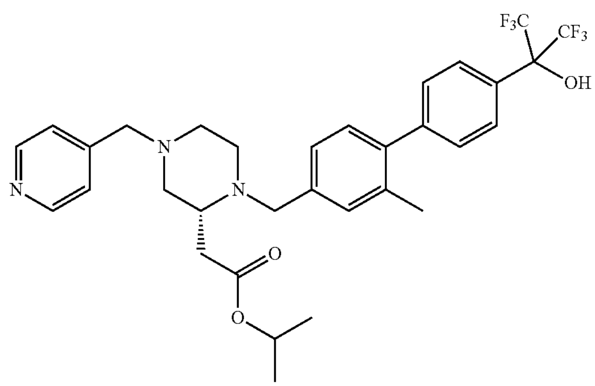 [SMILES: Cc1cc(CN2CCN(Cc3ccncc3)C[C@H]2CC(=O)OC(C)C)ccc1-c1ccc(C(O)(C(F)(F)F)C(F)(F)F)cc1] | isopropyl (R)-2-(1-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol E using 197 |
| 95 | 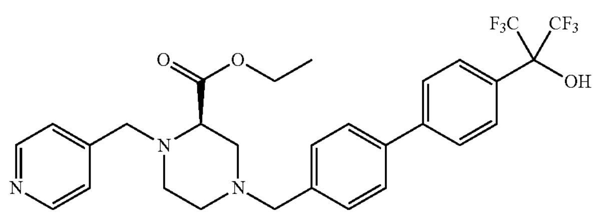 [SMILES: CCOC(=O)[C@H]1CN(Cc2ccc(-c3ccc(C(O)(C(F)(F)F)C(F)(F)F)cc3)cc2)CCN1Cc1ccncc1] | ethyl (R)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol C substituting 1-(tert-butyl) 3-ethyl (R)-piperazine-1,3-dicarboxylate for 36 |
| 96 | 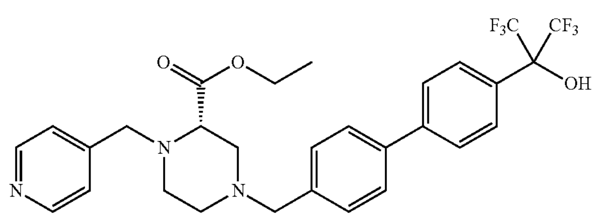 [SMILES: CCOC(=O)[C@@H]1CN(Cc2ccc(-c3ccc(C(O)(C(F)(F)F)C(F)(F)F)cc3)cc2)CCN1Cc1ccncc1] | ethyl (S)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol C substituting 1-(tert-butyl) 3-ethyl (S)-piperazine-1,3-dicarboxylate for 36 |
| 97 | 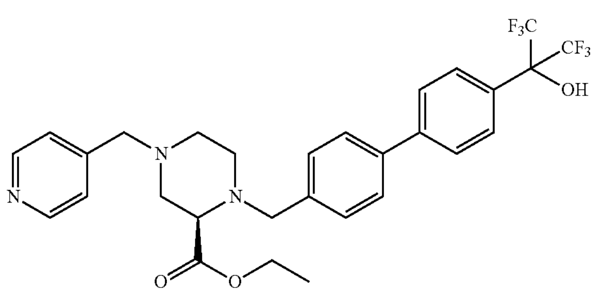 [SMILES: CCOC(=O)[C@H]1CN(Cc2ccncc2)CCN1Cc1ccc(-c2ccc(C(O)(C(F)(F)F)C(F)(F)F)cc2)cc1] | ethyl (R)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol A substituting 1-(tert-butyl) 3-ethyl (R)-piperazine-1,3-dicarboxylate for 5 |

TABLE 1-continued

| Compound No. | Structure | Compound name | Synthetic Protocol/ Intermediates to be used |
|---|---|---|---|
| 98 | 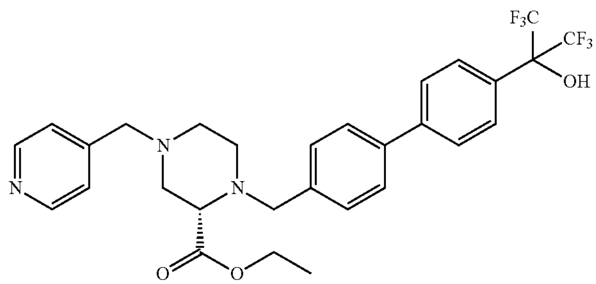 [SMILES: CCOC(=O)[C@@H]1CN(Cc2ccncc2)CCN1Cc1ccc(-c2ccc(C(O)(C(F)(F)F)C(F)(F)F)cc2)cc1] | ethyl (S)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol A substituting 1-(tert-butyl) 3-ethyl (S)-piperazine-1,3-dicarboxylate for 5 |
| 99 | 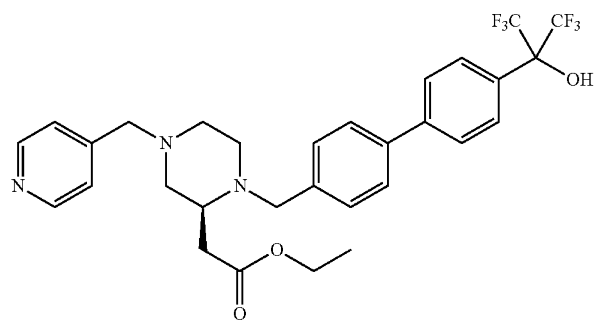 [SMILES: CCOC(=O)C[C@H]1CN(Cc2ccncc2)CCN1Cc1ccc(-c2ccc(C(O)(C(F)(F)F)C(F)(F)F)cc2)cc1] | ethyl (S)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol A substituting tert-butyl (S)-3-(2-ethoxy-2-oxoethyl)piperazine-1-carboxylate for 5 |
| 100 | 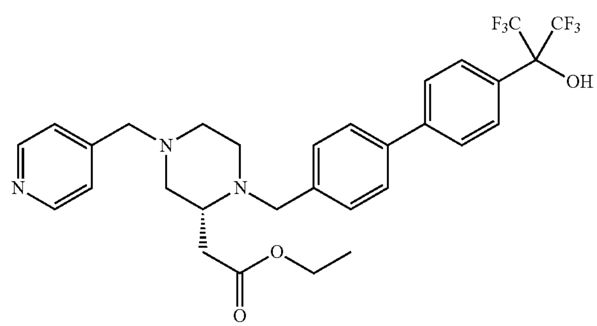 [SMILES: CCOC(=O)C[C@@H]1CN(Cc2ccncc2)CCN1Cc1ccc(-c2ccc(C(O)(C(F)(F)F)C(F)(F)F)cc2)cc1] | ethyl (R)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol A substituting tert-butyl (R)-3-(2-ethoxy-2-oxoethyl)piperazine-1-carboxylate for 5 |
| 101 | 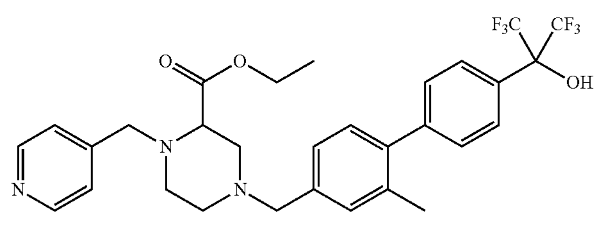 [SMILES: CCOC(=O)C1CN(Cc2ccc(-c3ccc(C(O)(C(F)(F)F)C(F)(F)F)cc3)c(C)c2)CCN1Cc1ccncc1] | ethyl 4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol C substituting aldehyde 34 for 4 and where 5 is 1-(tert-butyl) 3-ethyl piperazine-1,3-dicarboxylate |
| 102 | 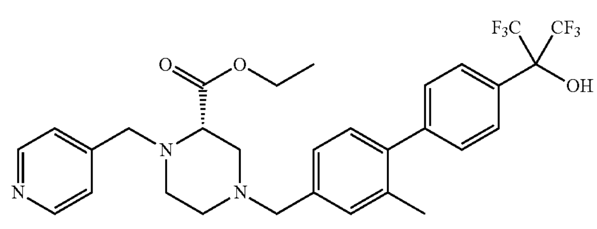 | ethyl (S)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol C substituting aldehyde 34 for 4 and where 5 is 1-(tert-butyl) 3-ethyl (S)-piperazine-1,3-dicarboxylate |

TABLE 1-continued

| Compound No. | Structure | Compound name | Synthetic Protocol/ Intermediates to be used |
|---|---|---|---|
| 103 | 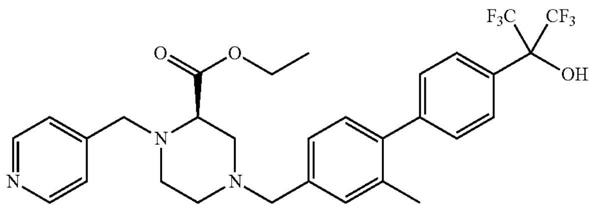 [SMILES: CCOC(=O)[C@H]1CN(Cc2ccc(-c3ccc(C(O)(C(F)(F)F)C(F)(F)F)cc3)c(C)c2)CCN1Cc1ccncc1] | ethyl (R)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol C substituting aldehyde 34 for 4 and where 5 is 1-(tert-butyl) 3-ethyl (R)-piperazine-1,3-dicarboxylate |
| 104 | 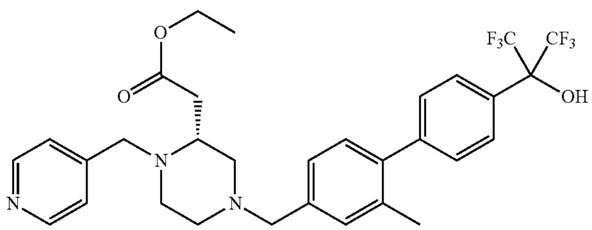 [SMILES: CCOC(=O)C[C@@H]1CN(Cc2ccc(-c3ccc(C(O)(C(F)(F)F)C(F)(F)F)cc3)c(C)c2)CCN1Cc1ccncc1] | ethyl (R)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol C substituting aldehyde 34 for 4 and where 5 is tert-butyl (R)-3-(2-ethoxy-2-oxoethyl)piperazine-1-carboxylate |
| 105 | 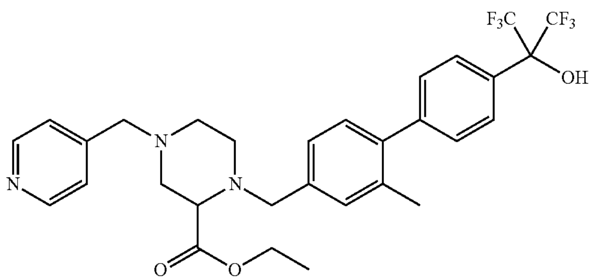 [SMILES: CCOC(=O)C1CN(Cc2ccncc2)CCN1Cc1ccc(-c2ccc(C(O)(C(F)(F)F)C(F)(F)F)cc2)c(C)c1] | ethyl 1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol A substituting aldehyde 34 for 4 and 5 is 1-(tert-butyl) 3-ethyl piperazine-1,3-dicarboxylate |
| 106 | 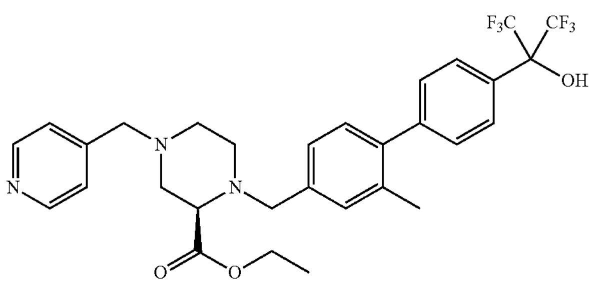 [SMILES: CCOC(=O)[C@H]1CN(Cc2ccncc2)CCN1Cc1ccc(-c2ccc(C(O)(C(F)(F)F)C(F)(F)F)cc2)c(C)c1] | ethyl (R)-1-((4'-(1,1,1,3,3,3-hexafluoro-2-hydroxypropan-2-yl)-2-methyl-[1,1'-biphenyl]-4-yl) methyl)-4-(pyridin-4-ylmethyl)piperazine-2-carboxylate | Protocol A substituting aldehyde 34 for 4 and 5 is 1-(tert-butyl) 3-ethyl (R)-piperazine-1,3-dicarboxylate |
| 107 | 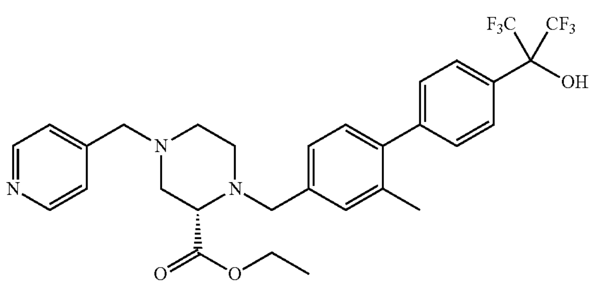 [SMILES: CCOC(=O)[C@@H]1CN(Cc2ccncc2)CCN1Cc1ccc(-c2ccc(C(O)(C(F)(F)F)C(F)(F)F)cc2)c(C)c1] | ethyl (S)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol A substituting aldehyde 34 for 4 and 5 is 1-(tert-butyl) 3-ethyl (S)-piperazine-1,3-dicarboxylate |

TABLE 1-continued

| Compound No. | Structure | Compound name | Synthetic Protocol/ Intermediates to be used |
|---|---|---|---|
| 108 | 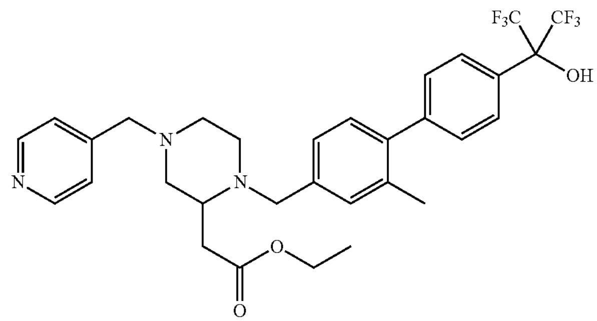 [SMILES: CCOC(=O)C[C@@H]1CN(Cc2ccncc2)CCN1Cc1ccc(-c2ccc(C(O)(C(F)(F)F)C(F)(F)F)cc2)c(C)c1] | ethyl 2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol A substituting aldehyde 34 for 4 and 5 is tert-butyl 3-(2-ethoxy-2-oxoethyl) piperazine-1-carboxylate |
| 109 | 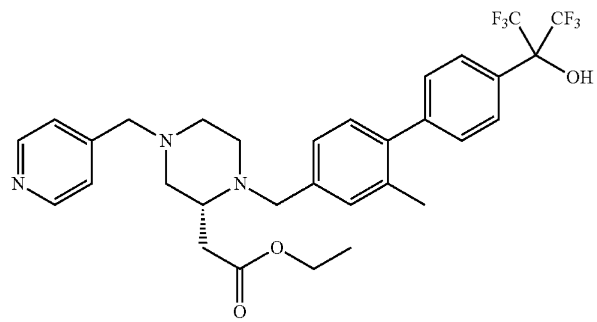 | ethyl (R)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol A substituting aldehyde 34 for 4 and 5 is tert-butyl (R)-3-(2-ethoxy-2-oxoethyl) piperazine-1-carboxylate |
| 110 | 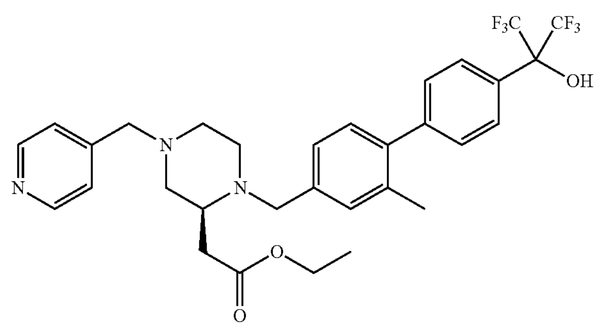 [SMILES: CCOC(=O)C[C@H]1CN(Cc2ccncc2)CCN1Cc1ccc(-c2ccc(C(O)(C(F)(F)F)C(F)(F)F)cc2)c(C)c1] | ethyl (S)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol A substituting aldehyde 34 for 4 and 5 is tert-butyl (S)-3-(2-ethoxy-2-oxoethyl) piperazine-1-carboxylate |
| 111 | 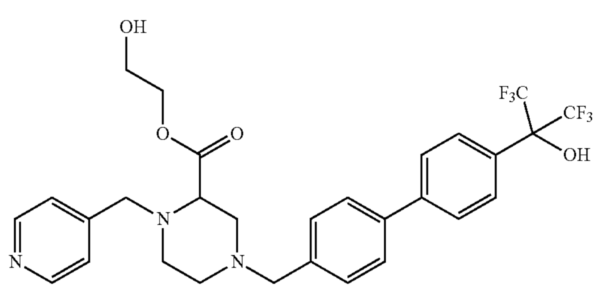 [SMILES: O=C(OCCO)C1CN(Cc2ccc(-c3ccc(C(O)(C(F)(F)F)C(F)(F)F)cc3)cc2)CCN1Cc1ccncc1] | 2-hydroxyethyl 4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 20 |
| 112 | 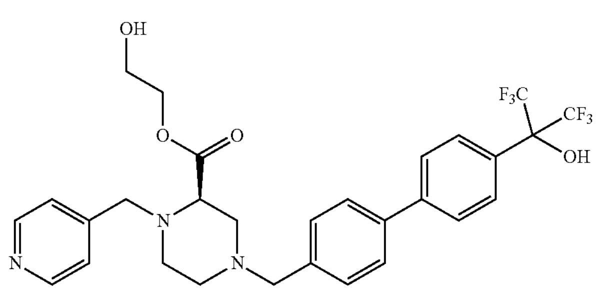 [SMILES: O=C(OCCO)[C@H]1CN(Cc2ccc(-c3ccc(C(O)(C(F)(F)F)C(F)(F)F)cc3)cc2)CCN1Cc1ccncc1] | 2-hydroxyethyl (R)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 179 |

TABLE 1-continued

| Compound No. | Structure | Compound name | Synthetic Protocol/ Intermediates to be used |
|---|---|---|---|
| 113 | 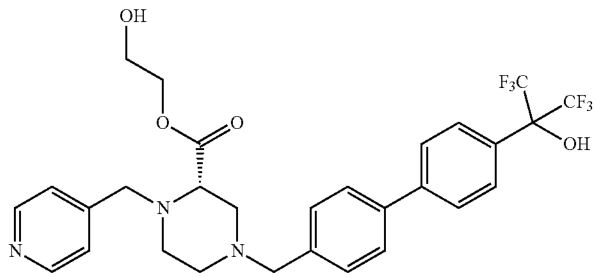 [SMILES: O=C(OCCO)[C@@H]1CN(Cc2ccc(-c3ccc(C(O)(C(F)(F)F)C(F)(F)F)cc3)cc2)CCN1Cc1ccncc1] | 2-hydroxyethyl (S)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 180 |
| 114 | 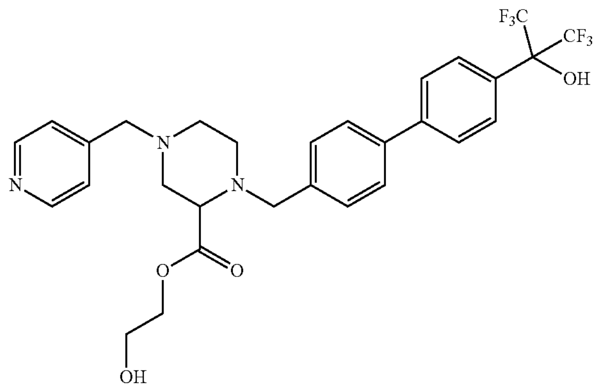 [SMILES: O=C(OCCO)C1CN(Cc2ccncc2)CCN1Cc1ccc(-c2ccc(C(O)(C(F)(F)F)C(F)(F)F)cc2)cc1] | 2-hydroxyethyl 1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 12 |
| 115 | 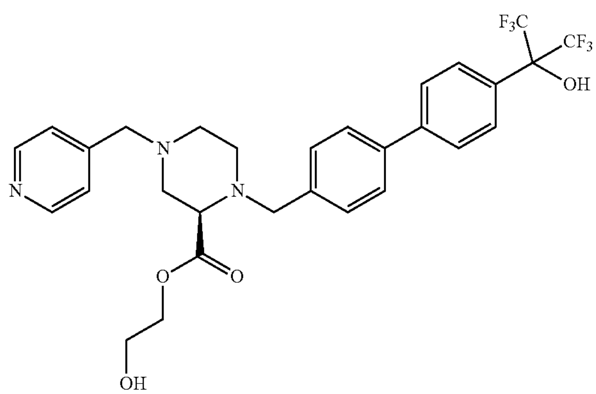 [SMILES: O=C(OCCO)[C@H]1CN(Cc2ccncc2)CCN1Cc1ccc(-c2ccc(C(O)(C(F)(F)F)C(F)(F)F)cc2)cc1] | 2-hydroxyethyl (R)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 181 |
| 116 | 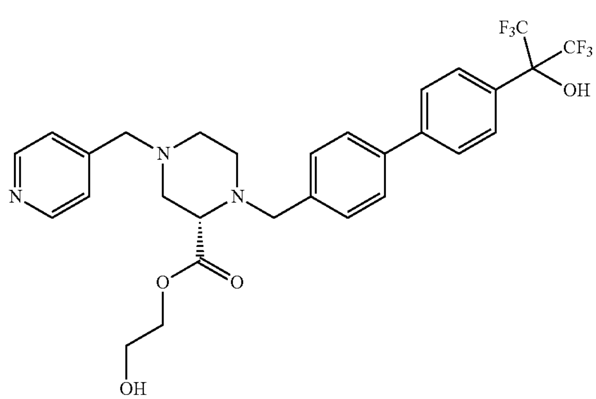 [SMILES: O=C(OCCO)[C@@H]1CN(Cc2ccncc2)CCN1Cc1ccc(-c2ccc(C(O)(C(F)(F)F)C(F)(F)F)cc2)cc1] | 2-hydroxyethyl (S)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 182 |

TABLE 1-continued

| Compound No. | Structure | Compound name | Synthetic Protocol/ Intermediates to be used |
|---|---|---|---|
| 117 | 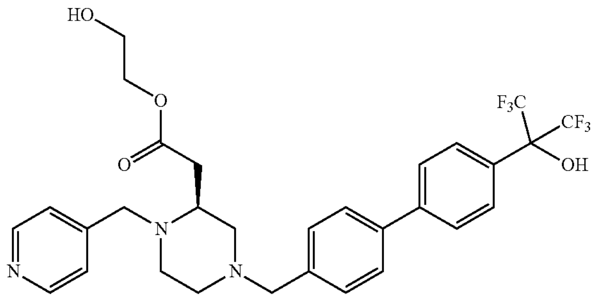 [SMILES: O=C(C[C@H]1CN(Cc2ccc(-c3ccc(C(O)(C(F)(F)F)C(F)(F)F)cc3)cc2)CCN1Cc1ccncc1)OCCO] | 2-hydroxyethyl (S)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate | Protocol F using 183 |
| 118 | 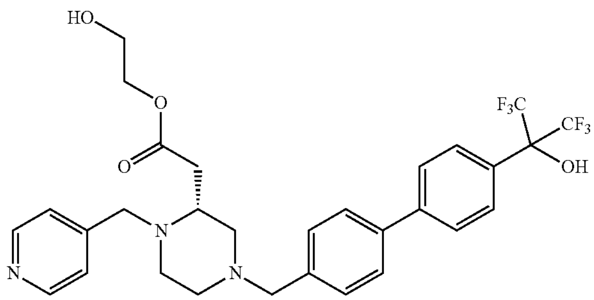 [SMILES: O=C(C[C@@H]1CN(Cc2ccc(-c3ccc(C(O)(C(F)(F)F)C(F)(F)F)cc3)cc2)CCN1Cc1ccncc1)OCCO] | 2-hydroxyethyl (R)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate | Protocol F using 184 |
| 119 | 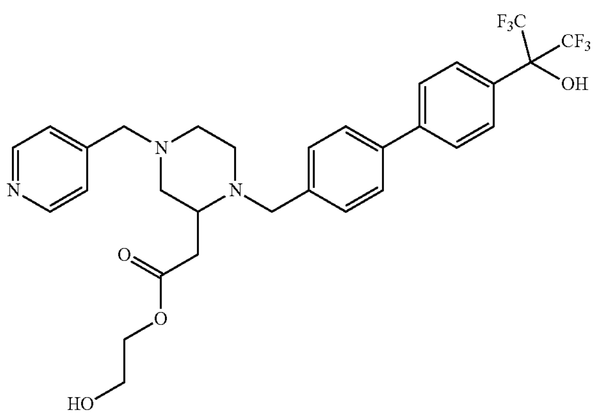 [SMILES: O=C(CC1CN(Cc2ccncc2)CCN1Cc1ccc(-c2ccc(C(O)(C(F)(F)F)C(F)(F)F)cc2)cc1)OCCO] | 2-hydroxyethyl 2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 13 |
| 120 | 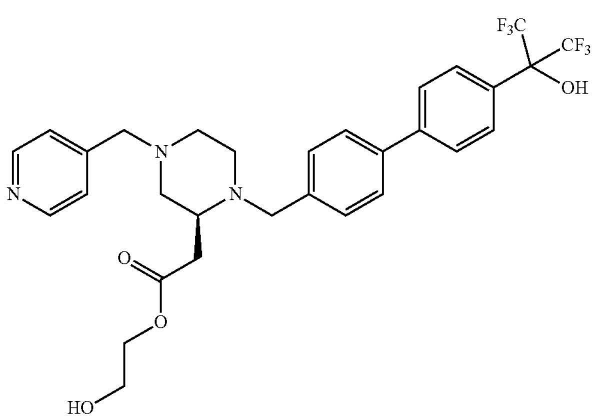 [SMILES: O=C(C[C@H]1CN(Cc2ccncc2)CCN1Cc1ccc(-c2ccc(C(O)(C(F)(F)F)C(F)(F)F)cc2)cc1)OCCO] | 2-hydroxyethyl (S)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 185 |

TABLE 1-continued

| Compound No. | Structure | Compound name | Synthetic Protocol/ Intermediates to be used |
|---|---|---|---|
| 121 | 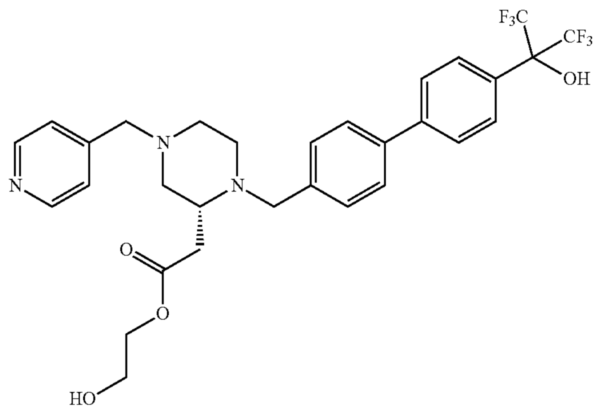 [SMILES: O=C(C[C@@H]1CN(Cc2ccncc2)CCN1Cc1ccc(-c2ccc(C(O)(C(F)(F)F)C(F)(F)F)cc2)cc1)OCCO] | 2-hydroxyethyl (R)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 186 |
| 122 | 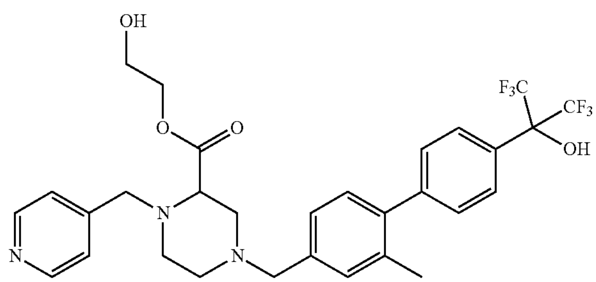 [SMILES: Cc1cc(CN2CCN(Cc3ccncc3)C(C(=O)OCCO)C2)ccc1-c1ccc(C(O)(C(F)(F)F)C(F)(F)F)cc1] | 2-hydroxyethyl 4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 187 |
| 123 | 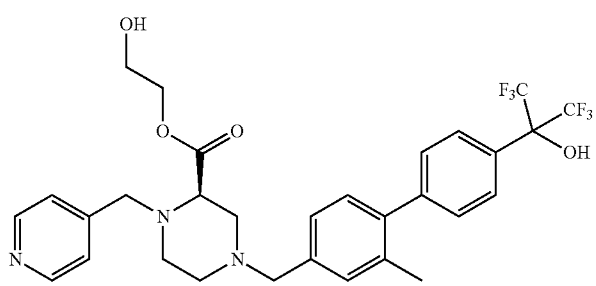 [SMILES: Cc1cc(CN2CCN(Cc3ccncc3)[C@@H](C(=O)OCCO)C2)ccc1-c1ccc(C(O)(C(F)(F)F)C(F)(F)F)cc1] | 2-hydroxyethyl (R)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 188 |
| 124 | 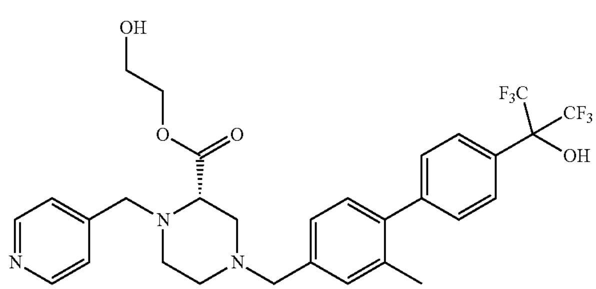 | 2-hydroxyethyl (S)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 189 |

TABLE 1-continued

| Compound No. | Structure | Compound name | Synthetic Protocol/ Intermediates to be used |
|---|---|---|---|
| 125 | 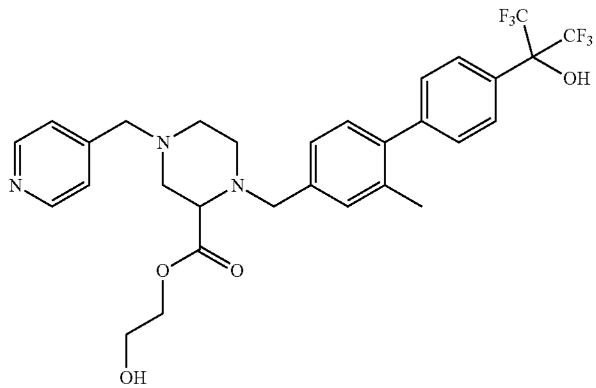 [SMILES: Cc1cc(CN2CCN(Cc3ccncc3)CC2C(=O)OCCO)ccc1-c1ccc(C(O)(C(F)(F)F)C(F)(F)F)cc1] | 2-hydroxyethyl 1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 190 |
| 126 | 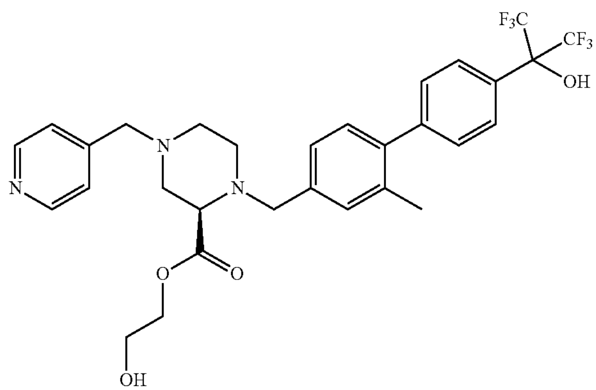 [SMILES: Cc1cc(CN2CCN(Cc3ccncc3)C[C@@H]2C(=O)OCCO)ccc1-c1ccc(C(O)(C(F)(F)F)C(F)(F)F)cc1] | 2-hydroxyethyl (R)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 191 |
| 127 | 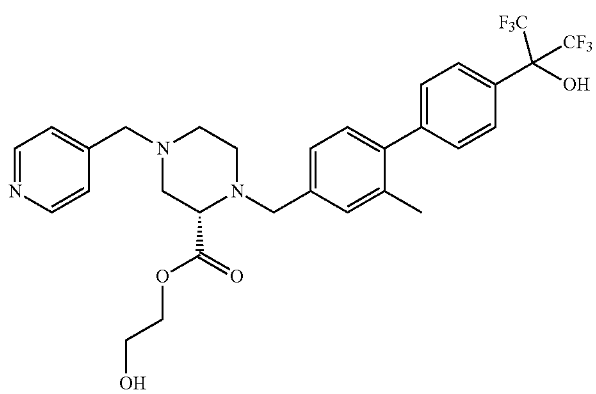 [SMILES: Cc1cc(CN2CCN(Cc3ccncc3)C[C@H]2C(=O)OCCO)ccc1-c1ccc(C(O)(C(F)(F)F)C(F)(F)F)cc1] | 2-hydroxyethyl (S)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 192 |
| 128 | 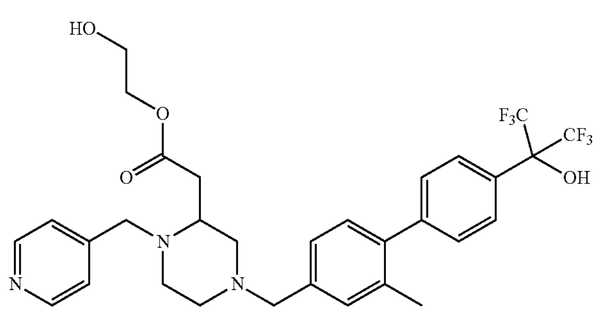 [SMILES: Cc1cc(CN2CCN(Cc3ccncc3)C(CC(=O)OCCO)C2)ccc1-c1ccc(C(O)(C(F)(F)F)C(F)(F)F)cc1] | 2-hydroxyethyl 2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 193 |

TABLE 1-continued

| Compound No. | Structure | Compound name | Synthetic Protocol/ Intermediates to be used |
|---|---|---|---|
| 129 | 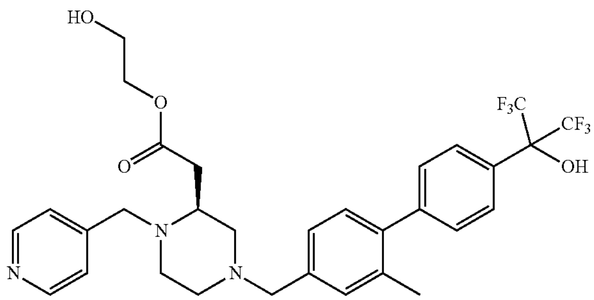 [SMILES: Cc1cc(CN2CCN(Cc3ccncc3)[C@@H](CC(=O)OCCO)C2)ccc1-c1ccc(C(O)(C(F)(F)F)C(F)(F)F)cc1] | 2-hydroxyethyl (S)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 50 |
| 130 | 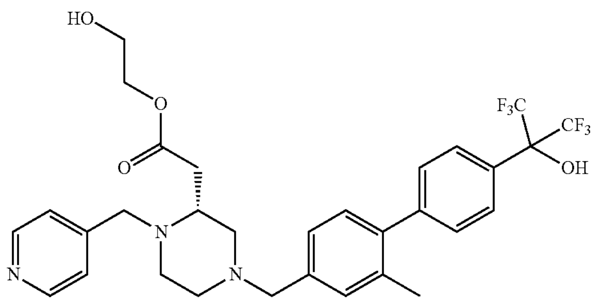 [SMILES: Cc1cc(CN2CCN(Cc3ccncc3)[C@H](CC(=O)OCCO)C2)ccc1-c1ccc(C(O)(C(F)(F)F)C(F)(F)F)cc1] | 2-hydroxyethyl (R)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 194 |
| 131 | 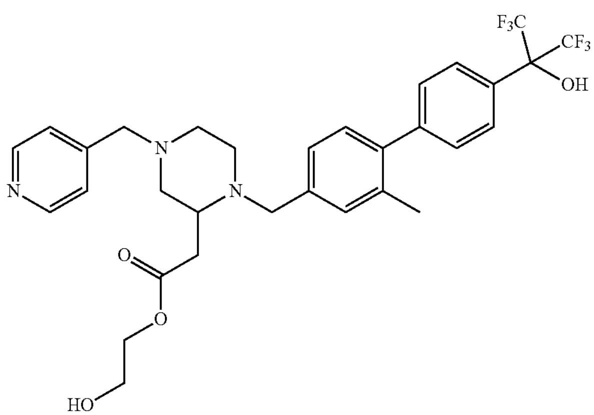 | 2-hydroxyethyl 2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 195 |
| 132 | 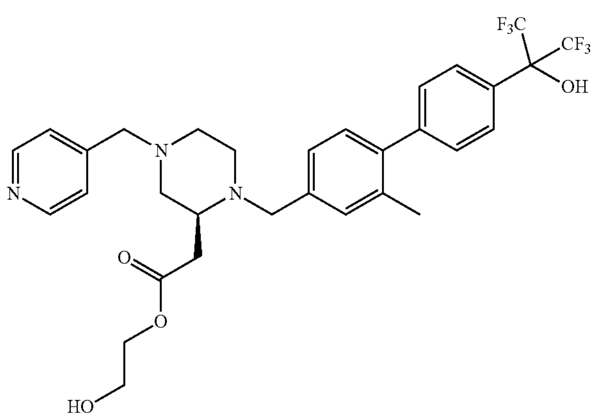 [SMILES: Cc1cc(CN2CCN(Cc3ccncc3)C[C@@H]2CC(=O)OCCO)ccc1-c1ccc(C(O)(C(F)(F)F)C(F)(F)F)cc1] | 2-hydroxyethyl (S)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 196 |

TABLE 1-continued

| Compound No. | Structure | Compound name | Synthetic Protocol/ Intermediates to be used |
| --- | --- | --- | --- |
| 133 | 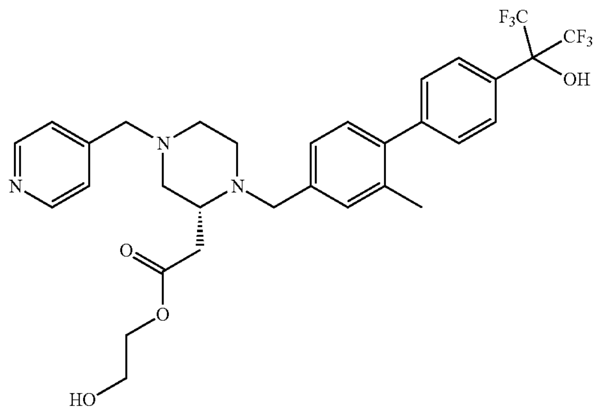 [SMILES: Cc1cc(CN2CCN(Cc3ccncc3)C[C@H]2CC(=O)OCCO)ccc1-c1ccc(C(O)(C(F)(F)F)C(F)(F)F)cc1] | 2-hydroxyethyl (R)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 197 |
| 134 | 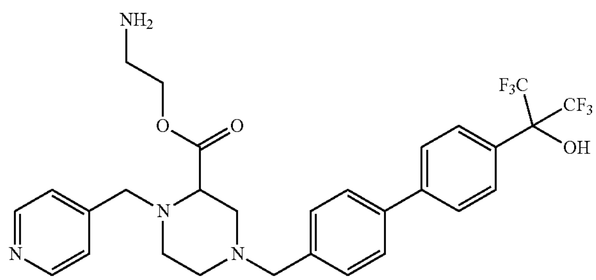 | 2-aminoethyl 4-((4'-(1,1,1,3,3,3-hexafluoro-2-hydroxypropan-2-yl)-[1,1'-biphenyl]-1,4-yl)methyl)-1-(pyridin-4-ylmethyl)piperazine-2-carboxylate | Synthetic method described in Example 17 using 20 as starting material |
| 135 | 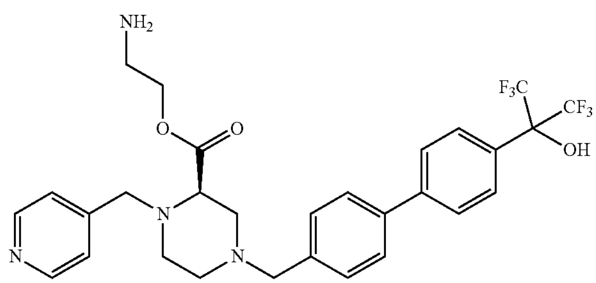 [SMILES: NCCOC(=O)[C@H]1CN(Cc2ccc(-c3ccc(C(O)(C(F)(F)F)C(F)(F)F)cc3)cc2)CCN1Cc1ccncc1] | 2-aminoethyl (R)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Synthetic method described in Example 17 using 179 as starting material |
| 136 | 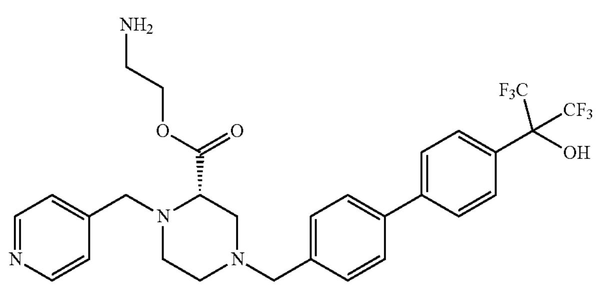 | 2-aminoethyl (S)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Synthetic method described in Example 17 using 180 as starting material |

TABLE 1-continued

| Compound No. | Structure | Compound name | Synthetic Protocol/ Intermediates to be used |
|---|---|---|---|
| 137 | 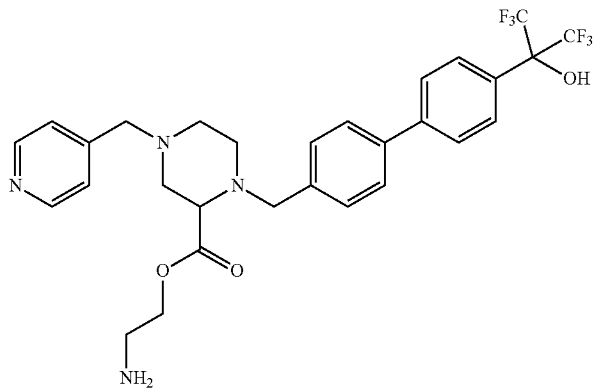 [SMILES: NCCOC(=O)C1CN(Cc2ccncc2)CCN1Cc1ccc(-c2ccc(C(O)(C(F)(F)F)C(F)(F)F)cc2)cc1] | 2-aminoethyl 1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 12 as starting material, followed by Step B of Example 17 |
| 138 | 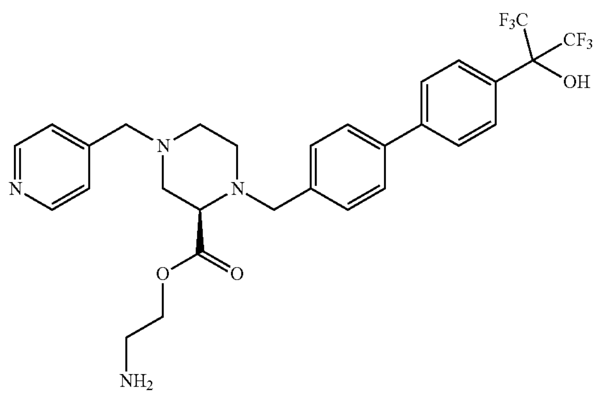 [SMILES: NCCOC(=O)[C@H]1CN(Cc2ccncc2)CCN1Cc1ccc(-c2ccc(C(O)(C(F)(F)F)C(F)(F)F)cc2)cc1] | 2-aminoethyl (R)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 181 as starting material, followed by Step B of Example 17 |
| 139 | 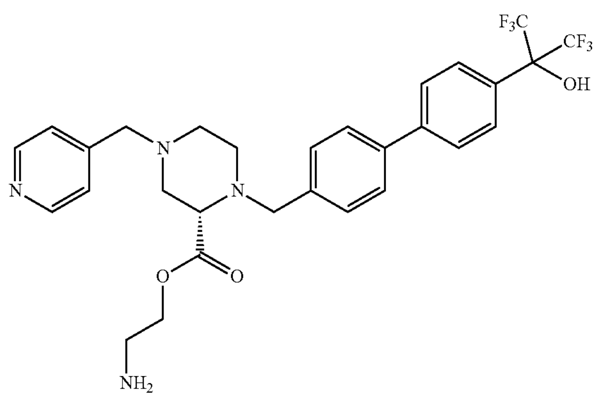 | 2-aminoethyl (S)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 182 as starting material, followed by Step B of Example 17 |
| 140 | 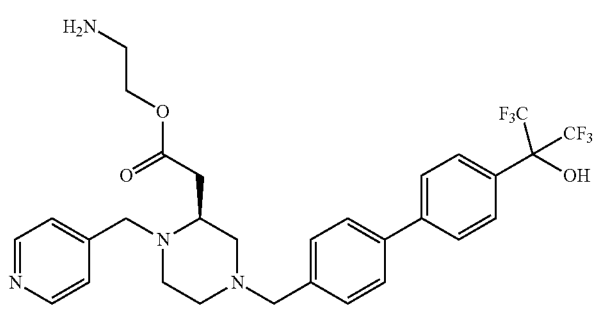 [SMILES: NCCOC(=O)C[C@H]1CN(Cc2ccc(-c3ccc(C(O)(C(F)(F)F)C(F)(F)F)cc3)cc2)CCN1Cc1ccncc1] | 2-aminoethyl (S)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate | Synthetic method described in Example 17 using 183 as starting material |

TABLE 1-continued

| Compound No. | Structure | Compound name | Synthetic Protocol/ Intermediates to be used |
|---|---|---|---|
| 141 | 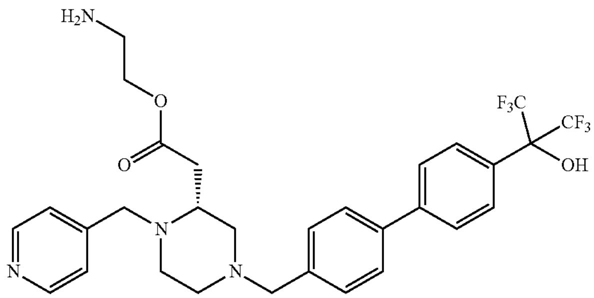 [SMILES: NCCOC(=O)C[C@@H]1CN(Cc2ccc(-c3ccc(C(O)(C(F)(F)F)C(F)(F)F)cc3)cc2)CCN1Cc1ccncc1] | 2-aminoethyl (R)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate | Synthetic method described in Example 17 using 184 as starting material |
| 142 | 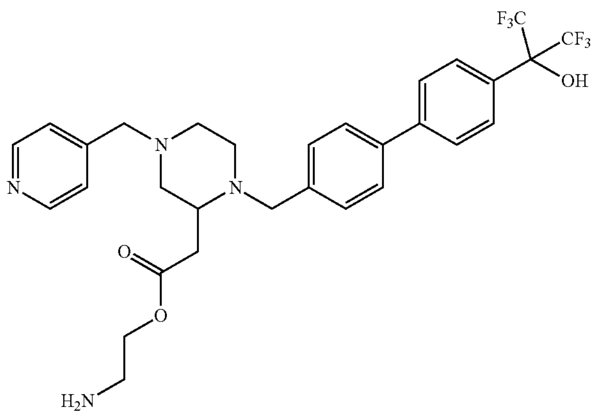 [SMILES: NCCOC(=O)CC1CN(Cc2ccncc2)CCN1Cc1ccc(-c2ccc(C(O)(C(F)(F)F)C(F)(F)F)cc2)cc1] | 2-aminoethyl 2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 13 followed by Step B of Example 17 |
| 143 | 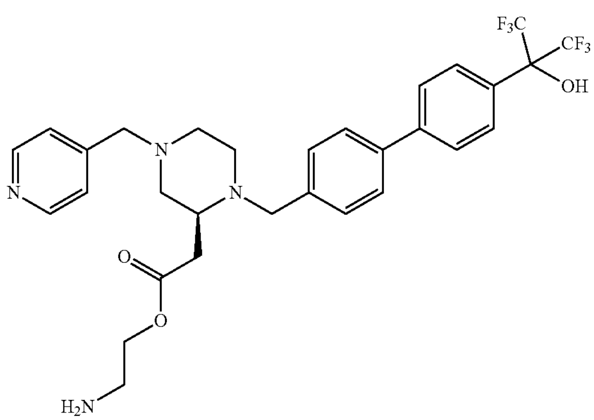 [SMILES: NCCOC(=O)C[C@H]1CN(Cc2ccncc2)CCN1Cc1ccc(-c2ccc(C(O)(C(F)(F)F)C(F)(F)F)cc2)cc1] | 2-aminoethyl (S)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 185 followed by Step B of Example 17 |
| 144 | 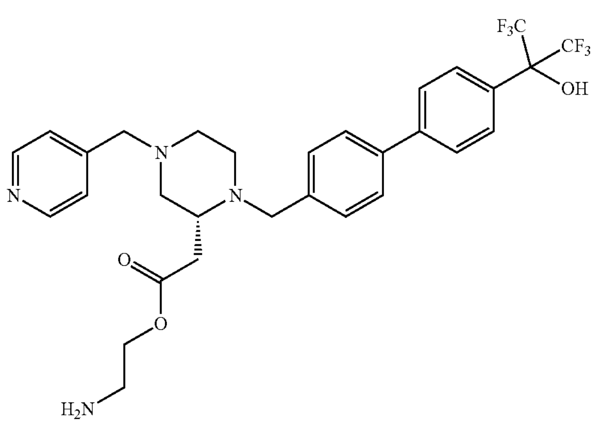 | 2-aminoethyl (R)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 186 followed by Step B of Example 17 |

TABLE 1-continued

| Compound No. | Structure | Compound name | Synthetic Protocol/ Intermediates to be used |
|---|---|---|---|
| 145 | 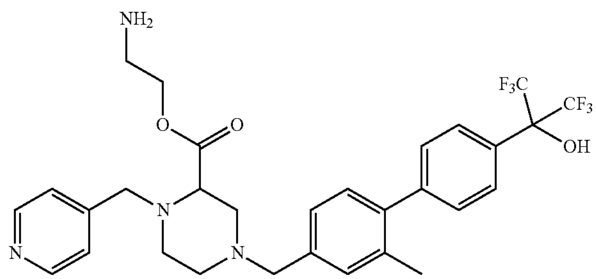 | 2-aminoethyl 4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Synthetic method described in Example 17 using 187 as starting material |
| 146 | 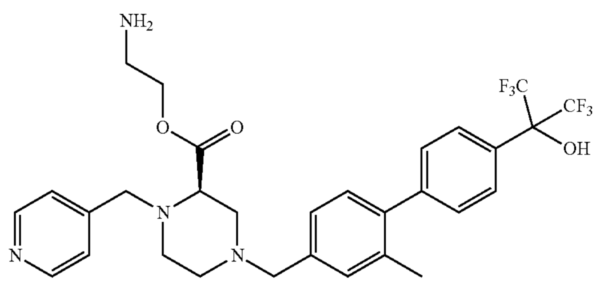 | 2-aminoethyl (R)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Synthetic method described in Example 17 using 188 as starting material |
| 147 | 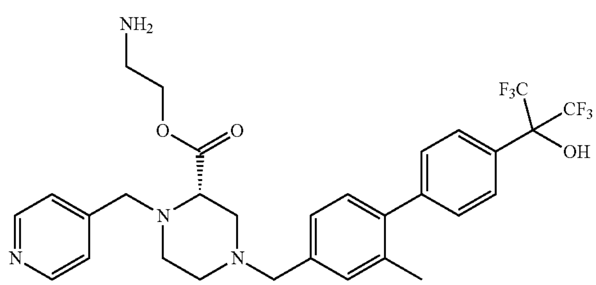 | 2-aminoethyl (S)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Synthetic method described in Example 17 using 189 as starting material |
| 148 | 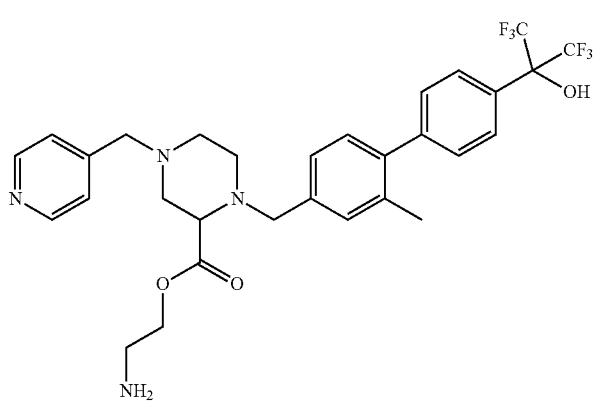 | 2-aminoethyl 1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Synthetic method described in Example 17 using 190 as starting material |

TABLE 1-continued

| Compound No. | Structure | Compound name | Synthetic Protocol/ Intermediates to be used |
|---|---|---|---|
| 149 | 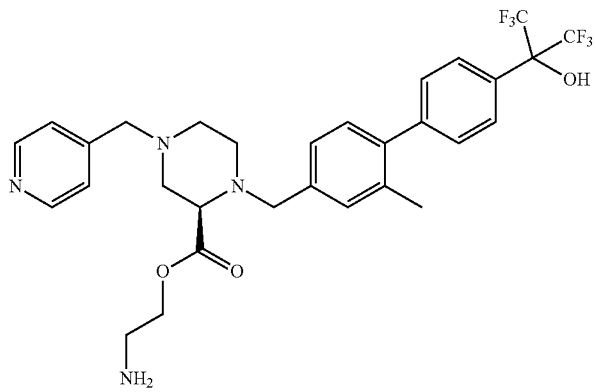 | 2-aminoethyl (R)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 191 followed by Step B of Example 17 |
| 150 | 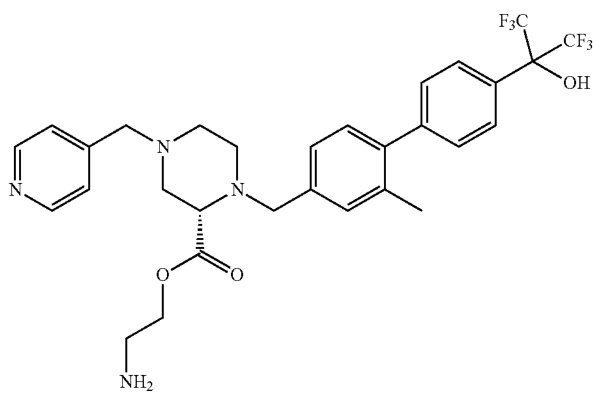 [SMILES: Cc1cc(CN2CCN(Cc3ccncc3)CC2C(=O)OCCN)ccc1-c1ccc(C(O)(C(F)(F)F)C(F)(F)F)cc1] | 2-aminoethyl (S)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 192 followed by Step B of Example 17 |
| 151 | 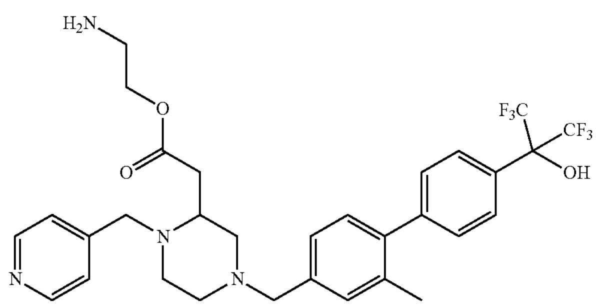 [SMILES: Cc1cc(CN2CCN(Cc3ccncc3)C(CC(=O)OCCN)C2)ccc1-c1ccc(C(O)(C(F)(F)F)C(F)(F)F)cc1] | 2-aminoethyl 2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Synthetic method described in Example 17 using 193 as starting material |
| 152 | 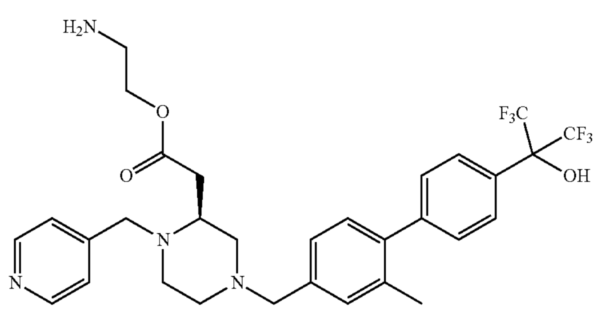 | 2-aminoethyl (S)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Synthetic method described in Example 17 using using 50 as starting material |

TABLE 1-continued

| Compound No. | Structure | Compound name | Synthetic Protocol/ Intermediates to be used |
|---|---|---|---|
| 153 | 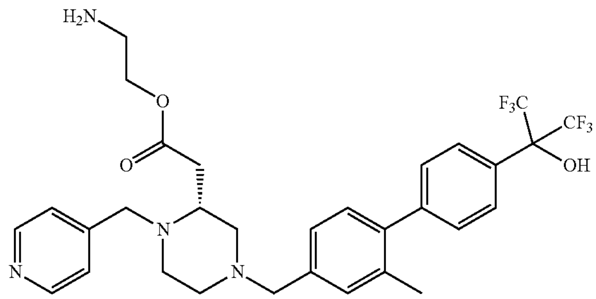 [SMILES: Cc1cc(CN2CCN(Cc3ccncc3)[C@H](CC(=O)OCCN)C2)ccc1-c1ccc(C(O)(C(F)(F)F)C(F)(F)F)cc1] | 2-aminoethyl (R)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Synthetic method described in Example 17 using 194 as starting material |
| 154 | 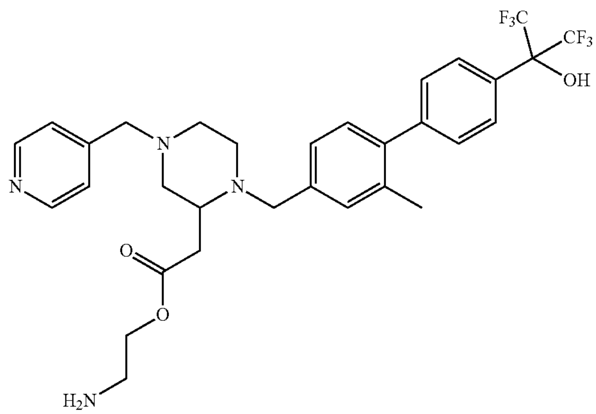 [SMILES: Cc1cc(CN2CCN(Cc3ccncc3)CC2CC(=O)OCCN)ccc1-c1ccc(C(O)(C(F)(F)F)C(F)(F)F)cc1] | 2-aminoethyl 2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 195 followed by Step B of Example 17 |
| 155 | 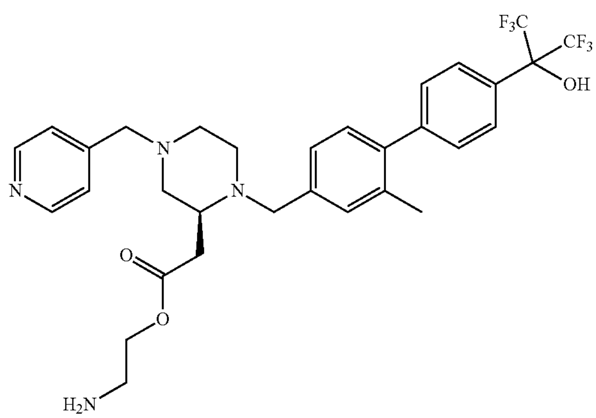 [SMILES: Cc1cc(CN2CCN(Cc3ccncc3)C[C@@H]2CC(=O)OCCN)ccc1-c1ccc(C(O)(C(F)(F)F)C(F)(F)F)cc1] | 2-aminoethyl (S)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 196 followed by Step B of Example 17 |
| 156 | 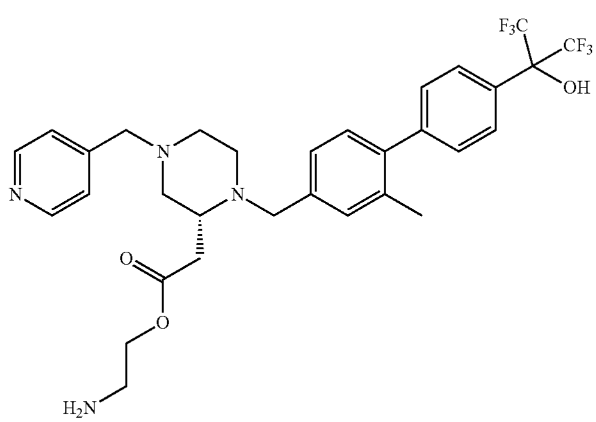 | 2-aminoethyl (R)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 197 followed by Step B of Example 17 |

TABLE 1-continued

| Compound No. | Structure | Compound name | Synthetic Protocol/ Intermediates to be used |
|---|---|---|---|
| 157 | 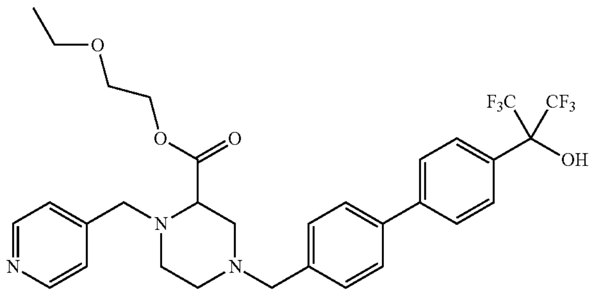 | 2-ethoxyethyl 4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 20 |
| 158 | 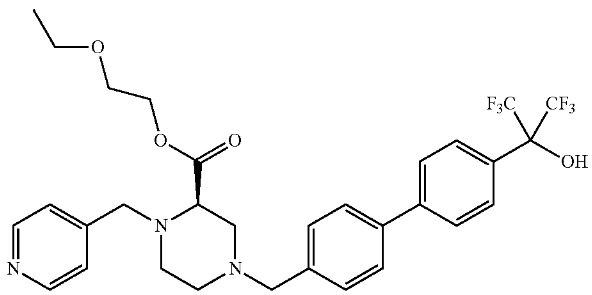 [SMILES: CCOCCOC(=O)[C@H]1CN(Cc2ccc(-c3ccc(C(O)(C(F)(F)F)C(F)(F)F)cc3)cc2)CCN1Cc1ccncc1] | 2-ethoxyethyl (R)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 179 |
| 159 | 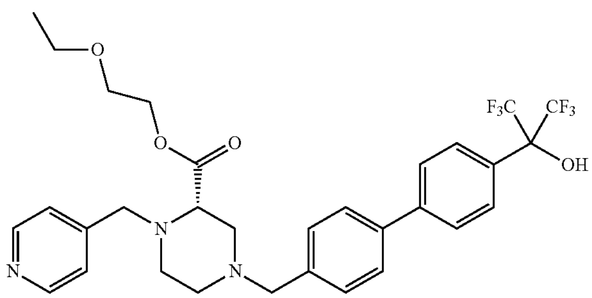 [SMILES: CCOCCOC(=O)[C@@H]1CN(Cc2ccc(-c3ccc(C(O)(C(F)(F)F)C(F)(F)F)cc3)cc2)CCN1Cc1ccncc1] | 2-ethoxyethyl (S)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylate | Protocol F using 180 |
| 160 | 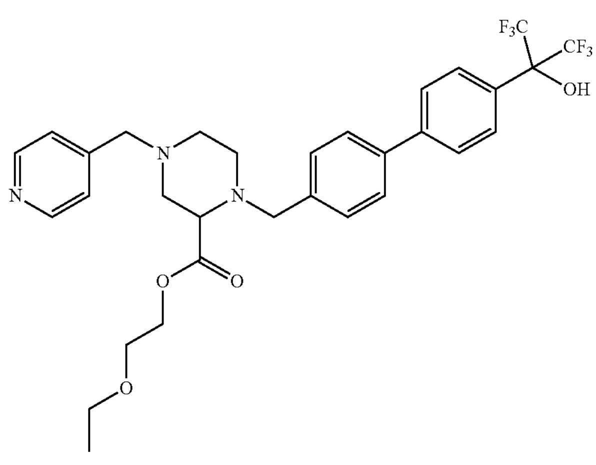 [SMILES: CCOCCOC(=O)C1CN(Cc2ccncc2)CCN1Cc1ccc(-c2ccc(C(O)(C(F)(F)F)C(F)(F)F)cc2)cc1] | 2-ethoxyethyl 1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 12 |

TABLE 1-continued

| Compound No. | Structure | Compound name | Synthetic Protocol/ Intermediates to be used |
|---|---|---|---|
| 161 | 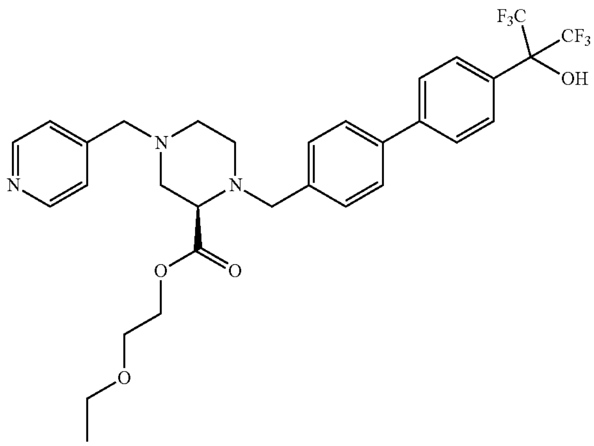 [SMILES: CCOCCOC(=O)[C@H]1CN(Cc2ccncc2)CCN1Cc1ccc(-c2ccc(C(O)(C(F)(F)F)C(F)(F)F)cc2)cc1] | 2-ethoxyethyl (R)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 181 |
| 162 | 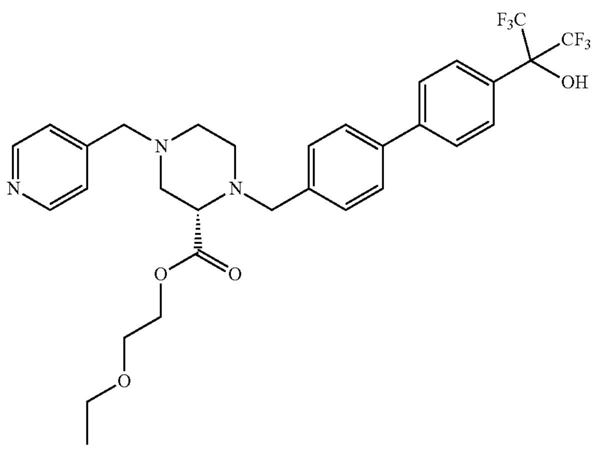 | 2-ethoxyethyl (S)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylate | Protocol E using 182 |
| 163 | 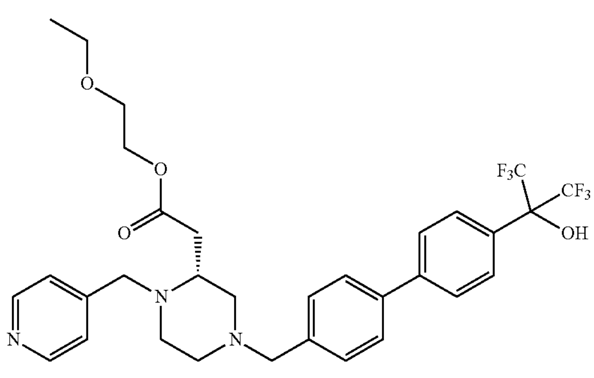 [SMILES: CCOCCOC(=O)C[C@@H]1CN(Cc2ccc(-c3ccc(C(O)(C(F)(F)F)C(F)(F)F)cc3)cc2)CCN1Cc1ccncc1] | 2-ethoxyethyl (R)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetate | Protocol F using 184 |

TABLE 1-continued

| Compound No. | Structure | Compound name | Synthetic Protocol/ Intermediates to be used |
|---|---|---|---|
| 164 | 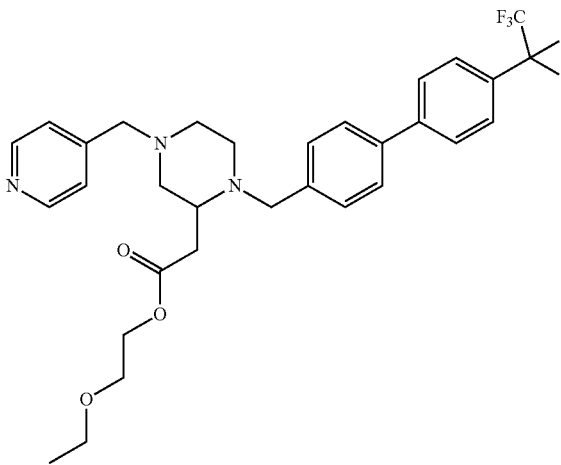 | 2-ethoxyethyl 2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 13 |
| 165 | 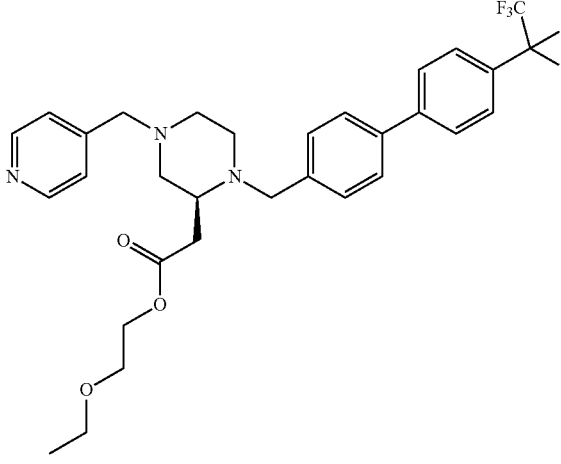 | 2-ethoxyethyl (S)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 185 |
| 166 | 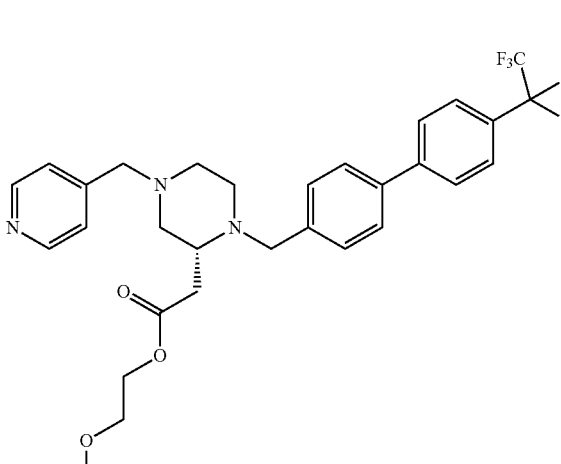 | 2-ethoxyethyl (R)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetate | Protocol E using 186 |

TABLE 1-continued

| Compound No. | Structure | Compound name | Synthetic Protocol/ Intermediates to be used |
| --- | --- | --- | --- |
| 167 | 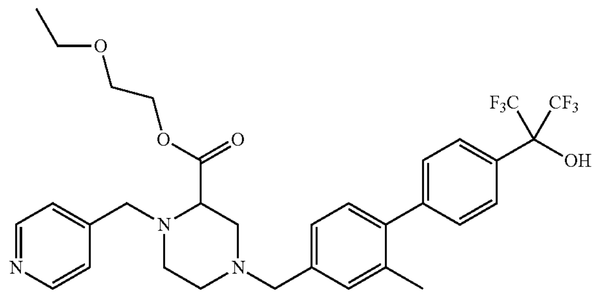 [SMILES: CCOCCOC(=O)C1CN(Cc2ccc(-c3ccc(C(O)(C(F)(F)F)C(F)(F)F)cc3)c(C)c2)CCN1Cc1ccncc1] | 2-ethoxyethyl 4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 187 |
| 168 | 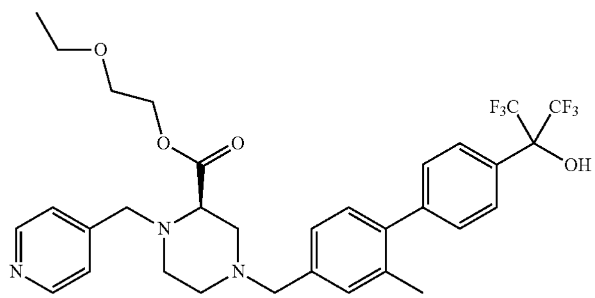 [SMILES: CCOCCOC(=O)[C@H]1CN(Cc2ccc(-c3ccc(C(O)(C(F)(F)F)C(F)(F)F)cc3)c(C)c2)CCN1Cc1ccncc1] | 2-ethoxyethyl (R)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 188 |
| 169 | 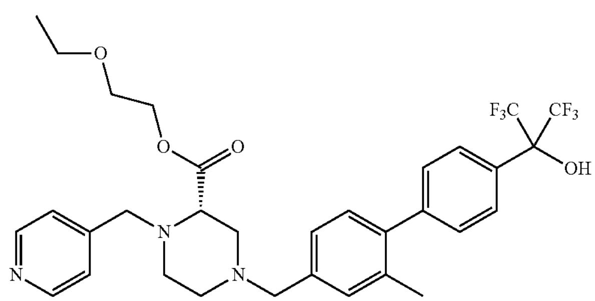 [SMILES: CCOCCOC(=O)[C@@H]1CN(Cc2ccc(-c3ccc(C(O)(C(F)(F)F)C(F)(F)F)cc3)c(C)c2)CCN1Cc1ccncc1] | 2-ethoxyethyl (S)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylate | Protocol F using 189 |
| 170 | 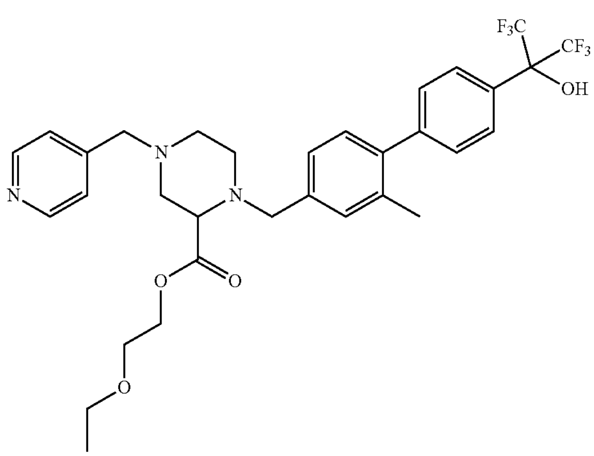 [SMILES: CCOCCOC(=O)C1CN(Cc2ccncc2)CCN1Cc1ccc(-c2ccc(C(O)(C(F)(F)F)C(F)(F)F)cc2)c(C)c1] | 2-ethoxyethyl 1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 190 |

TABLE 1-continued

| Compound No. | Structure | Compound name | Synthetic Protocol/ Intermediates to be used |
|---|---|---|---|
| 171 | 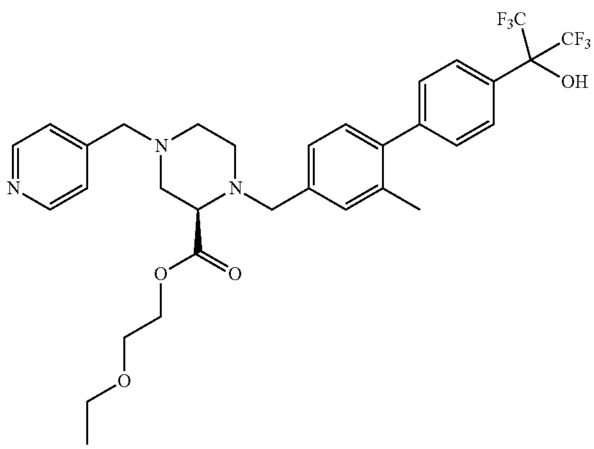 [SMILES: CCOCCOC(=O)[C@H]1CN(Cc2ccncc2)CCN1Cc1ccc(-c2ccc(C(O)(C(F)(F)F)C(F)(F)F)cc2)c(C)c1] | 2-ethoxyethyl (R)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylate | Protocol E using 191 |
| 172 | 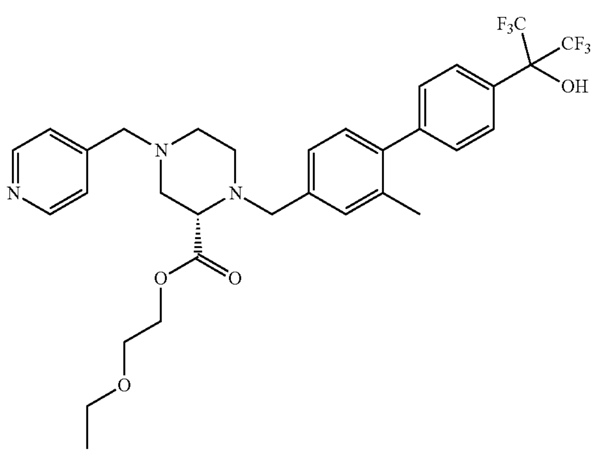 [SMILES: CCOCCOC(=O)[C@@H]1CN(Cc2ccncc2)CCN1Cc1ccc(-c2ccc(C(O)(C(F)(F)F)C(F)(F)F)cc2)c(C)c1] | 2-ethoxyethyl (S)-1-((4'-(1,1,1,3,3,3-hexafluoro-2-hydroxypropan-2-yl)-2-methyl-[1,1'-biphenyl]-4-yl)methyl)-4-(pyridin-4-ylinethyl)piperazine-2-carboxylate | Protocol E using 192 |
| 173 | 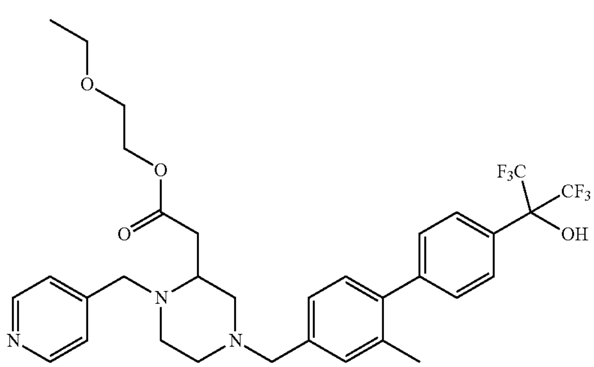 [SMILES: CCOCCOC(=O)CC1CN(Cc2ccc(-c3ccc(C(O)(C(F)(F)F)C(F)(F)F)cc3)c(C)c2)CCN1Cc1ccncc1] | 2-ethoxyethyl 2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 193 |

TABLE 1-continued

| Compound No. | Structure | Compound name | Synthetic Protocol/ Intermediates to be used |
|---|---|---|---|
| 174 | 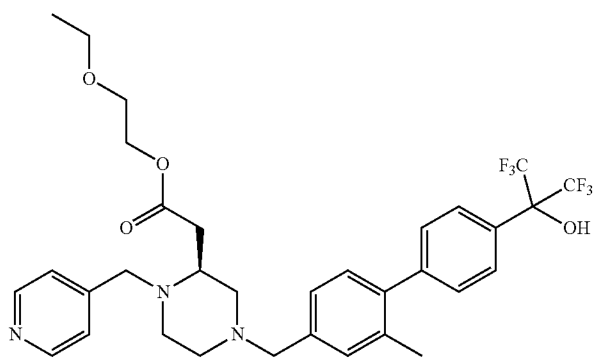 [SMILES: CCOCCOC(=O)C[C@H]1CN(Cc2ccc(-c3ccc(C(O)(C(F)(F)F)C(F)(F)F)cc3)c(C)c2)CCN1Cc1ccncc1] | 2-ethoxyethyl (S)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 50 |
| 175 | 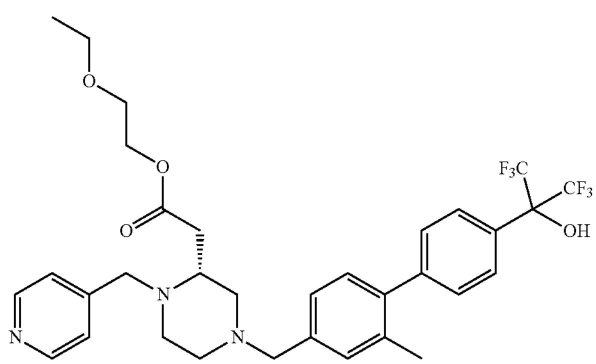 [SMILES: CCOCCOC(=O)C[C@@H]1CN(Cc2ccc(-c3ccc(C(O)(C(F)(F)F)C(F)(F)F)cc3)c(C)c2)CCN1Cc1ccncc1] | 2-ethoxyethyl (R)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetate | Protocol F using 194 |
| 176 | 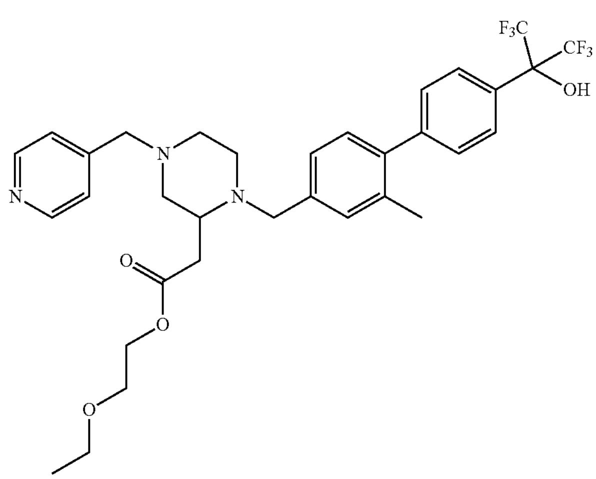 [SMILES: CCOCCOC(=O)CC1CN(Cc2ccncc2)CCN1Cc1ccc(-c2ccc(C(O)(C(F)(F)F)C(F)(F)F)cc2)c(C)c1] | 2-ethoxyethyl 2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 195 |

TABLE 1-continued

| Compound No. | Structure | Compound name | Synthetic Protocol/ Intermediates to be used |
|---|---|---|---|
| 177 | 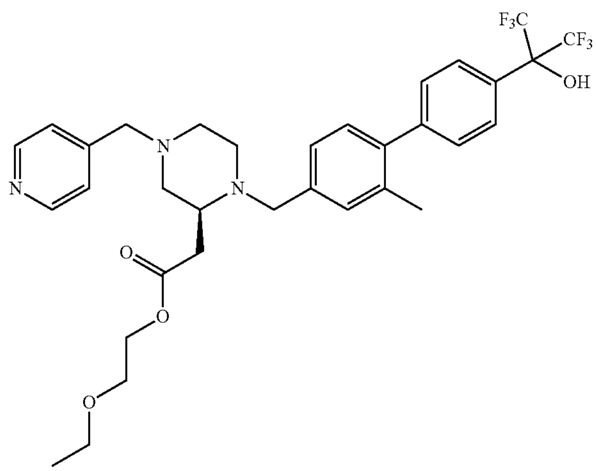 [SMILES: CCOCCOC(=O)C[C@H]1CN(Cc2ccncc2)CCN1Cc1ccc(-c2ccc(C(O)(C(F)(F)F)C(F)(F)F)cc2)c(C)c1] | 2-ethoxyethyl (S)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 196 |
| 178 | 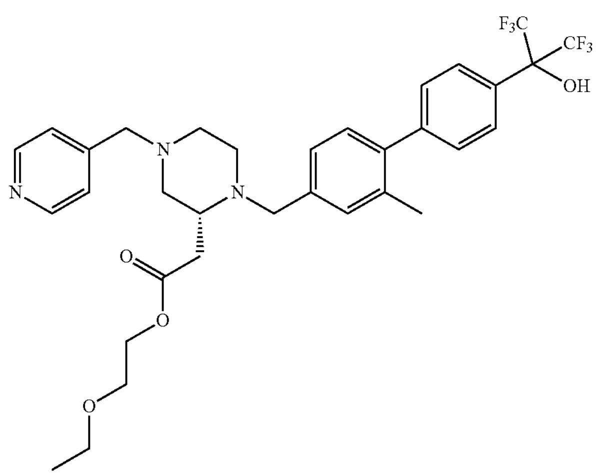 | 2-ethoxyethyl (R)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetate | Protocol E using 189 |
| 179 | 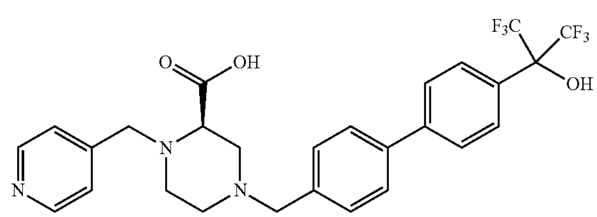 [SMILES: O=C(O)[C@H]1CN(Cc2ccc(-c3ccc(C(O)(C(F)(F)F)C(F)(F)F)cc3)cc2)CCN1Cc1ccncc1] | (R)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylic acid | Protocol D using 95 |
| 180 | 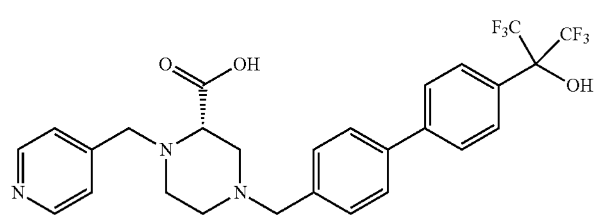 [SMILES: O=C(O)[C@@H]1CN(Cc2ccc(-c3ccc(C(O)(C(F)(F)F)C(F)(F)F)cc3)cc2)CCN1Cc1ccncc1] | (S)-4-((4'-(1,1,1,3,3,3-hexafluoro-2-hydroxypropan-2-yl)-[1,1'-biphenyl]-4-yl)methyl)-1-(pyridin-4-ylmethyl)piperazine-2-carboxylic acid | Protocol D using 96 |

TABLE 1-continued

| Compound No. | Structure | Compound name | Synthetic Protocol/ Intermediates to be used |
|---|---|---|---|
| 181 | 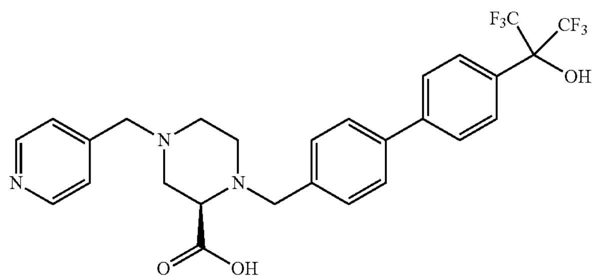 [SMILES: O=C(O)[C@H]1CN(Cc2ccncc2)CCN1Cc1ccc(-c2ccc(C(O)(C(F)(F)F)C(F)(F)F)cc2)cc1] | (R)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylic acid | Protocol B using 97 |
| 182 | 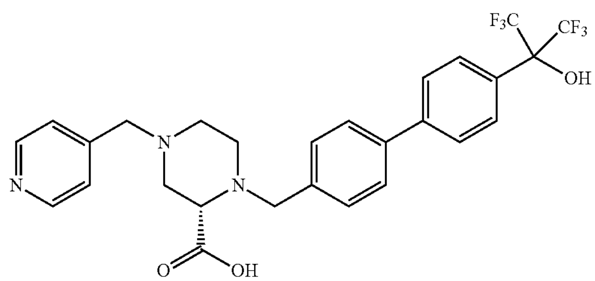 [SMILES: O=C(O)[C@@H]1CN(Cc2ccncc2)CCN1Cc1ccc(-c2ccc(C(O)(C(F)(F)F)C(F)(F)F)cc2)cc1] | (S)-1-((4'-(1,1,1,3,3,3-hexafluoro-2-hydroxypropan-2-yl)-[1,1'-biphenyl]-4-yl)methyl)-4-(pyridin-4-ylmethyl)piperazine-2-carboxylic acid | Protocol B using 98 |
| 183 | 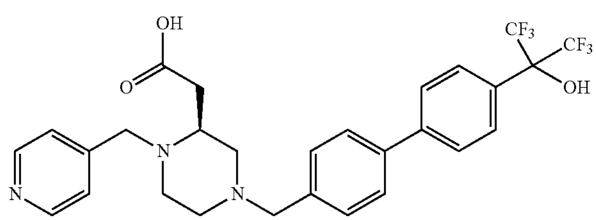 [SMILES: O=C(O)C[C@H]1CN(Cc2ccc(-c3ccc(C(O)(C(F)(F)F)C(F)(F)F)cc3)cc2)CCN1Cc1ccncc1] | (S)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetic acid | Protocol D using 48 |
| 184 | 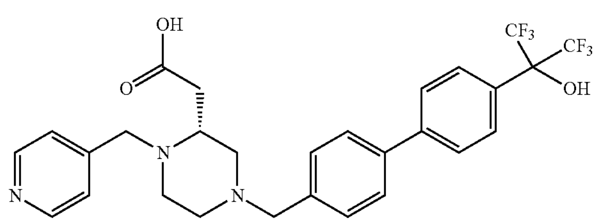 [SMILES: O=C(O)C[C@@H]1CN(Cc2ccc(-c3ccc(C(O)(C(F)(F)F)C(F)(F)F)cc3)cc2)CCN1Cc1ccncc1] | (R)-2-(4-((4'-(1,1,1,3,3,3-hexafluoro-2-hydroxypropan-2-yl)-[1,1'-biphenyl]-4-yl)methyl)-1-(pyridin-4-ylmethyl)piperazin-2-yl)acetic acid | Protocol D using 49 |
| 185 | 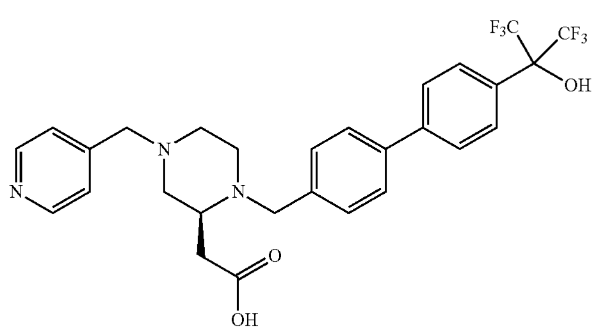 [SMILES: O=C(O)C[C@H]1CN(Cc2ccncc2)CCN1Cc1ccc(-c2ccc(C(O)(C(F)(F)F)C(F)(F)F)cc2)cc1] | (S)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetic acid | Protocol B using 99 |

TABLE 1-continued

| Compound No. | Structure | Compound name | Synthetic Protocol/ Intermediates to be used |
|---|---|---|---|
| 186 | 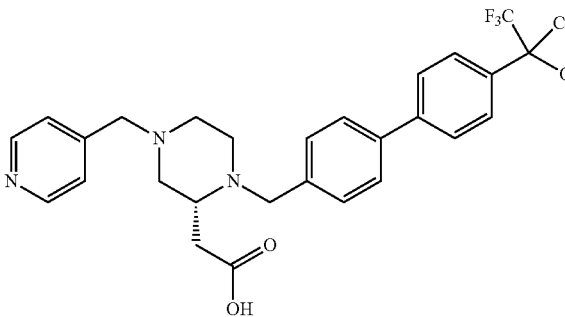 | (R)-2-(1-((4'-(1,1,1,3,3,3-hexafluoro-2-hydroxypropan-2-yl)-[1,1'-biphenyl]-4-yl)methyl)-4-(pyridin-4-ylmethyl)piperazin-2-yl)acetic acid | Protocol B using 100 |
| 187 | 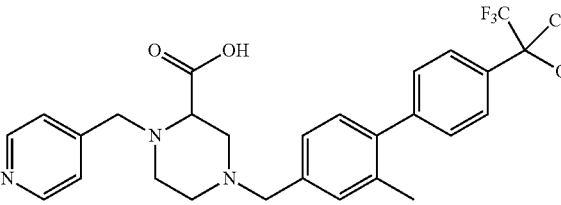 | 4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylic acid | Protocol D using 101 |
| 188 | 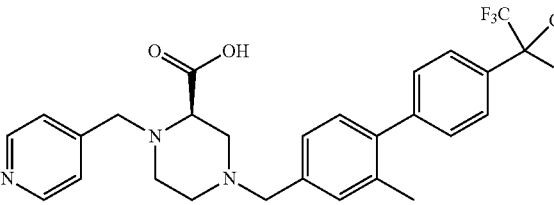 | 4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylic acid | Protocol D using 103 |
| 189 | 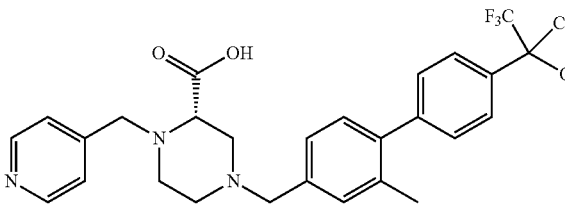 | (S)-4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazine-2-carboxylic acid | Protocol D using 102 |
| 190 | 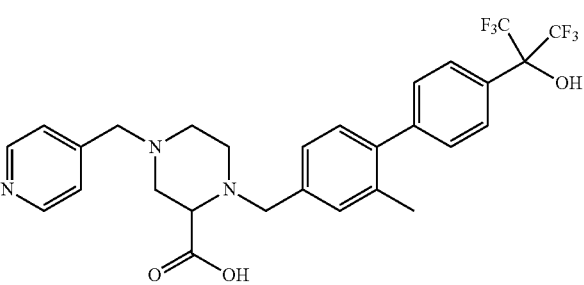 [SMILES: Cc1cc(CN2CCN(Cc3ccncc3)CC2C(=O)O)ccc1-c1ccc(C(O)(C(F)(F)F)C(F)(F)F)cc1] | 1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylic acid | Protocol B using 105 |
| 191 | 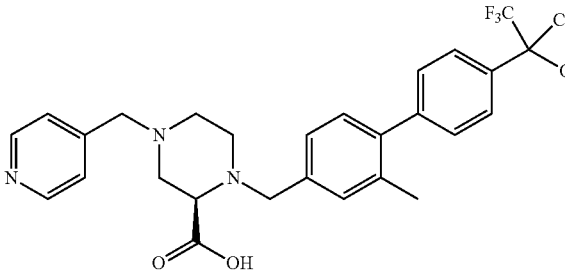 | (R)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylic acid | Protocol B using 106 |

TABLE 1-continued

| Compound No. | Structure | Compound name | Synthetic Protocol/ Intermediates to be used |
|---|---|---|---|
| 192 | 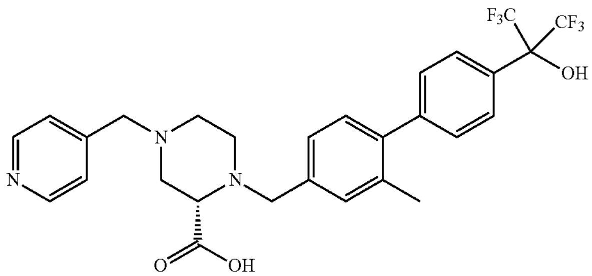 [SMILES: Cc1cc(CN2CCN(Cc3ccncc3)C[C@H]2C(=O)O)ccc1-c1ccc(C(O)(C(F)(F)F)C(F)(F)F)cc1] | (S)-1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazine-2-carboxylic acid | Protocol B using 107 |
| 193 | 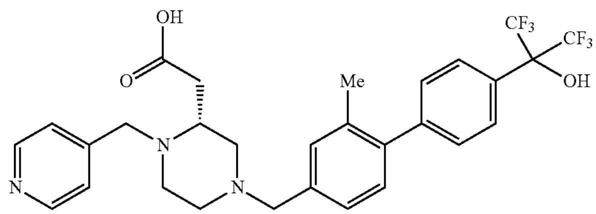 [SMILES: Cc1cc(CN2CCN(Cc3ccncc3)[C@H](CC(=O)O)C2)ccc1-c1ccc(C(O)(C(F)(F)F)C(F)(F)F)cc1] | 2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetic acid | Protocol D using 18 |
| 194 | 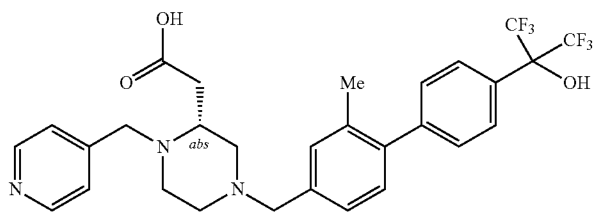 [SMILES: Cc1cc(CN2CCN(Cc3ccncc3)[C@H](CC(=O)O)C2)ccc1-c1ccc(C(O)(C(F)(F)F)C(F)(F)F)cc1] | (R)-2-(4-((4'-(1,1,1,3,3,3-hexafluoro-2-hydroxypropan-2-yl)-2-methyl-[1,1'-biphenyl]-4-yl)methyl)-1-(pyridin-4-ylmethyl)piperazin-2-yl)acetic acid | Protocol D using 104 |
| 195 | 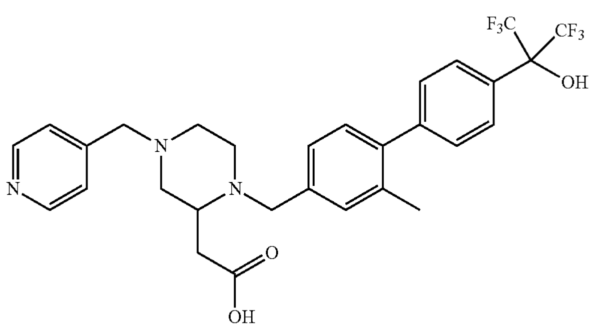 [SMILES: Cc1cc(CN2CCN(Cc3ccncc3)CC2CC(=O)O)ccc1-c1ccc(C(O)(C(F)(F)F)C(F)(F)F)cc1] | 2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetic acid | Protocol B using 108 |
| 196 | 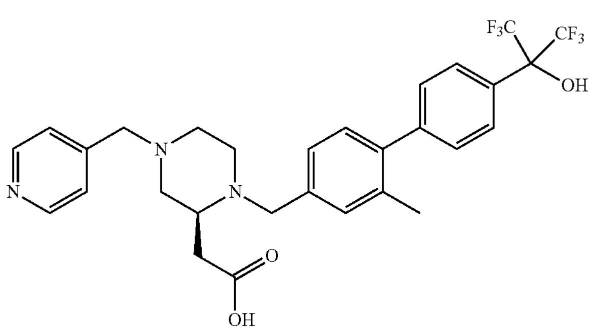 [SMILES: Cc1cc(CN2CCN(Cc3ccncc3)C[C@@H]2CC(=O)O)ccc1-c1ccc(C(O)(C(F)(F)F)C(F)(F)F)cc1] | (S)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetic acid | Protocol B using 110 |

TABLE 1-continued

| Compound No. | Structure | Compound name | Synthetic Protocol/ Intermediates to be used |
|---|---|---|---|
| 197 | 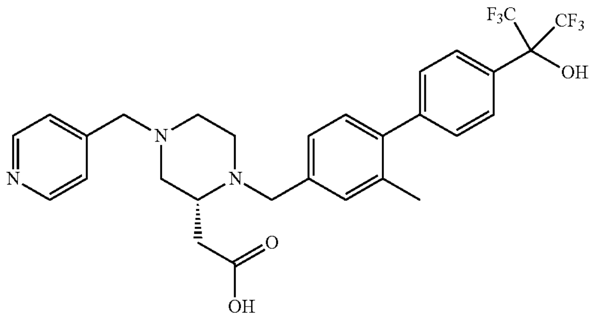 | (R)-2-(1-((4'-(1,1,1,3,3,3-hexafluoro-2-hydroxypropan-2-yl)-2-methyl-[1,1'-biphenyl]-4-yl)methyl)-4-(pyridin-4-ylmethyl)piperazin-2-yl)acetic acid | Protocol B using 109 |

Example 25: Gal4 Ligand Binding Assay

Human RORγ ligand binding assay was performed in 96-well format. The N-terminal DNA binding domains (DBD) of the native RORγ and RORγt receptors have been substituted with that of the yeast GAL4-DBD and RORγ is expressed constitutively in the cell line. Both agonist and inverse agonist activity can be detected. 10 mM compound stocks were diluted serially 1:3 with DMSO and further diluted with provided media to generate 10 titration points from 60 μM to 3 nM. These treatment conditions were added to the plates as 2× media in 100 μL volume. Each plate includes a positive control with 10 titration points as well as 6 negative control wells with vehicle only. Reporter cells were rapidly thawed and added to the plates in 100 μL volume. The plates were incubated for 24 hrs in a 37° C. humidified 5% $CO_2$ incubator. Media was removed before the addition of room temperature Detection Substrate. After 5 minute incubation, the luminescence was quantified on a luminescence plate reader.

TABLE 2

IC$_{50}$ values for RORγt inverse agonists in RORγt Gal fusion assay.

| Compound | RORγt (IC$_{50}$) |
|---|---|
| 9 | A |
| 10 | A |
| 12 | B |
| 13 | B |
| 17 | A |
| 18 | A |
| 20 | C |
| 21 | C |
| 24 | C |
| 25 | NT |
| 28 | B |
| 29 | NT |
| 30 | A |
| 31 | A |
| 32 | A |
| 33 | B |
| 35 | A |
| 47 | A |
| 48 | A |
| 49 | A |
| 50 | B |
| 51 | A |

A: IC$_{50}$ < 1 μM;
B: IC$_{50}$ = 1-10 μM;
C: IC$_{50}$ > 10 μM;
NT: not tested

Example 26: Gal4 Mouse Primary CD4 T Cell Th17 Differentiation Assay

Mouse primary lymphocytes were stimulated and cultured under the TH17 polarization condition. CD4 T cells differentiate into TH17 cells by expressing RORγt and producing cytokines controlled by this master transcriptional regulator, such as IL-17A. In the presence of RORγt inverse agonists, TH17 cell differentiation is inhibited and reduction of IL-17A production is quantitatively correlated to the efficiency of RORγt inhibition.

24-well tissue culture plates were coated with 2 μg/mL anti-mouse CD3 overnight at 4° C. and washed with PBS post incubation. Single-cell suspension of C57BL/6 mice splenocytes were added to the plates at $2 \times 10^6$ cells/well in 250 μL volume. Compounds stocks diluted with media were added to the wells in 4× concentration and 250 μL volume. Th17 polarization cocktails (final concentration 10 g/mL anti-CD28, 5 μg/mL anti-IL-4, 5 μg/mL anti-IFNg, 1 μg/mL anti-IL-2, 40 ng/mL rIL-6, 10 ng/mL rTGF-β1) was added to the wells at 2× concentration in 500 μL volume and cells were incubated at 37° C. in a humidified 5% $CO_2$ incubator for 4 days. On the 4$^{th}$ day, 2 μL 500× cell stimulation cocktail (PMA/I) with Golgi Transporter inhibitor was added to each well for 3 hours before the cells were harvested for intracellular cytokine staining. Cells were stained for IL-17, IFN-γ and viability dye. Shown in FIG. 1 is the inhibition of Th17 cell differentiation with reduction of IL-17A+ cells by 50% in the presence of a compound of Formula (I) (Compound B) at 1.25 μM for 3 days.

Example 27: Rat Pharmacokinetics

The plasma pharmacokinetics of compounds of Formula (I), (Ia), or (Ib) were investigated in male Sprague Dawley rats following a single intravenous and a different oral formulation administration, with three rats in each dosing group. The compounds were formulated in a solution comprised of 2.5% NMP, 5% Solutol HS-15 and 92.5% normal Saline at 1 mg/kg dose for i.v., and in a solution formulation of citric acid (6% w/v solution in RO water) at 10 mg/kg dose for p.o. Blood samples (approximately 60 µL) were collected at 0.08, 0.25, 0.5, 1, 2, 4, 8, 12 and 24 hr (i.v.) and 0.25, 0.5, 1, 2, 4, 6, 8, 12 and 24 hr (p.o.) with $K_2EDTA$ as anticoagulant. Plasma samples were separated by centrifugation of whole blood and stored below −70° C. until bioanalysis. All samples were processed for analysis by protein precipitation using acetonitrile (ACN) and analyzed with fit for purpose LC/MS/MS method. Pharmacokinetic parameters were calculated using the non-compartmental analysis tool of Phoenix WinNonlin (Version 6.3).

Figure 2:
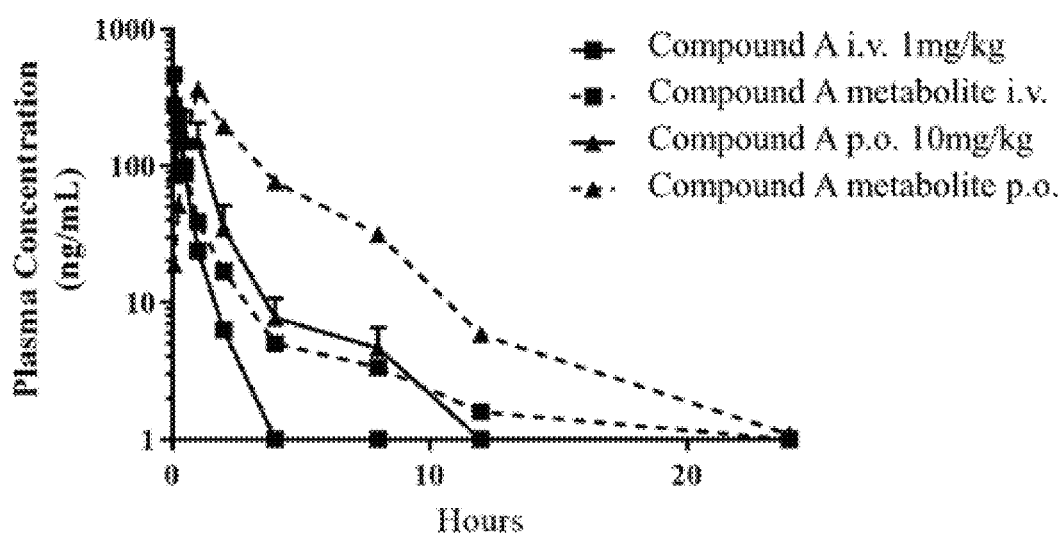
FIG. 2 shows a pharmacokinetic plot of a compound of Formula (I) (Compound A) dosed in rats.
Figure 3:
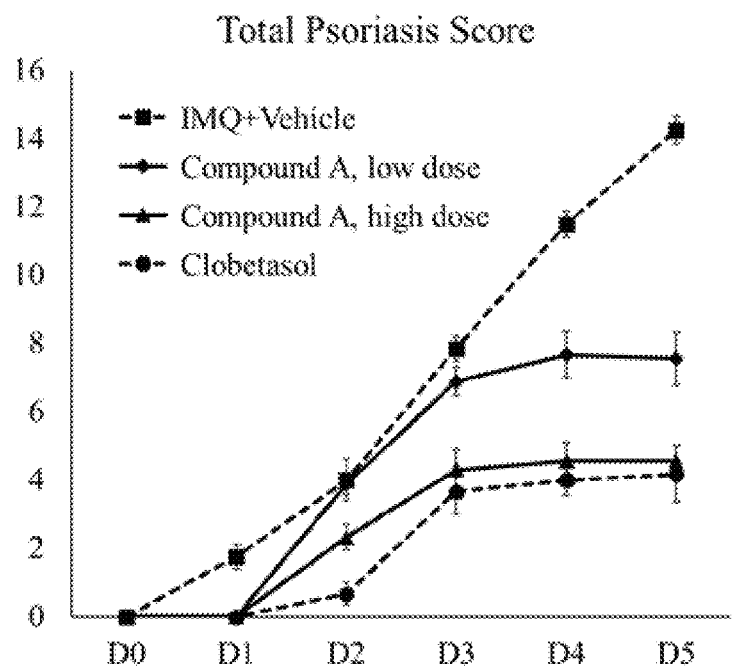
FIG. 3 shows the total psoriasis score for mice treated with a compound of Formula (I) (Compound A) in the imiquimod (IMQ) induced mouse psoriasis model.
Figure 4:
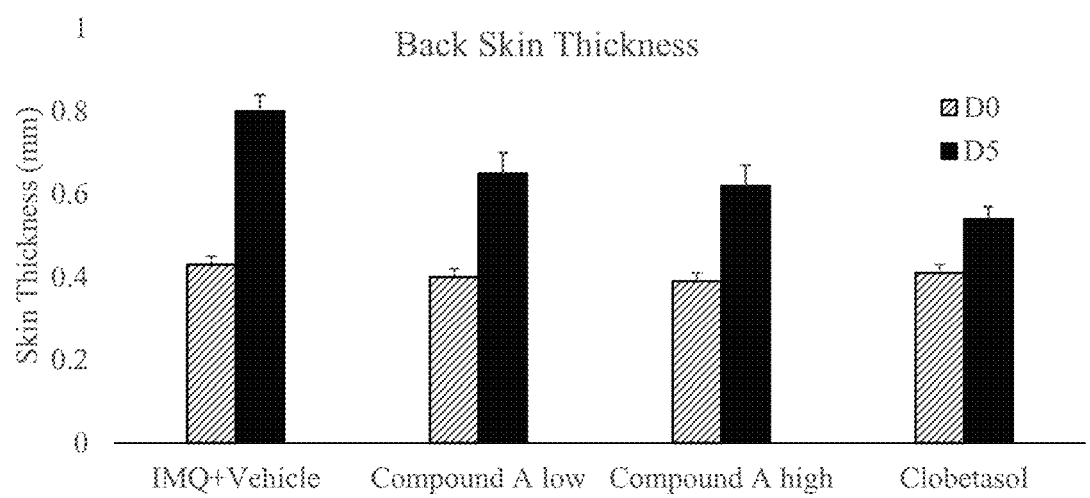
FIG. 4 shows the back skin thickness for mice treated with a compound of Formula (I) (Compound A) in the imiquimod (IMQ) induced mouse psoriasis model.
Figure 5:
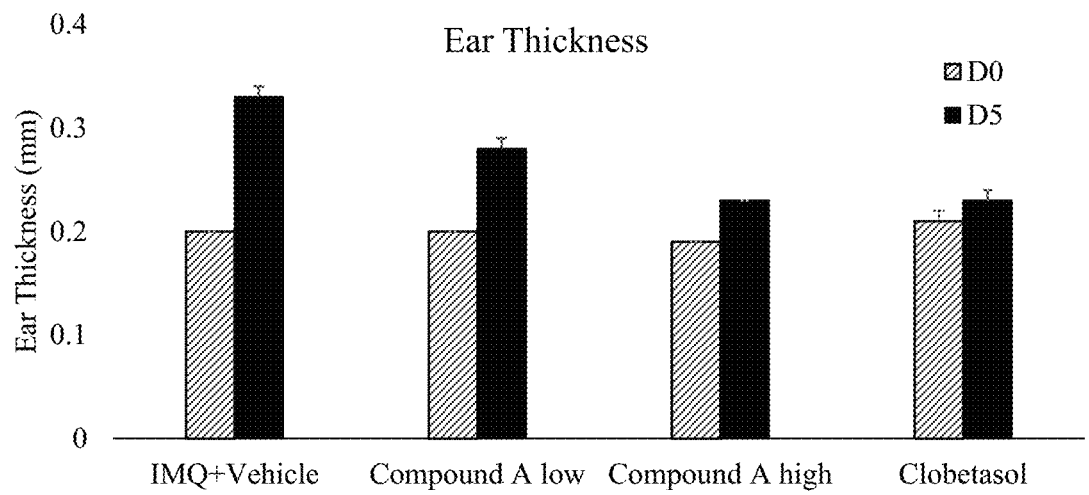
FIG. 5 shows the ear thickness for mice treated with a compound of Formula (I) (Compound A) in the imiquimod (IMQ) induced mouse psoriasis model.
Figure 6:
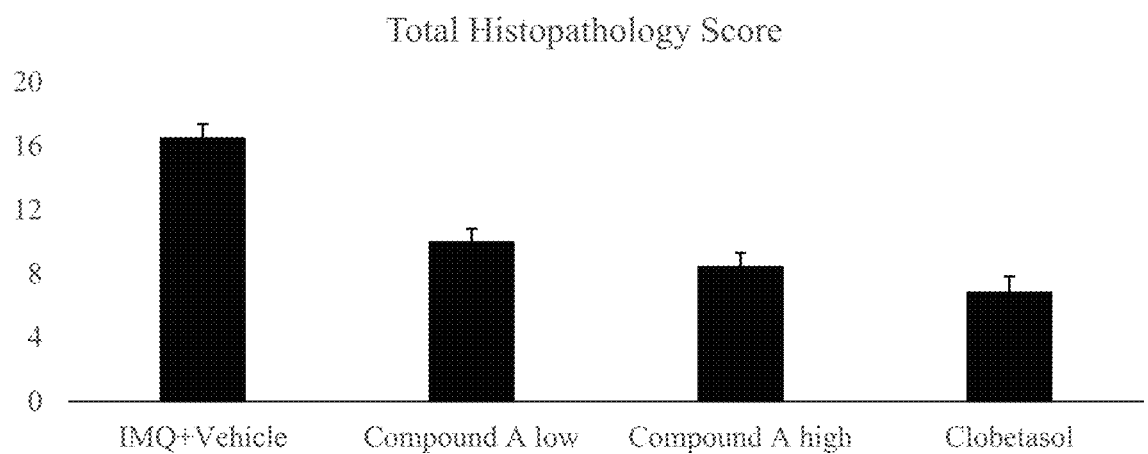
FIG. 6 shows the total histopathology score for mice treated with a compound of Formula (I) (Compound A) in the imiquimod (IMQ) induced mouse psoriasis model.

FIG. 2 shows the pharmacokinetic plot of a compound of Formula (I) (Compound A). Following a single intravenous administration to rats at 1 mg/kg dose, Compound A showed high plasma clearance (90.01 mL/min/kg, the normal liver blood flow in rats=55 mL/min/kg) with a mean elimination half-life of 0.58 hr. The $V_{SS}$ was 4.2-fold more than normal volume of total body water (0.7 L/kg). Plasma concentrations of the deactivated metabolite of Compound A were quantifiable up to 12 hr.

Following a single oral administration to male Sprague Dawley rats at 10 mg/kg dose, plasma concentrations of Compound A were quantifiable up to 8 hr with mean Tmax at 1.67 hr. Oral solution bioavailability was 27%. Plasma concentrations of the deactivated metabolite of Compound A were quantifiable up to 24 hr with mean Tmax at 2 hr.

Example 28: In Vivo Efficacy in Imiquimod (IMQ) Induced Mouse Psoriasis Model

Compounds of Formula (I), (Ia), or (Ib) were tested in the imiquimod (IMQ) induced psoriasis model in mice to determine their in vivo efficacy as topical agents. Female Balb/c mice of age 8-10 weeks were allowed to acclimatize for at least seven days prior to experiment initiation. During this period, the mice were observed daily for clinical signs. Animals were randomly assigned to studies group on Day zero (DO) before anaesthetization and back hair was completely removed by using a depilatory cream. One group of animals served as a naïve control (untreated). For remaining three groups, a daily topical dose of 62.5 mg of a cream preparation containing 5% Imiquimod: 47 mg on hair-free back of mice and 15.5 mg on right ear was administered to establish a model of IMQ-induced psoriasis. Animals were treated with formulation of w/w 4% ethanol, 15% DMI, 0.5% BHT (solid), 5% propyleneglycol. 8.5% glycerol, 10% HPC (solid) and 57% PEG400 (in the vehicle control group), representative compounds of Formula (I), (Ia), or (Ib) at 0.3, 1, 3% (w/v) formulated in vehicle (in the study group), or standard clobetasol (in the positive control group), daily for 5 days, 4 hours before IMQ application. The severity of psoriasis was monitored and graded daily using a modified human scoring system, the Psoriasis Area and Severity Index (PASI), which consists of measures for ear and skin erythema, scaling and thickness. At the end of the study period, 24 hours after the final dosing, all animals were humanely sacrificed, and blind histopathological scoring was performed by pathologist on H&E stained tissue sections of the ear and back.

FIGS. 3-6 show the in vivo efficacy results obtained from treatment with a compound of Formula (I) (Compound A) in this psoriasis model. All the animals treated with Compound A were found to be normal and active (no signs of skin irritation, no changes in posture, gait and response to handling behavior, no secretions and excretions, normal body movement display) during the treatment period. No morbidity or mortality was found. Vehicle control group treated with IMQ showed significant increase in total psoriasis score with pronounced erythema, scaling and increased thickness. Histology sections of the back skin and ear showed massive immune infiltration, hyperkarotosis and pustule formation. Pre-treatment with clobetasol significantly decreased psoriasis score, ear and back skin thickness, as well as histopathology scoring. Pre-treatment with Compound A showed a dose dependent decrease of all three read-outs (1% dose of Compound A not shown in figures). The responses from the high dose Compound A treated group (3% dose of Compound A) is not statistically different from the responses from clobetasol treatment.

Example 29: Phase I Clinical Trial to Evaluate the Safety, Tolerability and Pharmacokinetics of Compounds of Formula (I), (Ia), or (Ib) in Patients with Mild to Moderate Psoriasis The purpose of this phase I trial is to evaluate the safety, tolerability and pharmacokinetics of a topical administration of a compound of Formula (I), (Ia), or (Ib) in patients with mild to moderate psoriasis.

Patients:

Eligible subjects will be men and women 18 years of age and older.

Criteria:

Inclusion Criteria:

Clinical diagnosis of plaque psoriasis for at least six months with multiple treatable area (i.e. the lesion should not only on the face, scalp, genitals or skinfolds) of plaque psoriasis covering less than 10% of the total Body Surface Area (BSA), affected area on the limb and/or trunk≥1% BSA. A Target Plaque Area (TPA)≥9 cm2, with a Target Plaque Severity Score (TPSS)≥5, and induration subscore≥2.

Male participants should be ≥50 kg, female participants should be ≥45 kg; BMI should be between 19 and 28 kg/m2 (inclusive)

In good health, with no history of diseases of major organs and no abnormality found on physical examination and vital signs Non-allergic, with no known history of drug allergy Men and women of childbearing potential must agree to use a contraceptive regimen agreed by the doctor during the trial. Female subjects that are on hormonal contraceptives must continue using the same hormonal contraceptive as that was used in the past 3 months, with the same route of administration and the same dose during the study Have signed a written informed consent before entering the study.

Exclusion Criteria:

Psoriasis guttata, psoriasis punctata, erythrodermic psoriasis, pustular psoriasis, psoriasis arthritis Any dermatological disease that might interfere psoriasis clinical evaluation or bring the subject in danger, or have other serious dermatological disease other than psoriasis Have received underlying treatments before entering the trial: Topical anti-psoriasis treatment in 2 weeks, e.g. corticosteroids, retinoids acid, anthranol, tars, keratolytics. Vitamin D analogues or local immune regulator treatment in 4 weeks; Emollient or cosmetics in 24 hours; Any psoriasis vaccine, or have participated in any psoriasis vaccine trial; Biologics treatment in 12 weeks, e.g. Alefacept, Etanercept, Infliximab, Adalimumab, Ustekinumab, Efalizumab; Any phototherapy or systemic treatment in 4 weeks, e.g. corticosteroids, methotrexate, retinoids acids, ciclosporin; Long time exposure to natural light or artificial UV, or will have such exposure; Use of drug known to harm certain organ in 12 weeks; Participated in any clinical trial in 4 weeks, or have plan to participate any trial during treatment period;

Any clinically significant central nervous, cardiac, hepatic, renal, gastrointestinal, respiratory, metabolic or musculoskeletal system disease history, or other pathological/physiological condition that might disrupt the trial result Alanine transaminase (ALT), aspartate aminotransferase (AST), total bilirubin>1.5 Upper Limit Normal (ULN), creatinine>ULN History of postural hypotension, or allergic diseases (asthma, urticaria, atopic dermatitis or rhinitis)

Pulmonary disease demonstrated by chest X-ray examination

Physically or mentally disabled

Positive for Hepatitis B Surface Antigen (HBsAg), hepatitis C or anti-HIV test

Know allergic to active ingredient or excipient of the investigational product

Excessive smoker (>10 cigarettes per day), or excessive alcohol intake (>15 g absolute alcohol per day, equal to 450 ml beer, 150 ml wine or 50 ml low-alcohol Chinese liquor)

Excessive drinking of tea, coffee or caffein-containing beverage (>8 glasses per day)

Drug abuser

Poor compliance

Under gestation or lactation period

Other subject that in the investigator's opinion unsuitable to be enrolled.

Study Design:

Allocation: Randomized

Endpoint Classification: Safety Study

Intervention Model: Parallel Assignment

Masking: Double Blind (Subject, Investigator)

Primary Purpose: Treatment

Primary Outcome Measures:

Safety in patients with mild to moderate psoriasis: Incidence and severity of Adverse Events (AE), Physical Examinations, Vital signs (temperature, Heart Rate (HR), BP and respiration); Clinical laboratory assessments (serum chemistry, hematology, C-reactive protein, fecal and urinalysis); ECG Secondary Outcome Measures:

Tolerance-related skin reactions in patients with mild to moderate psoriasis at the treatment site: Skin irritation and allergy observation (including redness, swelling, rash, itching, pain) recorded by grades Other Outcome Measures:

Lesion severity Erythema, scale, thickness of target site on patients with mild to moderate psoriasis Lesion area [Time Frame: 28 days] [Designated as safety issue: No]

Psoriasis Area and Severity Index (PASI) Scores in patients with mild to moderate psoriasis [Time Frame: 28 days] [Designated as safety issue: No]

Physician's Global Assessment (PGA) in patients with mild to moderate psoriasis [Time Frame: 28 days] [Designated as safety issue: No]

Dermatology Life Quality Index (DLQI) in patients with mild to moderate psoriasis [Time Frame: 28 days] [Designated as safety issue: No]

Time maximum concentration observed (tmax) of a single-dose of a Compound of Formula (I), (Ia), or (Ib) Cream in patients with mild to moderate psoriasis [Time Frame: 12 hours] [Designated as safety issue: No]

Peak plasma concentration (Cmax) of single-dose of a Compound of Formula (I), (Ia), or (Ib) Cream patients with mild to moderate psoriasis [Time Frame: 12 hours] [Designated as safety issue: No]

Area under the plasma concentration versus time curve (AUC) of a single-dose of a Compound of Formula (I), (Ia), or (Ib) Cream from zero (0) hours to time (t) in patients with mild to moderate psoriasis [Time Frame: 12 hours] [Designated as safety issue: No]

Area under the plasma concentration versus time curve (AUC) of a single-dose of a Compound of Formula (I), (Ia), or (Ib) Cream from zero (0) hours to infinity ($\infty$) in patients with mild to moderate psoriasis [Time Frame: 12 hours] [Designated as safety issue: No]

Half life (t½) of a single-dose of a Compound of Formula (I), (Ia), or (Ib) Cream in patients with mild to moderate psoriasis [Time Frame: 12 hours] [Designated as safety issue: No]

Time maximum concentration observed (tmax) of a repeat-dose of a Compound of Formula (I), (Ia), or (Ib) Cream in patients with mild to moderate psoriasis [Time Frame: 24 hours] [Designated as safety issue: No]

Stable peak plasma concentration (Cmax) of a repeat-dose of a Compound of Formula (I), (Ia), or (Ib) Cream in patients with mild to moderate psoriasis [Time Frame: 24 hours] [Designated as safety issue: No]

Area under the plasma concentration versus time curve (AUC) of a repeat-dose of a Compound of Formula (I), (Ia), or (Ib) Cream from zero (0) hours to time (t) in patients with mild to moderate psoriasis [Time Frame: 24 hours] [Designated as safety issue: No]

Area under the plasma concentration versus time curve (AUC) of a repeat-dose of a Compound of Formula (I), (Ia), or (Ib) Cream from zero (0) hours to infinity ($\infty$) in patients with mild to moderate psoriasis [Time Frame: 24 hours] [Designated as safety issue: No]

Half life (t½) of a repeat-dose of a Compound of Formula (I), (Ia), or (Ib) Cream in patients with mild to moderate psoriasis [Time Frame: 24 hours] [Designated as safety issue: No]

| Arms | Assigned Interventions |
| --- | --- |
| Experimental: Cohort 1-Experimental 8 patients with mild to moderate psoriasis will be randomized to receive 0.5% Compound of Formula (I), (Ia), or (Ib) Cream, applied twice daily for 4 consecutive weeks. The drug will be applied topically to the psoriasis site. | Drug: 0.5% Compound of Formula (I), (Ia), or (Ib) Cream Topical administration for twice daily Other Name: no other name |

-continued

| Arms | Assigned Interventions |
| --- | --- |
| Placebo Comparator: Cohort 1-Placebo 2 patients with mild to moderate psoriasis will be randomized to receive matching placebo, applied twice daily for 4 consecutive weeks. The drug will be applied topically to the psoriasis site. | Drug: Placebo Topical administration for twice daily Other Name: Blank cream |
| Experimental: Cohort 2-Experimental 8 patients with mild to moderate psoriasis will be randomized to receive 1.0% Compound of Formula (I), (Ia), or (Ib) Cream, applied twice daily for 4 consecutive weeks. The drug will be applied topically to the psoriasis site. | Drug: 1.0% Compound of Formula (I), (Ia), or (Ib) Cream Topical administration for twice daily Other Name: no other name |
| Placebo Comparator: Cohort 2-Placebo 2 patients with mild to moderate psoriasis will be randomized to receive matching placebo, applied twice daily for 4 consecutive weeks. The drug will be applied topically to the psoriasis site. | Drug: Placebo Topical administration for twice daily Other Name: Blank cream |
| Experimental: Cohort 3-Experimental 8 patients with mild to moderate psoriasis will be randomized to receive 2.0% Compound of Formula (I), (Ia), or (Ib) Cream, applied twice daily for 4 consecutive weeks. The drug will be applied topically to the psoriasis site. | Drug: 2.0% Compound of Formula (I), (Ia), or (Ib) Cream Topical administration for twice daily Other Name: no other name |
| Placebo Comparator: Cohort 3-Placebo 2 patients with mild to moderate psoriasis will be randomized to receive matching placebo, applied twice daily for 4 consecutive weeks. The drug will be applied topically to the psoriasis site. | Drug: Placebo Topical administration for twice daily Other Name: Blank cream |
| Experimental: Cohort 4-Experimental 8 patients with mild to moderate psoriasis will be randomized to receive 4.0% Compound of Formula (I), (Ia), or (Ib) Cream, applied twice daily for 4 consecutive weeks. The drug will be applied topically to the psoriasis site. | Drug: 4.0% Compound of Formula (I), (Ia), or (Ib) Cream Topical administration for twice daily Other Name: no other name |
| Placebo Comparator: Cohort 4-Placebo 2 patients with mild to moderate psoriasis will be randomized to receive matching placebo, applied twice daily for 4 consecutive weeks. The drug will be applied topically to the psoriasis site. | Drug: Placebo Topical administration for twice daily Other Name: Blank cream |

The examples and embodiments described herein are for illustrative purposes only and in some embodiments, various modifications or changes are to be included within the purview of disclosure and scope of the appended claims.

What is claimed is:

1. A compound having the structure of Formula (I):

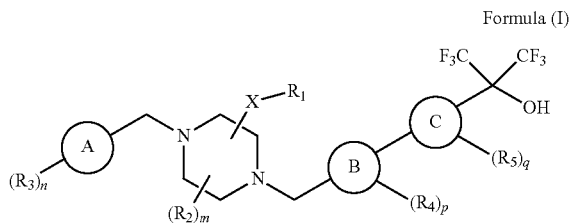

Formula (I)

or a pharmaceutically acceptable salt thereof, wherein:

A is phenyl, 5-membered heteroaryl, or 6-membered heteroaryl;

B is phenyl, 5-membered heteroaryl, or 6-membered heteroaryl;

C is phenyl, 5-membered heteroaryl, or 6-membered heteroaryl;

X is a bond, $C_1$-$C_6$ alkylene, or $C_1$-$C_6$ heteroalkylene;

$R_1$ is $C(O)N(R_6)_2$ or $C(O)OR_6$;

each $R_2$ is independently halogen, $C_1$-$C_6$ alkyl, or $OC_1$-$C_6$ alkyl;

each $R_3$ is independently halogen, CN, $C_1$-$C_6$ alkyl, $C_1$-$C_6$ haloalkyl, $C_1$-$C_6$ heteroalkyl, $C(O)R_8$, $C(O)N(R_7)_2$, $C(O)OR_7$, $N(R_7)_2$, $N(R_7)C(O)R_8$, $N(R_7)S(O)_2R_8$, $OR_7$, $S(O)_2R_8$, or $S(O)_2N(R_7)_2$;

each $R_4$ is independently halogen, CN, $C_1$-$C_6$ alkyl, $C_1$-$C_6$ haloalkyl, $C_1$-$C_6$ heteroalkyl, $C(O)R_8$, $C(O)N(R_7)_2$, $C(O)OR_7$, $N(R_7)_2$, $N(R_7)C(O)R_8$, $N(R_7)S(O)_2R_8$, $OR_7$, $S(O)_2R_8$, or $S(O)_2N(R_7)_2$;

each $R_5$ is independently halogen, CN, $C_1$-$C_6$ alkyl, $C_1$-$C_6$ haloalkyl, $C_1$-$C_6$ heteroalkyl, $C(O)R_8$, $C(O)N(R_7)_2$, $C(O)OR_7$, $N(R_7)_2$, $N(R_7)C(O)R_8$, $N(R_7)S(O)_2R_8$, $OR_7$, $S(O)_2R_8$, or $S(O)_2N(R_7)_2$;

each $R_6$ is independently hydrogen, $C_1$-$C_6$ alkyl, or —$C_1$-$C_6$ alkylene-Y—$R_9$;
each $R_7$ is independently hydrogen, $C_1$-$C_6$ alkyl, $C_1$-$C_6$ haloalkyl, or $C_1$-$C_6$ heteroalkyl;
each $R_8$ is independently $C_1$-$C_6$ alkyl or $C_1$-$C_6$ heteroalkyl;
each $R_9$ is independently hydrogen or $C_1$-$C_6$ alkyl;
each Y is independently —N($R_{10}$)—, —O—, or —S—;
each $R_{10}$ is independently hydrogen or $C_1$-$C_6$ alkyl;
m is 0, 1, 2, 3, or 4;
n is 0, 1, 2, 3, or 4;
p is 0, 1, 2, 3, or 4; and
q is 0, 1, 2, or 3.

2. The compound of claim 1, wherein the compound has the structure of Formula (Ia):

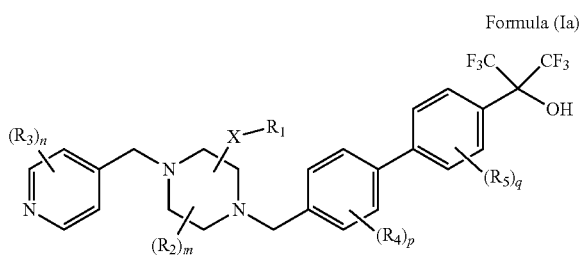

Formula (Ia)

or a pharmaceutically acceptable salt thereof.

3. The compound of claim 2, wherein the compound has the structure of Formula (Ib):

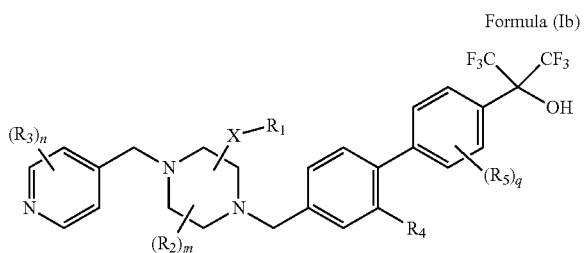

Formula (Ib)

or a pharmaceutically acceptable salt thereof,
wherein:
$R_4$ is hydrogen or $C_1$-$C_6$ alkyl.

4. The compound of claim 3, or a pharmaceutically acceptable salt thereof, wherein X is a bond.

5. The compound of claim 3, or a pharmaceutically acceptable salt thereof, wherein X is $C_1$-$C_6$ alkylene.

6. The compound of claim 5, or a pharmaceutically acceptable salt thereof, wherein X is —$CH_2$—.

7. The compound of claim 3, or a pharmaceutically acceptable salt thereof, wherein $R_1$ is C(O)O$R_6$.

8. The compound of claim 7, or a pharmaceutically acceptable salt thereof, wherein $R_6$ is $C_1$-$C_6$ alkyl.

9. The compound of claim 8, or a pharmaceutically acceptable salt thereof, wherein $R_6$ is $CH_3$, $CH_2CH_3$ or $CH(CH_3)_2$.

10. The compound of claim 7, or a pharmaceutically acceptable salt thereof, wherein $R_6$ is —$C_1$-$C_6$ alkylene—Y—$R_9$.

11. The compound of claim 10, or a pharmaceutically acceptable salt thereof, wherein Y is —O—.

12. The compound of claim 11, or a pharmaceutically acceptable salt thereof, wherein $R_9$ is hydrogen.

13. The compound of claim 11, or a pharmaceutically acceptable salt thereof, wherein $R_9$ is $C_1$-$C_6$ alkyl.

14. The compound of claim 3, or a pharmaceutically acceptable salt thereof, wherein $R_4$ is hydrogen.

15. The compound of claim 3, or a pharmaceutically acceptable salt thereof, wherein $R_4$ is $C_1$-$C_6$ alkyl.

16. The compound of claim 3, or a pharmaceutically acceptable salt thereof, wherein $R_4$ is $CH_3$.

17. The compound of claim 3, or a pharmaceutically acceptable salt thereof, wherein:
m is 0;
n is 0; and
q is 0.

18. A pharmaceutical composition comprising a compound of claim 1, or a pharmaceutically acceptable salt thereof, and a pharmaceutically acceptable diluent, excipient, or binder.

19. A method for modulating retinoic acid related orphan nuclear receptor activity in an individual in need thereof, comprising administering to the individual a therapeutically effective amount of a compound of claim 1, or a pharmaceutically acceptable salt thereof.

20. The method of claim 19, wherein the individual has a dermal disease selected from the group consisting of acne, burns, dermatitis, eczema, psoriasis, rosacea, scarring, skin aging, and urticaria.

21. A compound selected from the group consisting of:

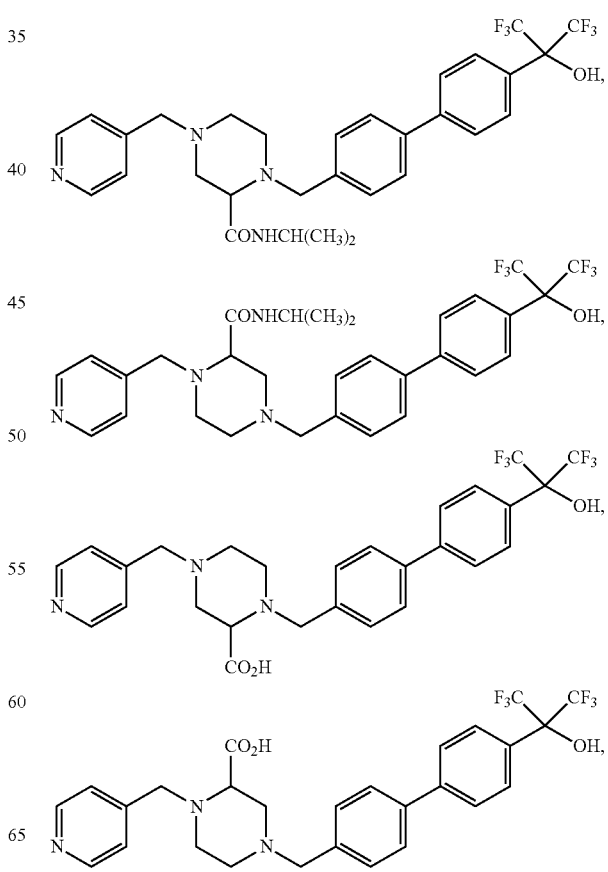

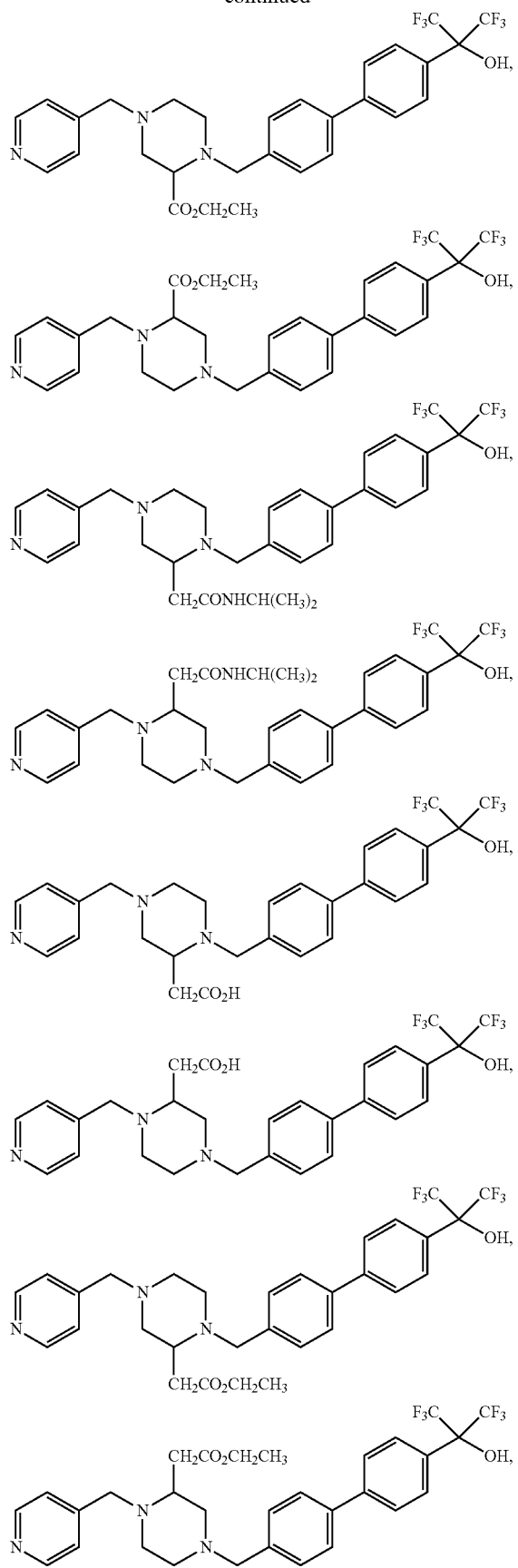
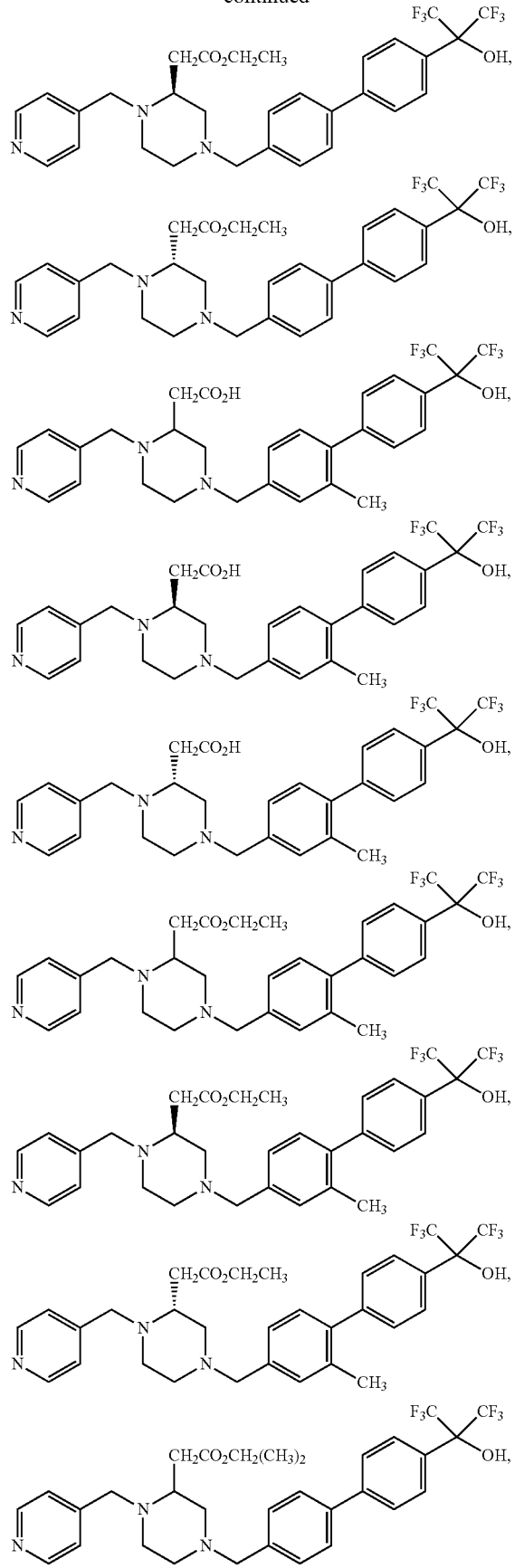

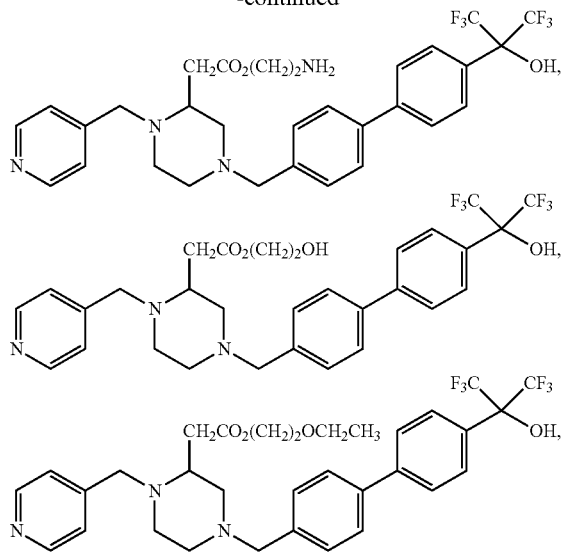
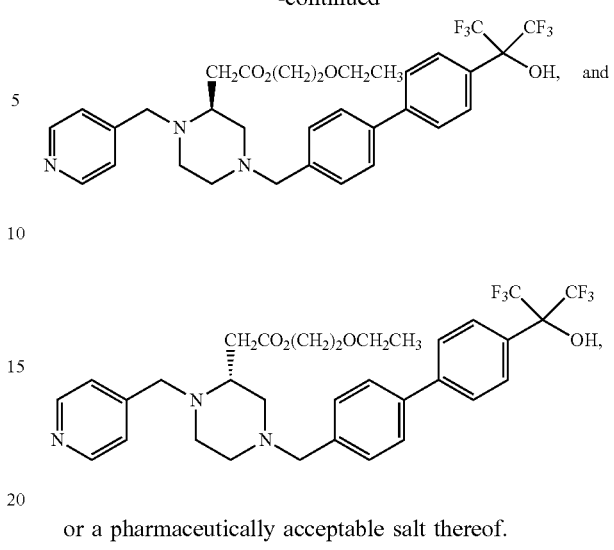
or a pharmaceutically acceptable salt thereof.
* * * * *